US012630639B2

(12) United States Patent
Li et al.

(10) Patent No.: US 12,630,639 B2
(45) Date of Patent: May 19, 2026

(54) ANTI-IFNAR1 ANTIBODIES

(71) Applicants: IMMUNECENT BIOTECHNOLOGY, INC., Guangdong (CN); INSTITUTE OF BIOPHYSICS, CHINESE ACADEMY OF SCIENCES, Beijing (CN)

(72) Inventors: Jingyun Li, Guangdong (CN); Wei Ye, Guangdong (CN); Tao Liu, Guangdong (CN); Xuyuan Zhang, Guangdong (CN); Liguo Zhang, Guangdong (CN); Guangxia Gao, Guangdong (CN)

(73) Assignees: IMMUNECENT BIOTECHNOLOGY, INC., Guangdong (CN); INSTITUTE OF BIOPHYSICS, CHINESE ACADEMY OF SCIENCES, Beijing (CN)

( * ) Notice: Subject to any disclaimer, the term of this patent is extended or adjusted under 35 U.S.C. 154(b) by 1237 days.

(21) Appl. No.: 17/427,655

(22) PCT Filed: Jan. 23, 2020

(86) PCT No.: PCT/CN2020/073939
§ 371 (c)(1),
(2) Date: Aug. 1, 2021

(87) PCT Pub. No.: WO2020/156474
PCT Pub. Date: Aug. 6, 2020

(65) Prior Publication Data

US 2022/0144957 A1 May 12, 2022

(30) Foreign Application Priority Data

Mar. 31, 2019 (WO) ................ PCT/CN2019/074263

(51) Int. Cl.

| | |
|---|---|
| ***C07K 16/28*** | (2006.01) |
| ***A61K 38/21*** | (2006.01) |
| ***A61K 39/395*** | (2006.01) |
| ***G01N 33/68*** | (2006.01) |

(52) U.S. Cl.
CPC ........ *C07K 16/2866* (2013.01); *A61K 38/215* (2013.01); *A61K 39/3955* (2013.01); *G01N 33/6866* (2013.01); *C07K 2317/24* (2013.01); *C07K 2317/31* (2013.01); *C07K 2317/76* (2013.01); *C07K 2317/92* (2013.01); *G01N 2333/7156* (2013.01)

(58) Field of Classification Search
None
See application file for complete search history.

(56) References Cited

U.S. PATENT DOCUMENTS

| | | | |
|---|---|---|---|
| RE30,985 E | 6/1982 | Cartaya | |
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 5,122,469 A | 6/1992 | Mather et al. | |
| 5,571,894 A | 11/1996 | Wels et al. | |
| 5,587,458 A | 12/1996 | King et al. | |
| 5,624,821 A | 4/1997 | Winter et al. | |
| 5,648,260 A | 7/1997 | Winter et al. | |
| 5,731,168 A | 3/1998 | Carter et al. | |
| 6,005,079 A | 12/1999 | Casterman et al. | |
| 6,194,551 B1 | 2/2001 | Idusogie et al. | |
| 6,248,516 B1 | 6/2001 | Winter et al. | |
| 6,713,609 B1 | 3/2004 | Chuntharapai et al. | |
| 9,902,770 B2 | 2/2018 | Chi et al. | |
| 11,136,399 B2 * | 10/2021 | Zhang | A61P 37/02 |
| 2006/0020118 A1 | 1/2006 | Chuntharapai et al. | |
| 2008/0102072 A1 | 5/2008 | Chuntharapai et al. | |
| 2013/0122002 A1 * | 5/2013 | Rubinstein | C12N 15/1138 530/387.3 |
| 2016/0376370 A1 | 12/2016 | Cardarelli et al. | |

FOREIGN PATENT DOCUMENTS

| | | |
|---|---|---|
| CN | 1795010 A | 6/2006 |
| CN | 102863532 A | 1/2013 |
| CN | 106243226 A | 12/2016 |
| CN | 107074943 A | 8/2017 |
| CN | 108310375 A | 7/2018 |
| CN | 109069606 A | 12/2018 |
| EP | 0404097 A2 | 12/1990 |
| WO | 87/00195 A1 | 1/1987 |
| WO | 90/03430 A1 | 4/1990 |
| WO | 93/11161 A1 | 6/1993 |
| WO | 93/16185 A2 | 8/1993 |

(Continued)

OTHER PUBLICATIONS

Janeway, 2001, Immunbiology, The generation of diversity in immunoglobulins Rabia et al. 2018, Biochem. Eng. J. vol. 137: 365-374.*
Scott et al., 2012, vol. 12. Nature Reviews, pp. 278-287 Townsend et al., 2016, Front. Immunol. vol. 7: 1-12.*
Hall, 1992, J. Immunol. vol. 149: 1605-1612 Holt, 2003, Trends biotech. vol. 21: 484-490.*
Chen, 1992, J. Exp. Med. vol. 176: 855-866 Chen, 2018, Front. Immunol. pp. 1-7.*
Sheehan, K.C.F. et al. "Blocking monoclonal antibodies specific for mouse IFN-α/β receptor subunit 1 (IFNAR-1) from mice immunized by in vivo hydrodynamic transfection", Journal of Interferon & Cytokine Research Dec. 31, 2006 (Dec. 31, 2006), No. 11, vol. 26, pp. 804-819.
International Search Report of PCT Application No. PCT/CN2020/073939, mailed on Apr. 22, 2020.

(Continued)

*Primary Examiner* — Amy E Juedes
(74) *Attorney, Agent, or Firm* — Junhe Law Office P.C.; Zhaohui Wang

(57) ABSTRACT

Provided are anti-IFNAR1 antibodies or antigen-binding fragments thereof, isolated poly nucleotides encoding the same, pharmaceutical compositions comprising the same, and the uses thereof.

28 Claims, 20 Drawing Sheets

Specification includes a Sequence Listing.

(56) References Cited

FOREIGN PATENT DOCUMENTS

| | | | |
|---|---|---|---|
| WO | 94/04678 | A1 | 3/1994 |
| WO | 94/25591 | A1 | 11/1994 |
| WO | 94/29351 | A2 | 12/1994 |
| WO | 99/51642 | A1 | 10/1999 |
| WO | 00/42072 | A2 | 7/2000 |
| WO | 2004/094473 | A2 | 11/2004 |
| WO | 2006/034488 | A2 | 3/2006 |
| WO | 2009/100309 | A2 | 8/2009 |
| WO | 2018/010140 | A1 | 1/2018 |
| WO | 2018172957 | A1 | 9/2018 |

OTHER PUBLICATIONS

Shinkawa T. et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity*", J. Biol. Chem, 2003, 278: 3466-3473.

Duncan & Winter, "The binding site for CIq on IgG", Nature 322:738-40 (1988).

Rother RP et al., "Discovery and development of the complement inhibitor eculizumab for the treatment of paroxysmal nocturnal hemoglobinuria", Nat Biotechnol 25:1256-1264 (2007).

Vaughn, D. et al., "Structural basis of pH-dependent antibody binding by the neonatal Fc receptor", Structure, 6(1):63-73, 1998.

Yeung, Y. et al., "A Therapeutic Anti-VEGF Antibody with Increased Potency Independent of Pharmacokinetic Half-life", Cancer Research, 70: 3269-3277 (2010).

Hinton, P. et al., "An Engineered Human IgG1 Antibody with Longer Serum Half-Life", J. Immunology, 176:346-356 (2006).

Morimoto et al., "Single-step purification of F(ab')2 fragments of mouse monodonal antibodies (immunoglobulins G1) by hydrophobic interaction high performance liquid chromatographyusing TSKgel Phenyl-5PW", Journal of Biochemical and Biophysical Methods 24:107-117 (1992).

Brennan et al., "Preparation of Bispecific Antibodies by Chemical Recombination of Monoclonal Immunoglobulin G1 Fragments", Science, 229:81 (1985).

Carter et al., "High Level *Escherichia coil* Expression and Production of a Bivalent Humanized Antibody Fragment", Bio/Technology 10:163-167 (1992).

Batzer et al., "Enhanced evolutionary PCR using oligonucleotides with inosine at the 3'-terminus", Nucleic Acid Res. 19:5081 (1991).

Ohtsuka et al.,"An Alternative Approach to Deoxyoligonucleotides as Hybridization Probes by Insertion of Deoxyinosine at Ambiguous Codon Positions*", J. Biol. Chem. 260:2605-2608 (1985).

Rossolini et al., "Use of deoxyinosine-containing primers vs degenerate primes for polymerase chain reaction based on ambiguous sequence information", Mol. Cell. Probes 8:91-98 (1994).

Graham et al.,"Characteristics of a Human Cell Line Transformed by DNA from Human Adenovirus Type 5", J. Gen Virol. 36:59 (1977).

Urlaub et al., "Isolation of Chinese hamster cell mutants deficient in dihydrofolate reductase activity", Proc. Natl. Acad. Sci. USA 77:4216 (1980).

Mather, "Establishment and Characterization of Two Distinct Mouse Testicular Epithelial Cell Lines", Biol. Reprod. 23:243-251 (1980).

Mather et al.,"Culture of Testicular Cells in Hormone-Supplemented Serum-Free Medium *", Annals N.Y. Acad. Sci. 383:44-68 (1982).

Ham et al.,"Media and Growth Requirements", Meth. Enz. 58:44 (1979).

Barnes et al.,"Methods for Growth of Cultured Cells in Serum-Free Medium", Anal. Biochem. 102:255 (1980).

Lindmark et al., "Binding of Immunoglobulins to Protein A and Immunoglobulin Levels in Mammalian Sera", J. Immunol. Meth. 62:1-13 (1983).

Guss et al.,"Structure of the IgG-binding regions of streptococcal protein G", Embo J. 5:1567 1575 (1986).

Li et al., "Interferon signature gene expression is correlated with autoantibody profiles in patients with incomplete lupus syndromes", Clin Exp Immunol. Mar. 2010, 159(3): 281-291.

Harman et al.,"HIV infection of dendritic cells subverts the IFN induction pathway via IRF-1 and inhibits type 1 IFN production", Blood 2011 118:298-308.

Psarras A, et al., "Type I interferonmediated autoimmune diseases: pathogenesis, diagnosis and targeted therapy", Rheumatology (Oxford) 56:1662-1675 (2017).

Lee-Kirsch Ma et al., "The Type I Interferonopathies", Annu Rev Med 68:297-315 (2017).

Khamashta Met et al., "Sifalimumab, an anti-interferon-α monoclonal antibody, in moderate to severe systemic lupus erythematosus: a randomised, double-blind, placebo-controlled study", Ann Rheum Dis.;75(11):1909-1916 (2016).

Furie Ret et al., "Anifrolumab, an Anti-Interferon-α Receptor Monoclonal Antibody, in Moderate-to-Severe Systemic Lupus Erythematosus", Arthritis Rheumatol 69:376-386 (2017).

Li Peng et al., (2015) "Molecular basis for antagonistic activity of anifrolumab, an anti-interferon-α receptor 1 antibody", mAbs, 7:2, 428-439.

Xinhua Wang et al., "IgG Fc engineering to modulate antibody effector functions", Protein & Cell, 2018, 9(1); 63-73.

Lisa A. Goldman et al., "Characterization of Antihuman IFNAR-1 Monoclonal Antibodies: Epitope Localization and Functional Analysis", Journal of Interferon and Cytokine Research 19:15-26(1999).

Rudikoff S. et al: "Single amino acid substitution altering antigen-binding specificity", Proceedings of the National Academy of Sciences, National Academy of Sciences, vol. 79, No. 6, Mar. 1, 1982 (Mar. 1, 1982), pp. 1979-1983, XP002683593, ISSN: 0027-8424, DOI: 10.1073/PNAS. 79.6 .1979.

Winkler K. et al: "Changing the antigen binding specificity by single point mutations of an anti-p24 (HIV-1) antibody", The Journal of Immunology , Williams & Wilkins Co, US, vol. 165, No. 8, Oct. 15, 2000 (Oct. 15, 2000), pp. 4505-4514, XP002579393, ISSN: 0022-1767.

Gershoni Jonathan M. et al: "Epitope mapping—The first step in developing epitope-based vaccines", BioDrugs, ADIS International Ltd, NZ, vol. 21 , No. 3, Jan. 1, 2007 (Jan. 1, 2007 ), pp. 145-156, XP009103541, ISSN: 1173-8804, DOI: 10.2165/00063030-200721030-00002.

Notice of Reasons for Rejection of the corresponding JP application 2021-544443 , mailed on Nov. 1, 2022.

Invitation pursuant to Rules 62a(1) and 63(1) of the corresponding EP application 20747605.2, mailed on Oct. 11, 2022.

Schreiber G, et al.,"The molecular basis for functional plasticity in type I interferon signaling", (2015) Trends Immunol 36:139-49.

Slavikova M. et al., "Incidence of Autoantibodies Against Type I and Type II Interferons in a Cohort of Systemic Lupus Erythematosus Patients in Slovakia", (2003) J Interferon Cytokine Res 23:143-147.

Hua J, et al., "Functional Assay of Type I Interferon in Systemic Lupus Erythematosus Plasma and Association With Anti-RNA Binding Protein Autoantibodies", (2006) Arthritis Rheum 54:1906-16.

Cutrone EC et al., "Identification of Critical Residues in Bovine IFNAR-1 Responsible for Interferon Binding*", (2001) J. Biol. Chem. 276:17140.

Al-Lazikani, B. et al., "Standard Conformations for the Canonical Structures of Immunoglobulins", J. Mol. Biol., 273(4), 927 (1997).

Chothia, C. et al., "Domain Association in Immunoglobulin Molecules The Packing of Variable Domains", J Mol Biol. Dec 5;186(3):651-63 (1985).

Chothia, C. and Lesk, A.M., "Canonical Structures for the Hypervariable Regions of Immunoglobulins", J.Mol.Biol., 196,901 (1987).

Chothia, C. et al., "Conformations of immunoglobulin hypervariable regions", Nature. Dec. 21-28;342(6252):877-83 (1989).

Marie-Paule Lefranc et al., "IMGT unique numbering for immunoglobulin and T cell receptor variable domains and Ig superfamily V-like domains", Developmental and Comparative Immunology, 27: 55-77 (2003).

(56) References Cited

OTHER PUBLICATIONS

Marie-Paule Lefranc et al., "IMGT, the international ImMunoGeneTics information system: a standardized approach for immunogenetics and immunoinformatics", Immunome Research, 1(3), (2005).
Huston JS et al., "Protein engineering of antibody binding sites: Recovery of specific activity in an anti-digoxin single-chain Fv analogue produced in *Escherichia coli*", Proc Natl Acad Sci USA, 85:5879(1988).
Riechmann L. and Muyldermans S., "Single domain antibodies: comparison of camel VH and camelised human VH domains", J Immunol Methods. Dec. 10;231(1-2):25-38 (1999).
Muyldermans S., "Single domain camel antibodies: current status", J Biotechnol. Jun.;74(4):277-302 (2001).
Hamers-Casterman C. et al., "Naturally occurring antibodies devoid of light chains", Nature. Jun. 3;363(6428):446-8 (1993).
Nguyen VK. et al., "Heavy-chain antibodies in Camelidae; a case of evolutionary innovation", Immunogenetics. Apr.;54(1):39-47 (2002).
Nguyen VK. et al., "Heavy-chain only antibodies derived from dromedary are secreted and displayed by mouse B cells", Immunology. May;109(1):93-101 (2003).
Koch-Nolte F. et al., "Single domain antibodies from llama effectively and specifically block T cell ecto-ADP-ribosyltransferase ART2.2 in vivo", Faseb J. Nov.;21(13):3490-8. Epub Jun. 15, 2007 (2007).
Holliger P. et al., "Diabodies": Small bivalent and bispecific antibody fragments, Proc Natl Acad Sci U S A. Jul. 15;90(14):6444-8 (1993).
NCBI Ref Seq No. NP_000620.2, "interferon alpha/beta receptor 1 isoform 2 precursor [*Homo sapiens*]".
NCBI Ref Seq No. NP_001253442.1, "interferon alpha/beta receptor 1 precursor [Macaca mulatta]".
NCBI Ref Seq No. XP_005548866.2, "PREDICTED: interferon alpha/beta receptor 1 isoform X1 [Macaca fascicularis]".
NCBI Ref Seq No. XP_015302385.1, "PREDICTED: interferon alpha/beta receptor 1 isoform X2 [Macaca fascicularis]".
NCBI Ref Seq No. XP_005548864.1, "PREDICTED: interferon alpha/beta receptor 1 isoform X3 [Macaca fascicularis]".
NCBI Ref Seq No. XP_005548865.1, "PREDICTED: interferon alpha/beta receptor 1 isoform X4 [Macaca fascicularis]".
Altschul S.F. et al., "Basic Local Alignment Search Tool", J. Mol. Biol., 215:403-410 (1990).
Stephen F. et al., "Gapped BLAST and PSI-BLAST: a new generation of protein database search programs", Nucleic Acids Res., 25:3389-3402 (1997).
Higgins D.G. et al., "Using CLUSTAL for Multiple Sequence Alignments", Methods in Enzymology, 266:383-402 (1996).
Larkin M.A. et al., "Clustal W and Clustal X version 2.0", Bioinformatics (Oxford, England), 23(21): 2947-8 (2007).
Wang et al., "Sindbis Virus Can Exploit a Host Antiviral Protein To Evade Immune Surveillance", J Virol. Oct. 28, 2016;90(22):10247-10258.
Pan et al., "Development and application of bioluminescence imaging for the influenza A virus", J Thorac Dis. Jul. 2018;10(Suppl 19):S2230-S2237.
Yao Y et al., "Development of Potential Pharmacodynamic and Diagnostic Markers for Anti-IFN-alpha Monoclonal Antibody Trials in Systemic Lupus Erythematosus", Hum Genomics Proteomics 2009.
Coelho LF et al., "Interferon-and-differentially regulate osteoclastogenesis: Role of differential induction of chemokine CXCL 11 expression", Proc Natl Acad Sci U S A. Aug. 16, 2005;102(33):11917-22.
De Weerd NA et al., "Structural basis of a unique interferon-beta signaling axis mediated via the receptor IFNAR1", Nat Immunol 14:901-7 (2013).
Jones et al., "Replacing the complementarity-determining regions in a human antibody with those from a mouse", (1986) Nature 321:522-525.
Riechmann et al., "Reshaping human antibodies for therapy", (1988) Nature 332:323-327.
Verhoeyen et al., "Reshaping Human Antibodies: Grafting an Antilysozyme Activity" (1988) Science 239:1534-1536.
Sims et al., "A humanized CD18 antibody can block function without cell destruction", (1993) J. Immunol. 151:2296.
Chothia et al., "Canonical Structures for the Hypervariable Regions of Immunoglobulins", (1987) J. Mot. Biol. 196:901.
Carter et al., "Humanization of an anti-p185HER2 antibody for human cancer therapy", (1992) Proc. Natl. Acad. Sci. USA, 89:4285.
Presta et al., "Humanization of an Antibody Directed Against IgE", (1993) J. Immunol., 151:2623.
Winter et al., "Making Antibodies by Phage Display Technology", Ann. Rev Immunol., 12: 433-455 (1994).
Cunningham and Wells, "High-Resolution Epitope Mapping of hGH-Receptor Interactions by Alanine-Scanning Mutagenesis", (1989) Science, 244:1081-1085.
Shields RL. et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R", J Biol Chem. 2001. 276(9): 6591-604.
Idusogie EE. et al., "Mapping of the C1q Binding Site on Rituxan, a Chimeric Antibody with a Human IgG1 Fc", J Immunol. 2000. 164(8):4178-84.
Steurer W. et al., "Ex vivo coating of islet cell allografts with murine CTLA4/Fc promotes graft tolerance", J Immunol. 1995, 155(3): 1165-74.
Idusogie EE. et al., "Engineered Antibodies with Increased Activity to Recruit Complement", J Immunol. 2001, 166(4):2571-5.
Lazar GA. et al., "Engineered antibody Fc variants with enhanced effector function", PNAS, 2006, 103(11): 4005-4010.
Ryan MC. et al., "Antibody targeting of B-cell maturation antigen on malignant plasma cells", Mol. Cancer Ther., 2007, 6: 3009-3018.
Richards JO,. et al., "Optimization of antibody binding to Fc gamma RIIa enhances macrophage phagocytosis of tumor cells", Mol Cancer Ther. 2008, 7(8): 2517-27.
Shields R. L. et al., "Lack of Fucose on Human IgG1 N-Linked Oligosaccharide Improves Binding to Human Fc gamma RIII and Antibody-dependent Cellular Toxicity*", J. Biol. Chem, 2002, 277: 26733-26740.

* cited by examiner

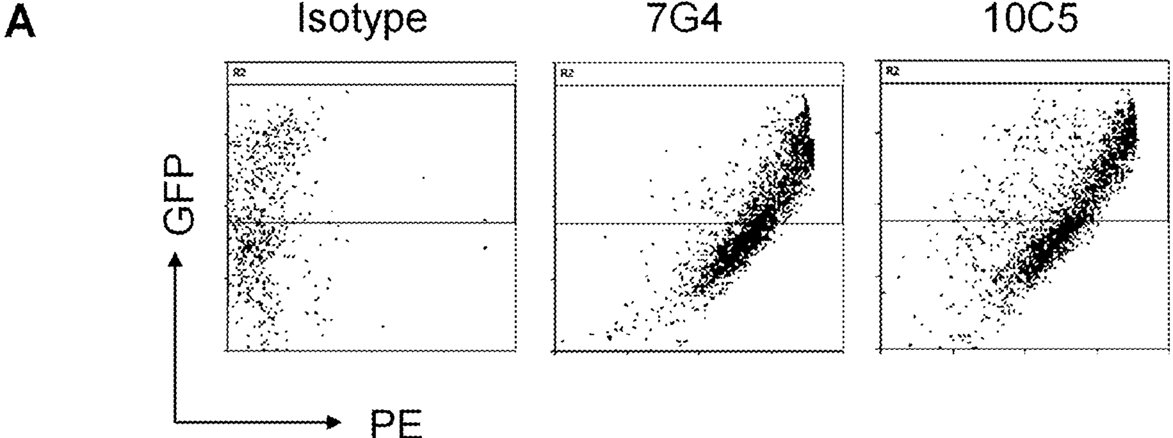
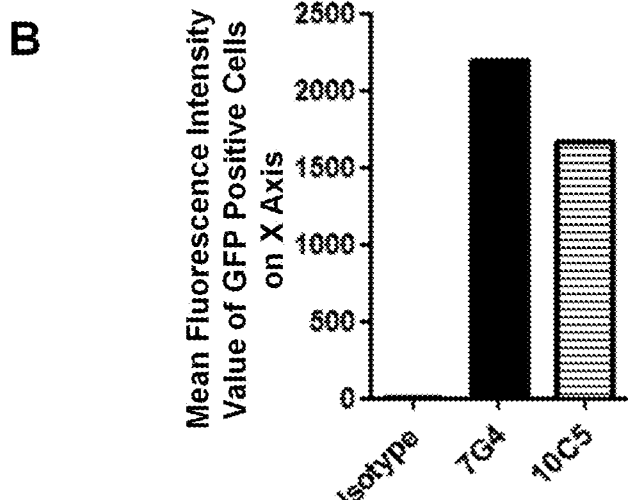
Figure 1

A

| Description | Graphical View | 7G4 | 10C5 |
|---|---|---|---|
| 1. IFNAR1-aa1-557 | | + | + |
| 2. IFNAR1-Δaa32-126 | | + | + |
| 3. IFNAR1-Δaa127-227 | | - | - |
| 4. IFNAR1-Δaa231-329 | | - | - |
| 5. IFNAR1-Δaa331-432 | | + | + |
| 6. IFNAR1-Δaa32-126, Δaa331-432 | | + | + |
| 7. IFNAR1-Δaa231-432 | | - | - |
| 8. IFNAR1-Δaa32-227 | | - | - |

B

Percentage of PE positive cells (%)

100
80
60
40
20
0

1 2 3 4 5 6 7 8 1 2 3 4 5 6 7 8 1 2 3 4 5 6 7 8

Isotype
7G4
10C5

Figure 2

Sequence of 7G4-H

```
      Q   V   Q   L   Q   Q   P   G   A   E   L   V   K   P   G   A   P   V   K   L
1     CAG GTC CAA CTG CAG CAG CCT GGG GCT GAG CTT GTG AAG CCT GGG GCT CCA GTG AAA CTG
                                                   CDR1
      S   C   K   A   S   G   Y   T   F   T   S   Y   W   M   N   W   V   R   Q   R
61    TCC TGC AAG GCT TCT GGC TAC ACC TTC ACC AGC TAC TGG ATG AAC TGG GTG AGG CAG AGG
                                                               CDR2
      P   G   R   G   L   E   W   I   G   K   I   D   P   S   D   S   E   T   H   F
121   CCT GGA CGA GGC CTC GAG TGG ATT GGA AAG ATT GAT CCT TCC GAT AGT GAA ACT CAC TTC

      N   Q   K   F   R   D   K   A   T   L   T   V   D   K   S   S   T   T   A   Y
181   AAT CAA AAG TTC AGG GAC AAG GCC ACA CTG ACT GTA GAC AAA TCC TCC ACC ACA GCC TAC

      I   Q   L   S   S   L   T   S   E   D   S   A   V   Y   Y   C   A   R   G   G
241   ATC CAA CTC AGC AGC CTG ACA TCT GAG GAC TCT GCG GTC TAT TAC TGT GCA AGA GGG GGG
                          CDR3
      R   I   S   F   D   Y   D   A   A   L   D   Y   W   G   Q   G   T   S   V   T
301   AGG ATC TCC TTT GAT TAC GAC GCT GCT TTG GAC TAC TGG GGT CAA GGA ACC TCA GTC ACC

      V   S   S
361   GTA TCC TCA
```

Figure 6

Sequence of 7G4-L

```
        D   I   L   M   T   Q   S   S   S   S   F   S   V   S   L   G   D   R   V   T
1      GAC ATC CTG ATG ACA CAG TCT TCA TCC TCC TTT TCT GTA TCT TTA GGA GAC AGA GTC ACC
                                     CDR1
        I   T   C   K   S   S   E   V   I   Y   N   R   L   A   W   F   Q   Q   K   P
61     ATT ACT TGC AAA TCA AGT GAG GTC ATA TAT AAT CGG TTA GCC TGG TTT CAG CAG AAA CCA
                                                         CDR2
        G   N   A   P   R   L   L   I   S   G   A   T   T   L   E   S   G   F   P   S
121    GGA AAT GCT CCT AGG CTC TTA ATA TCT GGT GCG ACC ACT TTG GAA TCT GGG TTT CCT TCA

        R   F   S   G   S   G   S   G   K   D   Y   T   L   S   I   T   S   L   Q   I
181    AGA TTC AGT GGC AGT GGA TCT GGA AAG GAT TAC ACT CTC AGC ATT ACC AGT CTT CAG ATT
                                                        CDR3
        E   D   V   S   T   Y   Y   C   Q   Q   Y   W   N   K   P   F   T   F   G   S
241    GAA GAT GTT TCT ACT TAT TAC TGT CAA CAG TAT TGG AAT AAG CCA TTC ACG TTC GGC TCG

        G   T   K   L   E   V   K
301    GGG ACA AAG TTG GAA GTA AAA
```

Figure 7

Sequence of 10C5-H

```
     Q   V   Q   L   Q   Q   P   G   T   E   L   V   K   P   G   S   P   V   K   L
1    CAG GTC CAA CTA CAG CAG CCT GGG ACT GAG CTT GTG AAG CCT GGG TCT CCA GTG AAA CTG
                                             CDR1
     S   C   K   A   S   G   Y   T   F   T   S   F   W   L   N   W   V   Q   Q   R
61   TCC TGC AAG GCT TCT GGC TAC ACC TTC ACC AGC TTC TGG TTG AAC TGG GTG CAA CAG AGG
                                                                 CDR2
     P   G   R   G   L   E   W   I   G   K   I   D   P   S   D   S   E   I   R   Y
121  CCT GGA CGA GGC CTC GAA TGG ATT GGA AAG ATT GAT CCT TCC GAT AGT GAA ATT CGC TAC

     N   Q   K   F   K   D   K   A   T   L   T   V   D   K   S   S   N   T   A   Y
181  AAT CAA AAG TTC AAG GAC AAG GCC ACA CTG ACT GTA GAC AAA TCG TCC AAC ACA GCC TAC

     I   Q   L   S   S   L   T   S   E   D   S   A   V   Y   Y   C   A   R   G   G
241  ATC CAA CTC AGC AGC CTG ACA TCT GAG GAC TCT GCG GTC TAT TAC TGT GCA AGA GGG GGG
                         CDR3
     G   I   Y   Y   D   Y   D   G   A   M   D   Y   W   G   Q   G   T   S   V   T
301  GGG ATC TAC TAT GAT TAC GAC GGC GCT ATG GAC TAC TGG GGT CAA GGA ACC TCA GTC ACC

     V   S   S
361  GTA TCC TCA
```

Figure 8

Sequence of 10C5-L

```
     D   I   Q   M   T   Q   S   S   S   S   F   S   V   S   L   G   D   R   L   T
1    GAC ATC CAG ATG ACA CAA TCT TCA TCC TCC TTT TCT GTA TCT CTA GGA GAC AGA CTC ACC
                             CDR1
     I   T   C   K   A   S   E   V   I   Y   N   R   L   A   W   F   Q   Q   K   P
61   ATT ACT TGC AAG GCA AGT GAG GTC ATA TAT AAT CGA TTA GCC TGG TTT CAG CAG AAA CCA
                                                   CDR2
     G   N   A   P   R   L   L   I   S   G   A   T   S   L   E   T   G   V   P   S
121  GGA AAT GCT CCT AGG CTC TTA ATA TCT GGT GCA ACC AGT TTG GAA ACT GGG GTG CCT TCA

     R   F   S   G   S   G   S   R   K   D   Y   T   L   S   I   S   S   L   Q   T
181  AGA TTC AGT GGC AGT GGA TCT AGA AAG GAT TAC ACT CTC AGC ATT TCC AGT CTT CAG ACT
                                                   CDR3
     E   D   V   A   T   Y   Y   C   Q   Q   Y   W   S   S   P   F   T   F   G   S
241  GAA GAT GTT GCT ACT TAT TAC TGT CAA CAG TAT TGG AGT TCT CCA TTC ACG TTC GGC TCG

     G   T   K   L   E   I   K
301  GGG ACA AAG TTG GAA ATA AAA
```

Figure 9

```
                                                                    Section 1
                          (1)  1        10        20        30          43
  10C5 heavy chain VDJ    (1)  QVQLQQPGTELVKPGSPVKLSCKASGYTFTSFWLNWVQQRPGR
  7G4 heavy chain VDJ     (1)  QVQLQQPGAELVKPGAPVKLSCKASGYTFTSYWMNWVRQRPGR
  IGHV1-69 IGHD2-4 IGHJ4  (1)  QVQLQQPGAELVMPGASVKLSCKASGYTFTSYWMHWVKQRPGQ
  Consensus               (1)  QVQLQQPGAELVKPGAPVKLSCKASGYTFTSYWMNWVKQRPGR
                                                                    Section 2
                          (44) 44    50        60        70             86
  10C5 heavy chain VDJ    (44) GLEWIGKIDPSDSEIRYNQKFKDKATLTVDKSSNTAYIQLSSL   SEQ ID NO:9
  7G4 heavy chain VDJ     (44) GLEWIGKIDPSDSETHFNQKFRDKATLTVDKSSTTAYIQLSSL   SEQ ID NO:7
  IGHV1-69 IGHD2-4 IGHJ4  (44) GLEWIGEIDPSDSYTNYNQKFKGKSTLTVDKSSSTAYMQLSSL   SEQ ID NO:15
  Consensus               (44) GLEWIGKIDPSDSET YNQKFKDKATLTVDKSSSTAYIQLSSL
                                                                    Section 3
                          (87) 87           100       110         123
  10C5 heavy chain VDJ    (87) TSEDSAVYYCARGGGIYYDYDGAMDYWGQGTSVTVSS         SEQ ID NO:9
  7G4 heavy chain VDJ     (87) TSEDSAVYYCARGGRISFDYDAALDYWGQGTSVTVSS         SEQ ID NO:7
  IGHV1-69 IGHD2-4 IGHJ4  (87) TSEDSAVYYCARSTMITY---YAMDYWGQGTSVTVSS         SEQ ID NO:15
  Consensus               (87) TSEDSAVYYCARGG ISYDYDAAMDYWGQGTSVTVSS

                                                                              SEQ ID NO:9
                                                                              SEQ ID NO:7
                                                                              SEQ ID NO:15
```

Figure 10

Section 1

| | | 1 ... 10 ... 20 ... 30 ... 40 ... 50 | |
|---|---|---|---|
| 10C5 light chain VJ | (1) | DIQMTQSSSSFSVSLGDRITITCKASEVIYNRLAWFQQKPGNAPRLLISG | SEQ ID NO:10 |
| 7G4 light chain VJ | (1) | DILMTQSSSSFSVSLGDRVTITCKSSEVIYNRLAWFQQKPGNAPRLLISG | SEQ ID NO:8 |
| IGKV13-84 IGKJ4 | (1) | DIQMTQSSSSFSVSLGDRVTITCKASEDIYNRLAWYQQKPGNAPRLLISG | SEQ ID NO:16 |
| Consensus | (1) | DIQMTQSSSSFSVSLGDRVTITCKASEVIYNRLAWFQQKPGNAPRLLISG | |

Section 2

| | | 51 ... 60 ... 70 ... 80 ... 90 ... 100 | |
|---|---|---|---|
| 10C5 light chain VJ | (51) | ATSLETGVPSRFSGSGSRKDYTLSINSLQTEDVATYYCQQYWSRPFTFGS | SEQ ID NO:10 |
| 7G4 light chain VJ | (51) | ATTLESGFPSRFSGSGSGKDYTLSITSLQIEDVSTYYCQQYWNKPFTFGS | SEQ ID NO:8 |
| IGKV13-84 IGKJ4 | (51) | ATSLETGVPSRFSGSGSGKDYTLSITSLQTEDVATYYCQQYWSTPFTFGS | SEQ ID NO:16 |
| Consensus | (51) | ATSLETGVPSRFSGSGSGKDYTLSITSLQTEDVATYYCQQYWSSPFTFGS | |

Section 3

| | | 101 ... 107 | |
|---|---|---|---|
| 10C5 light chain VJ | (101) | GTKLEIK | SEQ ID NO:10 |
| 7G4 light chain VJ | (101) | GTKLEVK | SEQ ID NO:8 |
| IGKV13-84 IGKJ4 | (101) | GTKLEIK | SEQ ID NO:16 |
| Consensus | (101) | GTKLEIK | |

Figure 11

| | Top | EC50 |
|---|---|---|
| Hu4-6 | 3.355 | 0.003321 |
| Hu4-13 | 3.395 | 0.003273 |
| Hu4-14 | 3.099 | 0.002266 |
| Hu4-15 | 3.462 | 0.002839 |
| Hu4-16 | 3.307 | 0.003149 |
| Chimeric | 3.272 | 0.004647 |

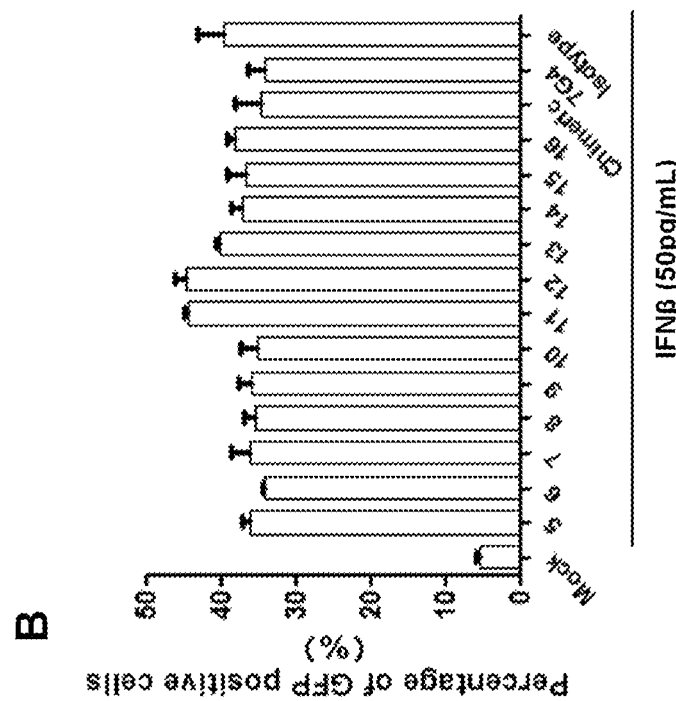
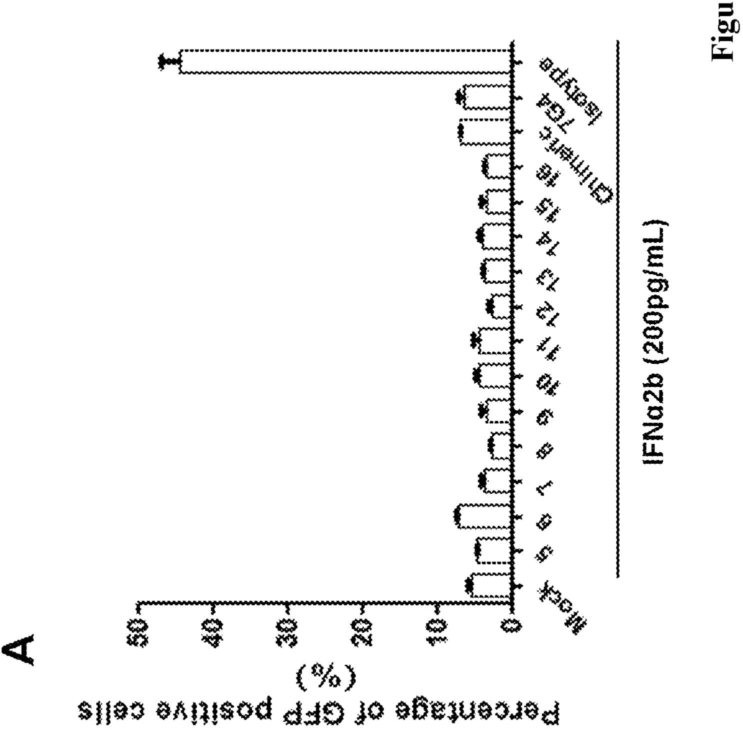
Figure 13

| SEQ ID NO | Sequence type | Sequences |
|---|---|---|
| 1 | Amino acid | $SX_1$(Y/F)$WX_{19}$(M/L)N |
| 2 | Amino acid | $KIDPSDSEX_2$(T/I)$X_{20}$(H/R)$X_{21}$(F/Y)$NQKFX_{22}$(R/K)D |
| 3 | Amino acid | $GGX_3$(R/G)$IX_4$(S/Y)$X_5$(F/Y)$DYDX_6$(A/G)$AX_7$(L/M)D Y |
| 4 | Amino acid | $KX_{23}$(S/A)SEVIYNRLA |
| 5 | Amino acid | $GATX_{24}$(T/S)$LEX_{25}$(S/T) |
| 6 | Amino acid | $QQYWX_8$(N/S)$X_9$(K/S)PFT |
| 7 | Amino acid | QVQLQQPGAELVKPGAPVKLSCKASGYTFTSYW MNWVRQRPGRGLEWIGKIDPSDSETHFNQKFRD KATLTVDKSSTTAYIQLSSLTSEDSAVYYCARGG RISFDYDAALDYWGQGTSVTVSS |
| 8 | Amino acid | DILMTQSSSSFSVSLGDRVTITCKSSEVIYNRLAW FQQKPGNAPRLLISGATTLESGFPSRFSGSGSGKD YTLSITSLQIEDVSTYYCQQYWNKPFTFGSGTKLE VK |
| 9 | Amino acid | QVQLQQPGTELVKPGSPVKLSCKASGYTFTSFWL NWVQQRPGRGLEWIGKIDPSDSEIRYNQKFKDK ATLTVDKSSNTAYIQLSSLTSEDSAVYYCARGGG IYYDYDGAMDYWGQGTSVTVSS |
| 10 | Amino acid | DIQMTQSSSSFSVSLGDRLTITCKASEVIYNRLAW FQQKPGNAPRLLISGATSLETGVPSRFSGSGSRKD YTLSISSLQTEDVATYYCQQYWSSPFTFGSGTKLE IK |
| 11 | Nucleotide | CAGGTCCAACTGCAGCAGCCTGGGGCTGAGCT TGTGAAGCCTGGGGCTCCAGTGAAACTGTCCT GCAAGGCTTCTGGCTACACCTTCACCAGCTACT GGATGAACTGGGTGAGGCAGAGGCCTGGACGA GGCCTCGAGTGGATTGGAAAGATTGATCCTTCC GATAGTGAAACTCACTTCAATCAAAAGTTCAG GGACAAGGCCACACTGACTGTAGACAAATCCT CCACCACAGCCTACATCCAACTCAGCAGCCTG ACATCTGAGGACTCTGCGGTCTATTACTGTGCA AGAGGGGGGAGGATCTCCTTTGATTACGACGC TGCTTTGGACTACTGGGGTCAAGGAACCTCAGT CACCGTATCCTCA |
| 12 | Nucleotide | GACATCCTGATGACACAGTCTTCATCCTCCTTT TCTGTATCTTTAGGAGACAGAGTCACCATTACT TGCAAATCAAGTGAGGTCATATATAATCGGTT AGCCTGGTTTCAGCAGAAACCAGGAAATGCTC CTAGGCTCTTAATATCTGGTGCGACCACTTTGG AATCTGGGTTTCCTTCAAGATTCAGTGGCAGTG GATCTGGAAAGGATTACACTCTCAGCATTACC AGTCTTCAGATTGAAGATGTTTCTACTTATTAC TGTCAACAGTATTGGAATAAGCCATTCACGTTC GGCTCGGGGACAAAGTTGGAAGTAAAA |
| 13 | Nucleotide | CAGGTCCAACTACAGCAGCCTGGGACTGAGCT TGTGAAGCCTGGGTCTCCAGTGAAACTGTCCTG CAAGGCTTCTGGCTACACCTTCACCAGCTTCTG GTTGAACTGGGTGCAACAGAGGCCTGGACGAG |

Figure 16

| | | |
|---|---|---|
| | | GCCTCGAATGGATTGGAAAGATTGATCCTTCCG ATAGTGAAATTCGCTACAATCAAAAGTTCAAG GACAAGGCCACACTGACTGTAGACAAATCGTC CAACACAGCCTACATCCAACTCAGCAGCCTGA CATCTGAGGACTCTGCGGTCTATTACTGTGCAA GAGGGGGGGGATCTACTATGATTACGACGGC GCTATGGACTACTGGGGTCAAGGAACCTCAGT CACCGTATCCTCA |
| 14 | Nucleotide | GACATCCAGATGACACAATCTTCATCCTCCTTT TCTGTATCTCTAGGAGACAGACTCACCATTACT TGCAAGGCAAGTGAGGTCATATATAATCGATT AGCCTGGTTTCAGCAGAAACCAGGAAATGCTC CTAGGCTCTTAATATCTGGTGCAACCAGTTTGG AAACTGGGGTGCCTTCAAGATTCAGTGGCAGT GGATCTAGAAAGGATTACACTCTCAGCATTTCC AGTCTTCAGACTGAAGATGTTGCTACTTATTAC TGTCAACAGTATTGGAGTTCTCCATTCACGTTC GGCTCGGGGACAAAGTTGGAAATAAAA |
| 15 | Amino acid | QVQLQQPGAELVMPGASVKLSCKASGYTFTSYW MHWVKQRPGQGLEWIGEIDPSDSYTNYNQKFKG KSTLTVDKSSSTAYMQLSSLTSEDSAVYYCARST MITYYAMDYWGQGTSVTVSS |
| 16 | Amino acid | DIQMTQSSSSFSVSLGDRVTITCKASEDIYNRLAW YQQKPGNAPRLLISGATSLETGVPSRFSGSGSGK DYTLSITSLQTEDVATYYCQQYWSTPFTFGSGTK LEIK |
| 17 | Amino acid | SPQKVEVDIIDDNFILRWNRSDESVGNVTFSFDY QKTGMDNWIKLSGCQNITSTKCNFSSLKLNVYEE IKLRIRAEKENTSSWYEVDSFTPFRKA |
| 18 | Amino acid | QIGPPEVHLEAEDKAIVIHISPGTKDSVMWALDG LSFTYSLVIWKNSSGVEERIENIYSRHKIYKLSPET TYCLKVKAALLTSWKIGVYSPVHCIKTTVEN |
| 19 | Amino acid | PPENIEVSVQNQNYVLKWDYTYANMTFQVQWL HAFLKRNPGNHLYKWKQIPDCENVKTTQCVFPQ NVFQKGIYLLRVQASDGNNTSFWSEEIKFDTEIQ |
| 20 | Amino acid | FLLPPVFNIRSLSDSFHIYIGAPKQSGNTPVIQDYP LIYEIIFWENTSNAERKIIEKKTDVTVPNLKPLTVY CVKARAHTMDEKLNKSSVFSDAVCEKTKPG |
| 21 | Amino acid | SYWMN |
| 22 | Amino acid | KIDPSDSETHFNQKFRD |
| 23 | Amino acid | GGRISFDYDAALDY |
| 24 | Amino acid | QQYWNKPFT |
| 25 | Amino acid | SFWLN |
| 26 | Amino acid | KIDPSDSEIRYNQKFKD |
| 27 | Amino acid | GGGIYYDYDGAMDY |
| 28 | Amino acid | QQYWSSPFT |
| 29 | Nucleotide | SARGTNMAGCTGSAGSAGTC |
| 30 | Nucleotide | CTTGACCAGGCATCCTAGAGTCA |
| 31 | Nucleotide | GAYATTGTGMTSACMCARWCTMCA |

Figure 16 (Continued)

| | | |
|---|---|---|
| 32 | Nucleotide | GGATACAGTTGGTGCAGCATC |
| 33 | Amino acid | QVQLVQSGAEVKKPGASVKVSCKASGYTFT |
| 34 | Amino acid | WVRQ$X_{10}$(A/R)PGQGLEW$X_{11}$(M/I)G |
| 35 | Amino acid | RVT$X_{12}$(M/L)T$X_{13}$(R/V)D$X_{14}$(T/K)STSTVYMELSSL RSEDTAVYYCAR |
| 36 | Amino acid | WGQGTLVTVSS |
| 37 | Amino acid | DIQMTQSPSSLSASVGDRVTITC |
| 38 | Amino acid | WYQQKPG$X_{15}$(K/N)APKLLI$X_{16}$(Y/S) |
| 39 | Amino acid | GVPSRFSGSGSG$X_{17}$(T/K)D$X_{18}$(F/Y)TLTISSLQPED FATYYC |
| 40 | Amino acid | FGQGTKLEIK |
| 41 | Amino acid | WVRQAPGQGLEWMG |
| 42 | Amino acid | WVRQAPGQGLEWIG |
| 43 | Amino acid | WVRQRPGQGLEWIG |
| 44 | Amino acid | RVTMTRDTSTSTVYMELSSLRSEDTAVYYCAR |
| 45 | Amino acid | RVTLTVDKSTSTVYMELSSLRSEDTAVYYCAR |
| 46 | Amino acid | WYQQKPGKAPKLLIY |
| 47 | Amino acid | WYQQKPGKAPKLLIS |
| 48 | Amino acid | WYQQKPGNAPKLLIS |
| 49 | Amino acid | GVPSRFSGSGSGTDFTLTISSLQPEDFATYYC |
| 50 | Amino acid | GVPSRFSGSGSGKDYTLTISSLQPEDFATYYC |
| 51 | Amino acid | QVQLVQSGAEVKKPGASVKVSCKASGYTFTSYW MNWVRQAPGQGLEWMGKIDPSDSETHFNQKFR DRVTMTRDTSTSTVYMELSSLRSEDTAVYYCAR GGRISFDYDAALDYWGQGTLVTVSS |
| 52 | Amino acid | QVQLVQSGAEVKKPGASVKVSCKASGYTFTSYW MNWVRQAPGQGLEWMGKIDPSDSETHFNQKFR DRVTLTVDKSTSTVYMELSSLRSEDTAVYYCAR GGRISFDYDAALDYWGQGTLVTVSS |
| 53 | Amino acid | QVQLVQSGAEVKKPGASVKVSCKASGYTFTSYW MNWVRQAPGQGLEWIGKIDPSDSETHFNQKFRD RVTLTVDKSTSTVYMELSSLRSEDTAVYYCARG GRISFDYDAALDYWGQGTLVTVSS |
| 54 | Amino acid | QVQLVQSGAEVKKPGASVKVSCKASGYTFTSYW MNWVRQRPGQGLEWIGKIDPSDSETHFNQKFRD RVTLTVDKSTSTVYMELSSLRSEDTAVYYCARG GRISFDYDAALDYWGQGTLVTVSS |
| 55 | Amino acid | DIQMTQSPSSLSASVGDRVTITCKSSEVIYNRLAW YQQKPGKAPKLLIYGATTLESGVPSRFSGSGSGT DFTLTISSLQPEDFATYYCQQYWNKPFTFGQGTK LEIK |
| 56 | Amino acid | DIQMTQSPSSLSASVGDRVTITCKSSEVIYNRLAW YQQKPGKAPKLLIYGATTLESGVPSRFSGSGSGK DYTLTISSLQPEDFATYYCQQYWNKPFTFGQGTK LEIK |
| 57 | Amino acid | DIQMTQSPSSLSASVGDRVTITCKSSEVIYNRLAW YQQKPGKAPKLLISGATTLESGVPSRFSGSGSGK DYTLTISSLQPEDFATYYCQQYWNKPFTFGQGTK LEIK |

Figure 16 (Continued)

| | | |
|---|---|---|
| 58 | Amino acid | DIQMTQSPSSLSASVGDRVTITCKSSEVIYNRLAWYQQKPGNAPKLLISGATTLESGVPSRFSGSGSGKDYTLTISSLQPEDFATYYCQQYWNKPFTFGQGTKLEIK |
| 59 | Amino acid | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGGRISFDYDAALDYWGQGTLVTVSS |
| 60 | Amino acid | DIQMTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKLEIK |
| 61 | Amino acid | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 62 | Amino acid | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 63 | Amino acid | GTKDSVMWALDGLSFTYSLVIWKNSSGVEERIENIYSRHKIYKLSPETTYCLKVKAALLTSWKIGV |
| 64 | Amino acid | PGQDGNMWALEKPSFSYTIRIWQKSSSDKKTINSTYYVEKIPELLPETTYCLEVKAIHPSLKKHSN |
| 65 | Amino acid | GGRISFDYDGALDY |
| 66 | Amino acid | GATSLET |
| 67 | Amino acid | QVQLVQSGAEVKKPGASVKVSCKASGYTFTSYWMNWVRQAPGQGLEWMGKIDPSDSETHFNQKFRDRVTLTVDKSTSTVYMELSSLRSEDTAVYYCARGGRISFDYDGALDYWGQGTLVTVSS |
| 68 | Amino acid | DIQMTQSPSSLSASVGDRVTITCKSSEVIYNRLAWYQQKPGKAPKLLIYGATSLETGVPSRFSGSGSGKDYTLTISSLQPEDFATYYCQQYWNKPFTFGQGTKLEIK |
| 69 | Amino acid | MMVVLLGATTLVLVAVAPWVLSAAAGGKNLKSPQKVEVDIIDDNFILRWNRSDESVGNVTFSFDYQKTGMDNWIKLSGCQNITSTKCNFSSLKLNVYEEIKLRIRAEKENTSSWYEVDSFTPFRKAQIGPPEVHL |

Figure 16 (Continued)

| | | |
|---|---|---|
| | | EAEDKAIVIHISPPGQDGNMWALEKPSFSYTIRIW QKSSSDKKTINSTYYVEKIPELLPETTYCLEVKAI HPSLKKHSNYSPVHCIKTTVENELPPPENIEVSVQ NQNYVLKWDYTYANMTFQVQWLHAFLKRNPG NHLYKWKQIPDCENVKTTQCVFPQNVFQKGIYL LRVQASDGNNTSFWSEEIKFDTEIQAFLLPPVFNI RSLSDSFHIYIGAPKQSGNTPVIQDYPLIYEIIFWE NTSNAERKIIEKKTDVTVPNLKPLTVYCVKARAH TMDEKLNKSSVFSDAVCEKTKPGNTSKIWLIVGI CIALFALPFVIYAAKVFLRCINYVFFPSLKPSSSID EYFSEQPLKNLLLSTSEEQIEKCFIIENISTIATVEE TNQTDEDHKKYSSQTSQDSGNYSNEDESESKTSE ELQQDFV |
| 70 | Amino acid | KSSEVIYNRLA |
| 71 | Amino acid | GATTLES |
| 72 | Amino acid | KASEVIYNRLA |

Figure 16 (Continued)

ANTI-IFNAR1 ANTIBODIES

FIELD OF THE INVENTION

The present disclosure generally relates to novel anti-IFNAR1 antibodies.

BACKGROUND

Type I interferons (IFN-Is) include a large family of cytokines with antiviral, immunomodulatory and anti-proliferative activities. The IFN-I family consists of 5 closely related members including IFNα, IFNβ, IFNε, IFNκ and IFNω. IFNβ exhibits much greater potency than IFNα or IFNω at inhibiting monocyte differentiation, inhibiting viral replication, inducing apoptosis of human tumoral cells and the like (Schreiber G, et al. (2015) Trends Immunol 36:139-49). On the other hand, IFNβ has minimal involvement in some IFN-I related disease pathogenesis, and this distinguishes IFNβ from IFNα and IFNω (Slavikova M et al. (2003) J Interferon Cytokine Res 23:143-147, Hua J, et al. (2006) Arthritis Rheum 54:1906-16.).

All IFN-I signal through a heterodimeric receptor known as the IFN-α receptor (IFNAR) that consists of IFNAR1 and IFNAR2 chains. IFNAR1 is essential for high affinity binding and differential specificity of the IFNAR complex (Cutrone E C et al. (2001) J. Biol. Chem. 276:17140).

Needs remain for novel anti-IFNAR1 antibodies.

SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides anti-IFNAR1 antibodies (e.g. anti-human IFNAR1) or antigen-binding fragments thereof, isolated polynucleotides encoding the same, pharmaceutical compositions comprising the same, and the uses thereof.

In one aspect, the present disclosure provides an antibody or antigen-binding fragment thereof comprising heavy chain HCDR1, HCDR2 and HCDR3, and/or light chain LCDR1, LCDR2 and LCDR3, wherein the HCDR1 comprises $SX_1WX_{19}N$ (SEQ ID NO:1) or a homologous sequence of at least 75% (e.g. at least 75%, at least 80%, at least 85%) sequence identity thereof, the HCDR2 comprises $KIDPSDSEX_2X_{20}X_{21}NQKFX_{22}D$ (SEQ ID NO: 2) or a homologous sequence of at least 75% (e.g. at least 75%, at least 80%, at least 85%) sequence identity thereof, the HCDR3 comprises $GGX_3IX_4X_5DYDX_6AX_7DY$ (SEQ ID NO:3) or a homologous sequence of at least 60% (e.g. at least 60%, at least 65%, at least 70%, at least 75%, at least 80%, at least 85%, at least 90%, at least 93%) sequence identity thereof, the LCDR1 comprises $KX_{23}SEVIYNRLA$ (SEQ ID NO:4) or a homologous sequence of at least 80% (e.g. at least 80%, at least 84%) sequence identity thereof, the LCDR2 comprises $GATX_{24}LEX_{25}$ (SEQ ID NO:5) or a homologous sequence of at least 65% sequence identity thereof, the LCDR3 comprises $QQYWX_8X_9PFT$ (SEQ ID NO:6) or a homologous sequence of at least 65% (e.g. at least 65%, at least 70%, at least 75%, at least 80%, at least 85%) sequence identity thereof, wherein $X_1$ is Y or F, $X_2$ is T or I, $X_3$ is R or G, $X_4$ is S or Y, $X_5$ is F or Y, $X_6$ is A or G, $X_7$ is L or M, $X_8$ is N or S, $X_9$ is K or S, $X_{19}$ is M or L, $X_{20}$ is H or R, $X_{21}$ is F or Y, $X_{22}$ is R or K, $X_{23}$ is S or A, $X_{24}$ is T or S, $X_{25}$ is S or T, and wherein the antibody or antigen-binding fragment thereof is capable of specifically binding to IFNAR1, for example, human IFNAR1.

In certain embodiments, the antibody or antigen-binding fragment thereof provided herein comprises an HCDR1 having no more than 3, 2, or 1 amino acid substitutions in SEQ ID NO: 1, an HCDR2 having no more than 6, 5, 4, 3, 2, or 1 amino acid substitutions in SEQ ID NO: 2, HCDR3 having no more than 6, 5, 4, 3, 2, or 1 amino acid substitutions in SEQ ID NO: 3, LCDR1 having no more than 2 or 1 amino acid substitution in SEQ ID NO: 4, LCDR2 having no more than 3, 2, or 1 amino acid substitution in SEQ ID NO: 5, and/or LCDR3 having no more than 3, 2, or 1 amino acid substitutions in SEQ ID NO: 6.

In certain embodiments, the antibody or antigen-binding fragment thereof comprises a heavy chain HCDR1 comprising the sequence selected from SEQ ID NOs: 21 and 25, a heavy chain HCDR2 comprising the sequence selected from SEQ ID NOs: 22 and 26, and a heavy chain HCDR3 comprising the sequence selected from SEQ ID NOs: 23, 27 and 65.

In certain embodiments, the antibody or antigen-binding fragment thereof comprises a light chain LCDR1 comprising the sequence selected from SEQ ID NO: 70 and 72, a light chain LCDR2 comprising the sequence selected from SEQ ID NO: 71 and 66, and a light chain LCDR3 comprising the sequence selected from SEQ ID NOs: 24 and 28.

In certain embodiments, the heavy chain HCDR1, HCDR2, and HCDR3 are selected from: a) the HCDR1 comprising the sequence of SEQ ID NO:21, the HCDR2 comprising the sequence of SEQ ID NO:22, and the HCDR3 comprising the sequence of SEQ ID NO:23; b) the HCDR1 comprising the sequence of SEQ ID NO:25, the HCDR2 comprising the sequence of SEQ ID NO:26, and the HCDR3 comprising the sequence of SEQ ID NO:27; and c) the HCDR1 comprising the sequence of SEQ ID NO:21, the HCDR2 comprising the sequence of SEQ ID NO:22, and the HCDR3 comprising the sequence of SEQ ID NO:65.

In certain embodiments, the light chain LCDR1, LCDR2, and LCDR3 are selected from: a) the LCDR1 comprising the sequence of SEQ ID NO:70, the LCDR2 comprising the sequence of SEQ ID NO:71, and the LCDR3 comprising the sequence of SEQ ID NO:24; b) the LCDR1 comprising the sequence of SEQ ID NO:72, the LCDR2 comprising the sequence of SEQ ID NO:66, and the LCDR3 comprising the sequence of SEQ ID NO:28; and c) the LCDR1 comprising the sequence of SEQ ID NO:70, the LCDR2 comprising the sequence of SEQ ID NO:66, and the LCDR3 comprising the sequence of SEQ ID NO:24.

In certain embodiments, the antibody or antigen-binding fragment thereof comprises: a) the HCDR1 comprising the sequence of SEQ ID NO:21, the HCDR2 comprising the sequence of SEQ ID NO:22, the HCDR3 comprising the sequence of SEQ ID NO: 23, the LCDR1 comprising the sequence of SEQ ID NO:70, the LCDR2 comprising the sequence of SEQ ID NO:71, and the LCDR3 comprising the sequence of SEQ ID NO:24; b) the HCDR1 comprising the sequence of SEQ ID NO:25, the HCDR2 comprising the sequence of SEQ ID NO:26, the HCDR3 comprising the sequence of SEQ ID NO:27, the LCDR1 comprising the sequence of SEQ ID NO:72, the LCDR2 comprising the sequence of SEQ ID NO:66, and the LCDR3 comprising the sequence of SEQ ID NO:28; c) the HCDR1 comprising the sequence of SEQ ID NO:21, the HCDR2 comprising the sequence of SEQ ID NO: 22, the HCDR3 comprising the sequence of SEQ ID NO:65, the LCDR1 comprising the sequence of SEQ ID NO:70, the LCDR2 comprising the sequence of SEQ ID NO:71, and the LCDR3 comprising the sequence of SEQ ID NO:24; d) the HCDR1 comprising the sequence of SEQ ID NO:21, the HCDR2 comprising the sequence of SEQ ID NO:22, the HCDR3 comprising the sequence of SEQ ID NO:23, the LCDR1 comprising the sequence of SEQ ID NO: 70, the LCDR2 comprising the sequence of SEQ ID NO:66, and the LCDR3 comprising the sequence of SEQ ID NO:24; or e) the HCDR1 comprising the sequence of SEQ ID NO: 21, the HCDR2 comprising the sequence of SEQ ID NO:22, the HCDR3 comprising the sequence of SEQ ID NO:65, the LCDR1 comprising the sequence of SEQ ID NO:70, the LCDR2 comprising the sequence of SEQ ID NO:66, and the LCDR3 comprising the sequence of SEQ ID NO:24.

In certain embodiments, the antibody or antigen-binding fragment thereof further comprises one or more of heavy chain HFR1, HFR2, HFR3 and HFR4, and/or one or more of light chain LFR1, LFR2, LFR3 and LFR4, wherein: a) the HFR1 comprises QVQLVQSGAEVKKPGASVKVSCK-ASGYTFT (SEQ ID NO: 33) or a homologous sequence of at least 80% (e.g. at least 85%, at least 88%, at least 90%, at least 91%, at least 92%, at least 93%, at least 94%, at least 95%, at least 96%, at least 97%, at least 98%, or at least 99%) sequence identity thereof, b) the HFR2 comprises WVRQ$X_{10}$PGQGLEW$X_{11}$G (SEQ ID NO: 34) or a homologous sequence of at least 80% (e.g. at least 85%, at least 88%, at least 90%, at least 91%, at least 92%, at least 93%, at least 94%, at least 95%) sequence identity thereof, c) the HFR3 sequence comprises RVT$X_{12}$T$X_{13}$D$X_{14}$STSTVYMELSSLRSEDTAVYYCAR (SEQ ID NO: 35) or a homologous sequence of at least 80% (e.g. at least 85%, at least 88%, at least 90%, at least 91%, at least 92%, at least 93%, at least 94%, at least 95%, at least 96%, at least 97%) sequence identity thereof, d) the HFR4 comprises WGQGTLVTVSS (SEQ ID NO: 36) or a homologous sequence of at least 80% (e.g. at least 85%, at least 88%, at least 90%) sequence identity thereof, e) the LFR1 comprises DIQMTQSPSSLSASVGDRVTITC (SEQ ID NO: 37) or a homologous sequence of at least 80% (e.g. at least 85%, at least 88%, at least 90%, at least 91%, at least 92%, at least 93%, at least 94%, at least 95%, at least 96%) sequence identity thereof, f) the LFR2 comprises WYQQKPGX$_{15}$APKLLIX$_{16}$ (SEQ ID NO: 38) or a homologous sequence of at least 80% (e.g. at least 85%, at least 88%, at least 90%, at least 91%, at least 92%, at least 93%, at least 94%) sequence identity thereof, g) the LFR3 comprises GVPSRFSGSGSGX$_{17}$DX$_{18}$TLTISSLQPEDFATYYC (SEQ ID NO: 39) or a homologous sequence of at least 80% (e.g. at least 85%, at least 88%, at least 90%, at least 91%, at least 92%, at least 93%, at least 94%, at least 95%, at least 96%, at least 97%) sequence identity thereof, and h) the LFR4 comprises FGQGTKLEIK (SEQ ID NO: 40) or a homologous sequence of at least 80% (e.g. at least 85%, at least 88%, at least 90%) sequence identity thereof, wherein $X_{10}$ is A or R, $X_{11}$ is M or I, $X_{12}$ is M or L, $X_{13}$ is R or V, $X_{14}$ is T or K, $X_{15}$ is K or N, $X_{16}$ is Y or S, $X_{17}$ is T or K, $X_{18}$ is F or Y.

In certain embodiments, the antibody or antigen-binding fragment thereof provided herein comprises an HFR1 having no more than 3, 2 or 1 amino acid substitutions in the sequence of SEQ ID NO: 33, an HFR2 having no more than 3, 2 or 1 amino acid substitutions in the sequence of the sequence of SEQ ID NO: 34, HFR3 having no more than 6, 5, 4, 3, 2 or 1 amino acid substitutions in the sequence of SEQ ID NO: 35, HFR4 having no more than 4, 3, 2 or 1 amino acid substitutions in the sequence of SEQ ID NO: 36, LFR1 having no more than 6, 5, 4, 3, 2 or 1 amino acid substitution in the sequence of SEQ ID NO: 37, LFR2 having no more than 4, 3, 2 or 1 amino acid substitution in the sequence of SEQ ID NO: 38, LFR3 having no more than 6, 5, 4, 3, 2 or 1 amino acid substitutions in the sequence of SEQ ID NO: 39, and/or LFR4 having no more than 3, 2 or 1 amino acid substitutions in the sequence of SEQ ID NO: 40.

In certain embodiments, the antibody or antigen-binding fragment thereof further comprises a heavy chain HFR1 comprising the sequence of SEQ ID NO: 33, a heavy chain HFR2 comprising the sequence selected from SEQ ID NOs: 41, 42 and 43, a heavy chain HFR3 comprising the sequence selected from SEQ ID NOs: 44, and 45, and a heavy chain HFR4 comprising the sequence of SEQ ID NO: 36.

In certain embodiments, the antibody or antigen-binding fragment thereof further comprises a light chain LFR1 comprising the sequence of SEQ ID NO: 37, a light chain LFR2 comprising the sequence selected from SEQ ID NOs: 46, 47 and 48, a light chain LFR3 comprising the sequence selected from SEQ ID NOs: 49, and 50, and a light chain LFR4 comprising the sequence of SEQ ID NO: 40.

In certain embodiments, the antibody or antigen-binding fragment thereof further comprises a combination of heavy chain HFR1, HFR2, HFR3, and HFR4 selected from: a) the HFR1 comprising the sequence of SEQ ID NO:33, the HFR2 comprising the sequence of SEQ ID NO:41, the HFR3 comprising the sequence of SEQ ID NO:44, and the HFR4 comprising the sequence of SEQ ID NO:36; b) the HFR1 comprising the sequence of SEQ ID NO: 33, the HFR2 comprising the sequence of SEQ ID NO:41, the HFR3 comprising the sequence of SEQ ID NO:45, and the HFR4 comprising the sequence of SEQ ID NO:36; c) the HFR1 comprising the sequence of SEQ ID NO:33, the HFR2 comprising the sequence of SEQ ID NO:42, the HFR3 comprising the sequence of SEQ ID NO:45, and the HFR4 comprising the sequence of SEQ ID NO:36; and d) the HFR1 comprising the sequence of SEQ ID NO:33, the HFR2 comprising the sequence of SEQ ID NO:43, the HFR3 comprising the sequence of SEQ ID NO:45, and the HFR4 comprising the sequence of SEQ ID NO:36.

In certain embodiments, the antibody or antigen-binding fragment thereof further comprises a combination of light chain LFR1, LFR2, LFR3, and LFR4 selected from: a) the LFR1 comprising the sequence of SEQ ID NO:37, the LFR2 comprising the sequence of SEQ ID NO:46, the LFR3 comprising the sequence of SEQ ID NO:49, and the LFR4 comprising the sequence of SEQ ID NO:40; b) the LFR1 comprising the sequence of SEQ ID NO: 37, the LFR2 comprising the sequence of SEQ ID NO:46, the LFR3 comprising the sequence of SEQ ID NO:50, and the LFR4 comprising the sequence of SEQ ID NO: 40; c) the LFR1 comprising the sequence of SEQ ID NO:37, the LFR2 comprising the sequence of SEQ ID NO:47, the LFR3 comprising the sequence of SEQ ID NO:50, and the LFR4 comprising the sequence of SEQ ID NO:40; and d) the LFR1 comprising the sequence of SEQ ID NO:37, the LFR2 comprising the sequence of SEQ ID NO:48, the LFR3 comprising the sequence of SEQ ID NO:50, and the LFR4 comprising the sequence of SEQ ID NO:40.

In certain embodiments, the antibody or antigen-binding fragment thereof comprises a heavy chain variable region ($V_H$) comprising the sequence of SEQ ID NOs: 7, 9, 67, or 51-54 or a homologous sequence having at least 80% (e.g. at least 85%, at least 88%, at least 90%, at least 91%, at least 92%, at least 93%, at least 94%, at least 95%, at least 96%, at least 97%, at least 98%, or at least 99%) sequence identity thereof.

In certain embodiments, the antibody or antigen-binding fragment thereof comprises a light chain variable region ($V_L$) comprising the sequence of SEQ ID NOs: 8, 10, 68, or 55-58 or a homologous sequence having at least 80% (e.g. at least 85%, at least 88%, at least 90%, at least 91%, at least 92%, at least 93%, at least 94%, at least 95%, at least 96%, at least 97%, at least 98%, or at least 99%) sequence identity thereof.

In certain embodiments, the antibody or antigen-binding fragment thereof comprises a) a heavy chain variable region comprising the sequence of SEQ ID NO: 7 and a light chain variable region comprising the sequence of SEQ ID NO: 8; b) a heavy chain variable region comprising the sequence of SEQ ID NO: 9 and a light chain variable region comprising the sequence of SEQ ID NO: 10; c) a heavy chain variable region comprising the sequence of SEQ ID NO: 51 and a light chain variable region comprising the sequence of SEQ ID NO:55; d) a heavy chain variable region comprising the sequence of SEQ ID NO: 52 and a light chain variable region comprising the sequence of SEQ ID NO:55; e) a heavy chain variable region comprising the sequence of SEQ ID NO: 53 and a light chain variable region comprising the sequence of SEQ ID NO:55; f) a heavy chain variable region comprising the sequence of SEQ ID NO: 54 and a light chain variable region comprising the sequence of SEQ ID NO:55; g) a heavy chain variable region comprising the sequence of SEQ ID NO: 51 and a light chain variable region comprising the sequence of SEQ ID NO:56; h) a heavy chain variable region comprising the sequence of SEQ ID NO: 52 and a light chain variable region comprising the sequence of SEQ ID NO:56; i) a heavy chain variable region comprising the sequence of SEQ ID NO: 53 and a light chain variable region comprising the sequence of SEQ ID NO:56; j) a heavy chain variable region comprising the sequence of SEQ ID NO: 54 and a light chain variable region comprising the sequence of SEQ ID NO:56; k) a heavy chain variable region comprising the sequence of SEQ ID NO: 51 and a light chain variable region comprising the sequence of SEQ ID NO:57; 1) a heavy chain variable region comprising the sequence of SEQ ID NO: 52 and a light chain variable region comprising the sequence of SEQ ID NO:57; m) a heavy chain variable region comprising the sequence of SEQ ID NO: 53 and a light chain variable region comprising the sequence of SEQ ID NO:57; n) a heavy chain variable region comprising the sequence of SEQ ID NO: 54 and a light chain variable region comprising the sequence of SEQ ID NO:57; o) a heavy chain variable region comprising the sequence of SEQ ID NO: 51 and a light chain variable region comprising the sequence of SEQ ID NO:58; p) a heavy chain variable region comprising the sequence of SEQ ID NO: 52 and a light chain variable region comprising the sequence of SEQ ID NO:58; q) a heavy chain variable region comprising the sequence of SEQ ID NO: 53 and a light chain variable region comprising the sequence of SEQ ID NO:58; r) a heavy chain variable region comprising the sequence of SEQ ID NO: 54 and a light chain variable region comprising the sequence of SEQ ID NO:58; s) a heavy chain variable region comprising the sequence of SEQ ID NO: 67 and a light chain variable region comprising the sequence of SEQ ID NO:56; t) a heavy chain variable region comprising the sequence of SEQ ID NO: 52 and a light chain variable region comprising the sequence of SEQ ID NO:68; or u) a heavy chain variable region comprising the sequence of SEQ ID NO: 67 and a light chain variable region comprising the sequence of SEQ ID NO:68.

In certain embodiments, the antibody or antigen-binding fragment thereof further comprises an immunoglobulin constant region, optionally a constant region of human immunoglobulin, or optionally a constant region of human IgG (for example, of IgG1, IgG2, IgG3 or IgG4). In certain embodiments, the constant region comprises one or more modifications. In certain embodiments, the modification introduces or removes a glycosylation site. In certain embodiments, the modification introduces a free cysteine residue. In certain embodiments, the modification alters Fc-mediated effector function, e.g. increased or reduced antibody-dependent cell-mediated cytotoxicity (ADCC), complement dependent cytotoxicity (CDC), or Fc receptor binding.

In certain embodiments, the antibody or antigen-binding fragment thereof is a humanized monoclonal antibody. In certain embodiments, the antibody or antigen-binding fragment thereof is a chimeric antibody or antigen-binding fragment thereof. In certain embodiments, the antigen-binding fragment thereof is a camelized single domain antibody, a diabody, a scFv (single chain Fv), an scFv dimer, a BsFv (bispecific Fv), a dsFv, a $(dsFv)_2$, a dsFv-dsFv', an Fv fragment, a Fab, a Fab', a $F(ab')_2$, a ds diabody, a nanobody, a domain antibody, or a bivalent domain antibody.

In certain embodiments, the antibody or antigen-binding fragment thereof inhibits IFNα- and/or IFNω-mediated human IFNAR1 activation.

In certain embodiments, the antibody or antigen-binding fragment thereof does not inhibit IFNβ-mediated human IFNAR1 activation.

In certain embodiments, the antibody or antigen-binding fragment thereof does not inhibit IFNβ-mediated anti-viral activity.

In certain embodiments, the inhibition effect of the antibody or antigen-binding fragment thereof on IFNα- or on IFNω-mediated human IFNAR1 activation or anti-viral activity is at least four, five, six, seven, eight, nine, ten, eleven, twelve, thirteen, fourteen, fifteen times higher than that on IFNβ-mediated human IFNAR1 activation or anti-viral activity.

In certain embodiments the antibody or antigen-binding fragment thereof is isolated from its natural sources.

In certain embodiments, the antibody or antigen-binding fragment thereof is linked to one or more conjugate moieties.

In another aspect the present disclosure provides an anti-human IFNAR1 antibody or antigen-binding fragment thereof, which competes for binding to human IFNAR1 with the antibody or antigen-binding fragment thereof provided herein, and wherein the antibody or antigen-binding fragment thereof does not inhibit IFNβ-mediated human IFNAR1 activation.

In certain embodiments, the antibody or antigen-binding fragment thereof is capable of specifically binding to human IFNAR1 at a $K_D$ value of no more than $8\times10^{-8}$M (e.g. no more than $5\times10^{-8}$M, no more than $2\times10^{-8}$M, no more than $8\times10^{-9}$M, no more than $5\times10^{-9}$M, no more than $2\times10^{-9}$M, no more than $10^{-9}$ M, no more than $8\times10^{-10}$M, no more than $7\times10^{-10}$M, or no more than $6\times10^{-10}$M) as measured by Biacore.

In certain embodiments, the antibody or antigen-binding fragment thereof is capable of specifically binding to human IFNAR1 at a $EC_{50}$ value of no more than 0.1 μg/ml (e.g. no more than 0.09 μg/ml, no more than 0.08 μg/ml, no more than 0.07 μg/ml, no more than 0.06 μg/ml, no more than 0.05 μg/ml, no more than 0.04 μg/ml, no more than 0.03 μg/ml, no more than 0.02 μg/ml, no more than 0.01 μg/ml, no more than 0.009 μg/ml, no more than 0.008 μg/ml, no more than 0.007 μg/ml, no more than 0.006 μg/ml, or no more than 0.005 μg/ml) as measured by ELISA.

In another aspect, the present disclosure provides an anti-human IFNAR1 antibody or antigen-binding fragment thereof, which binds to both a first fragment within amino acid residues 127-227 of IFNAR1 and a second fragment within amino acid residues of 231-329 of IFNAR1, and does not inhibit IFNB-mediated IFNAR1 activation. In certain embodiments, the antibodies and antigen-binding fragments provided herein can specifically bind to a human/mouse chimeric IFNAR1 (i.e. SEQ ID NO: 69).

In certain embodiments, the antibody or antigen-binding fragment thereof does not bind to a truncated human IFNAR1 absent of either a) amino acid residues 127-227 or b) amino acid residues 231-329.

In certain embodiments, the antibody or antigen-binding fragment thereof is capable of specifically binding to a truncated human IFNAR1 absent of: a) amino acid residues 32-126, b) amino acid residues 331-432, or both a) and b).

In certain embodiments, the antibody or antigen-binding fragment thereof binds to the truncated human IFNAR1 at a binding capacity comparable to that of the full-length human IFNAR1.

In certain embodiments, the antibody or antigen-binding fragment thereof comprises a heavy chain variable region that is a product of or derived from a mouse IGHV1-69 gene, a mouse IGHD2-4 gene, and a mouse IGHJ4 gene, and/or a light chain variable region that is a product of or derived from a mouse IGKV13-84 gene and a mouse IGKJ4 gene. In certain embodiments, the antibody or antigen-binding fragment thereof is humanized.

In another aspect, the present disclosure provides an antibody produced by the hybridoma cell having a deposit number of CGMCC deposit No. 16286 or CGMCC deposit No. 16287, or an antigen-binding fragment thereof.

In certain embodiments, the antibody or antigen-binding fragment thereof is bispecific.

In another aspect, the present disclosure provides an isolated polynucleotide encoding the antibody or antigen-binding fragment thereof provided herein. In certain embodiments, the isolated polynucleotide comprises a nucleotide sequence selected from the group consisting of SEQ ID NOs: 11 and 13, and a homologous sequence thereof having at least 80% (e.g. at least 85%, at least 88%, at least 90%, at least 91%, at least 92%, at least 93%, at least 94%, at least 95%, at least 96%, at least 97%, at least 98%, or at least 99%) sequence identity to SEQ ID NOs: 11 or 13. In certain embodiments, the isolated polynucleotide further comprises a nucleotide sequence selected from the group consisting of SEQ ID NOs: 12 and 14, and a homologous sequence thereof having at least 80% (e.g. at least 85%, at least 88%, at least 90%, at least 91%, at least 92%, at least 93%, at least 94%, at least 95%, at least 96%, at least 97%, at least 98%, or at least 99%) sequence identity to SEQ ID NOs: 12 or 14. In certain embodiments, the homologous sequence encodes an amino acid sequence identical to that encoded by SEQ ID NOs: 11, 12, 13, or 14.

In another aspect, the present disclosure provides an expression vector comprising the isolated polynucleotide provided herein.

In another aspect, the present disclosure provides a host cell comprising the expression vector provided herein. In certain embodiments, the host cell is capable of producing the antibody or antigen-binding fragment thereof provided herein.

In another aspect, the present disclosure provides a hybridoma cell having a deposit number of CGMCC deposit No. 16286 or CGMCC deposit No. 16287.

In another aspect, the present disclosure provides a method of producing the antibody or antigen-binding fragment thereof provided herein, comprising culturing the host cell provided herein under the condition at which the expression vector provided herein is expressed. In certain embodiments, the method further comprises purifying the antibody or antigen-binding fragment thereof produced by the host cell.

In another aspect, the present disclosure provides a pharmaceutical composition comprising the antibody or antigen-binding fragment thereof provided herein, and a pharmaceutically acceptable carrier.

In another aspect, the present disclosure provides a method of treating a type I IFN-related disease or condition in a subject, comprising administering a therapeutically effective amount of the antibody or antigen-binding fragment thereof provided herein, or the pharmaceutical composition provided herein. In certain embodiments, the type I IFN is IFNα and/or IFNω. In certain embodiments, the disease or condition is characterized in expressing or overexpressing of type I interferon (IFN) and/or type I IFN signature genes. In certain embodiments, the disease is HIV infection or AIDS, insulin-dependent diabetes mellitus (IDDM), inflammatory bowel disease (IBD), Crohn's Disease, Ulcerative Colitis, Celiac's Disease, Chronic obstructive pulmonary disease (COPD), psoriasis, autoimmune thyroiditis, autoimmune primary hypothyroidism, Graves' Disease, Hashimoto's thyroiditis, destructive thyroiditis with hypothyroidism, glomerulonephritis, IgA nephropathy, IgM polyneuropathies, myasthenia gravis, Reynaud's syndrome, pustulosis palmoplantaris (PPP), erosive lichen planus, pemphigus bullosa, epidermolysis bullosa, contact dermatitis and atopic dermatitis, polyradiculitis, systemic lupus erythematosus (SLE), myositis, Sjögren's syndrome, rheumatoid arthritis, systemic sclerosis, scleroderma, multiple sclerosis (MS), idiopathic inflammatory myopathies (IIM), rheumatoid arthritis (RA), transplant rejection and graft versus host disease (GVHD), and Aicardi-Goutières syndrome (AGS). In certain embodiments, IFNβ-mediated IFNAR1 activation is not inhibited. In certain embodiments, the method further comprising administering a therapeutically effective amount of IFNβ.

In another aspect, the present disclosure provides a method of inhibiting bioactivity of a cell expressing or overexpressing IFNα and/or IFNω, comprising contacting the cell with the antibody or antigen-binding fragment thereof provided herein.

In another aspect, the present disclosure provides a method of detecting presence or level of human IFNAR1 in a sample, comprising contacting the sample with the antibody or antigen-binding fragment thereof provided herein.

In another aspect, the present disclosure provides a detecting or therapeutic kit comprising the antibody or antigen-binding fragment thereof provided herein and instructions for use.

In another aspect, the present disclosure provides use of the antibody or antigen-binding fragment thereof of provided herein in the manufacture of a medicament for treating a type I IFN-related disease or condition in a subject in need thereof.

BRIEF DESCRIPTION OF THE DRAWINGS

FIG. 1 shows the binding of anti-human IFNAR1 monoclonal antibodies 7G4 and 10C5 to human IFNAR1. FIG. 1A is a schematic flow cytometry diagram of 7G4 and 10C5 binding to human IFNAR1 overexpressed on 293T cell surface ("Isotype" means an isotype control antibody that does not bind to IFNAR1, "7G4" means the 7G4 antibody, "10C5" means the 10C5 antibody). The Y axis is intensity of Green Fluorescence Protein (GFP), representing human IFNAR1 expression; the X axis is intensity of Phycoerythrin (PE), indicating the binding of monoclonal antibody to human IFNAR1. FIG. 1B is the statistical result of the mean fluorescence intensity (MFI) of GFP positive cells on X axis in FIG. 1A.

FIG. 2 shows the binding of anti-human IFNAR1 monoclonal antibodies 7G4 and 10C5 to different truncations of human IFNAR1. FIG. 2A is a schematic diagram of truncations of human IFNAR1, and a summary of 7G4 and 10C5 binding results. "+" indicates that the antibody binds to the truncation; "–" indicates that the antibody does not bind to the truncation. FIG. 2B is a statistic bar graph of the percentage of PE-positive cells, where 7G4 and 10C5 bind to 293T cells overexpressing different truncations of human IFNAR1.

FIG. 4A and FIG. 4B represent results for the Sindbis Virus (SINV). FIG. 4C and FIG. 4D represent results for the Influenza virus (Flu). FIG. 4E and FIG. 4F represent results for the Herpes simplex virus type 1 (HSV-1). "*" indicates $p<0.05$, "**" indicates $p<0.01$, and "ns" represents no significant difference when compared with isotype control.

FIG. 6 shows the nucleotide sequence (SEQ ID NO: 11) and amino acid sequence (SEQ ID NO: 7) of the heavy chain variable region of anti-human IFNAR1 monoclonal antibody 7G4. The shadings show the sequences of CDR1 (SEQ ID NO: 21), CDR2 (SEQ ID NO: 22) and CDR3 (SEQ ID NO: 23) of the heavy chain, respectively.

FIG. 7 shows the nucleotide sequence (SEQ ID NO: 12) and amino acid sequence (SEQ ID NO: 8) of the light chain variable region of IFNAR1 monoclonal antibody 7G4. The shadings show the sequences of CDR1 (SEQ ID NO: 70), CDR2 (SEQ ID NO: 71) and CDR3 (SEQ ID NO: 24) of the light chain, respectively.

FIG. 8 shows the nucleotide sequence (SEQ ID NO: 13) and amino acid sequence (SEQ ID NO: 9) of the heavy chain variable region of anti-human IFNAR1 monoclonal antibody 10C5. The shadings show the sequences of CDR1 (SEQ ID NO: 25), CDR2 (SEQ ID NO: 26) and CDR3 (SEQ ID NO: 27) of the heavy chain, respectively.

FIG. 9 shows the nucleotide sequence (SEQ ID NO: 14) and amino acid sequence (SEQ ID NO: 10) of the light chain variable region of anti-human IFNAR1 monoclonal antibody 10C5. The shadings show the sequences of CDR1 (SEQ ID NO: 72), CDR2 (SEQ ID NO: 66) and CDR3 (SEQ ID NO: 28) of the light chain, respectively.

FIG. 10 shows the alignment result of the amino acid sequence of the heavy chain variable region of anti-human IFNAR1 monoclonal antibody 7G4 (SEQ ID NO: 7) and 10C5 (SEQ ID NO: 9) with the amino acid sequence encoded by the original VDJ gene of mouse V region (SEQ ID NO: 15). Consensus sequence of the heavy chain variable region of murine species are also shown in the alignment.

FIG. 11 shows the alignment result of the amino acid sequence of the light chain variable region of anti-human IFNAR1 monoclonal antibody 7G4 (SEQ ID NO: 8) and 10C5 (SEQ ID NO: 10) with the amino acid sequence encoded by the original VJ gene of mouse V region (SEQ ID NO: 16). Consensus sequence of the light chain variable region of murine species are also shown in the alignment.

FIG. 13 shows the blocking activity of Hu7G4 variants (i.e. Hu4-5 to Hu4-16) to human IFNAR1 activation mediated by IFNα (FIG. 13A) but not by IFNβ (FIG. 13B). The horizontal axis indicates the test antibodies or controls of mock or isotype. "5" means Hu4-5, and so forth.

FIG. 15A shows two 7G4 humanized antibodies Hu4-6 and Hu4-13 having similar binding efficiency to human IFNAR1; FIG. 15B shows all three of Hu4-6 mutants bind to human IFNAR1 with similar binding efficiency. Hu4-6-mut-1: A108G in VH; Hu4-6-mut-2: T53S and S56T in VL; Hu4-6-mut-3: A108G in VH and T53S and S56T in VL.

FIG. 16 shows the sequences of SEQ ID NO: 1-SEQ ID NO: 72 referred to herein.

DETAILED DESCRIPTION OF THE INVENTION

Figure 3:
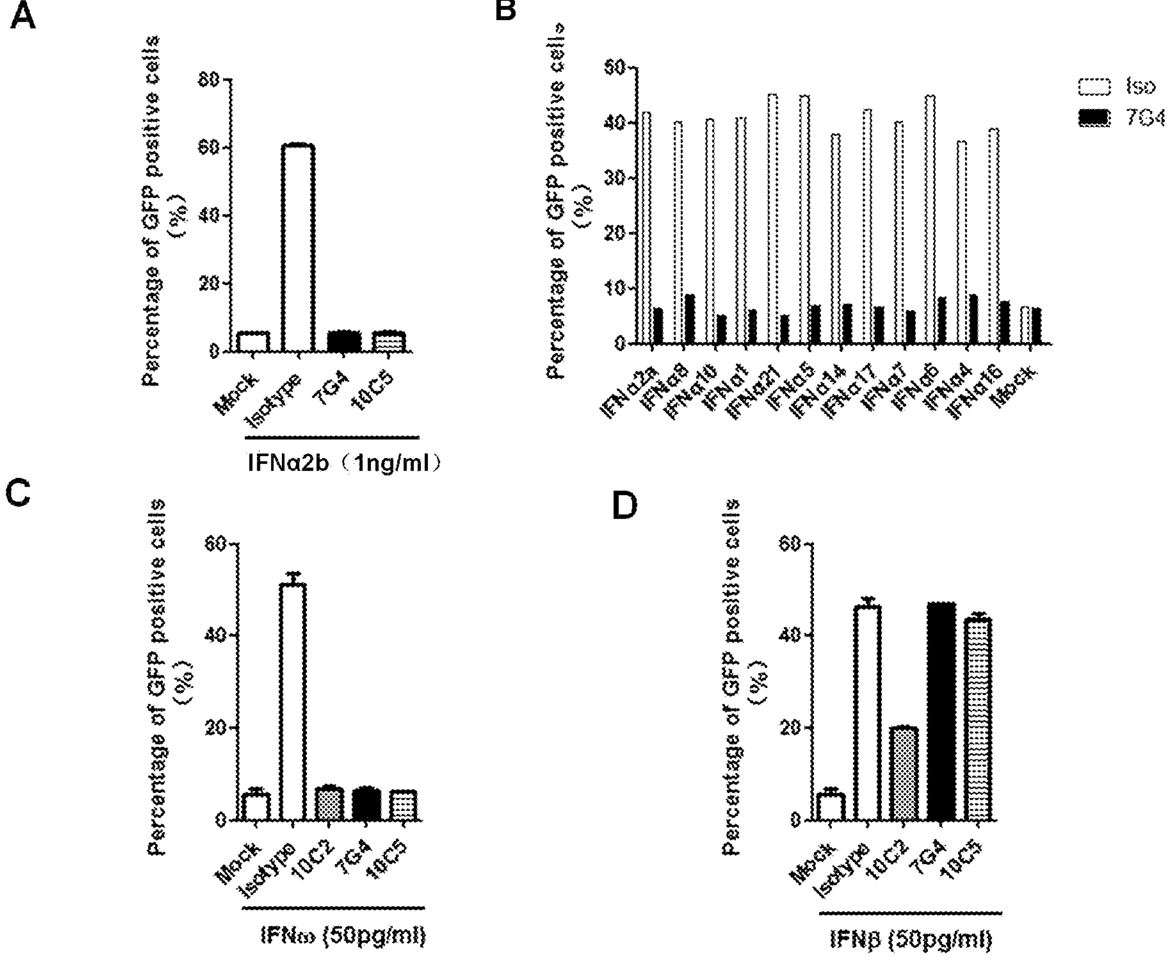
FIG. 3 shows that antibodies 7G4 and 10C5 blocked activation of human IFNAR1 mediated by IFNα2b (FIG. 3A), 12 IFNα subtypes (FIG. 3B), and IFNω (FIG. 3C), but did not block human IFNAR1 activation mediated by IFNβ (FIG. 3D), as measured by flow cytometry. "10C2" means the antibody 10C2 disclosed in PCT publication WO2018/010140.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, third, and optionally fourth constant region ($C_{H1}$, $C_{H2}$, $C_{H3}$, $C_{H4}$ respectively); mammalian light chains are classified as λ or κ, while each light chain consists of a variable region ($V_L$) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273 (4), 927 (1997); Chothia, C. et al., J Mol Biol. December 5; 186 (3): 651-63 (1985); Chothia, C. and Lesk, A. M., J. Mol. Biol., 196,901 (1987); Chothia, C. et al., Nature. December 21-28; 342 (6252): 877-83 (1989); Kabat E. A. et al., Sequences of Proteins of immunological Interest, 5th Ed. Public Health Service, National Institutes of Health, Bethesda, Md. (1991); Marie-Paule Lefranc et al, Developmental and Comparative Immunology, 27:55-77 (2003); Marie-Paule Lefranc et al, Immunome Research, 1 (3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgAQ1 (alpha1 heavy chain), or IgA2 (alpha2 heavy chain).

The term "bivalent" as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"$F(ab')_2$" refers to a dimer of Fab'. "Fv" with regard to an antibody refers to the smallest fragment of the antibody to bear the complete antigen-binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "$(dsFv)_2$" or "(dsFv-dsFv')" comprises three peptide chains: two $V_H$ moieties linked by a peptide linker (e.g. a long flexible linker) and bound to two $V_L$ moieties, respectively, via disulfide bridges. In some embodiments, dsFv-dsFv' is bispecific in which each disulfide paired heavy and light chain has a different antigen specificity.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879 (1988)).

"Fc" with regard to an antibody (e.g. of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), and complement dependent cytotoxicity (CDC), but does not function in antigen binding.

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231 (1-2): 25-38 (1999); Muyldermans S., J Biotechnol. June; 74 (4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363 (6428): 446-8 (1993); Nguyen V K. et al. Immunogenetics. April; 54 (1): 39-47 (2002); Nguyen V K. et al. Immunology. May; 109 (1): 93-101 (2003)). The variable domain of a heavy chain antibody (VHH domain) represents the smallest known antigen-binding unit generated by adaptive immune responses (Koch-Nolte F. et al., FASEB J. November; 21 (13): 3490-8. Epub 2007 Jun. 15 (2007)).

A "nanobody" refers to an antibody fragment that consists of a VHH domain from a heavy chain antibody and two constant domains, CH2 and CH3.

"Diabodies" or "dAbs" include small antibody fragments with two antigen-binding sites, wherein the fragments comprise a Vu domain connected to a $V_L$ domain in the same polypeptide chain ($V_H$-$V_L$ or $V_L$-$V_H$) (see, e.g. Holliger P. et al., Proc Natl Acad Sci USA. July 15; 90 (14): 6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes). In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising VHI-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions derived from human.

"IFNAR1" as used herein, refers to interferon alpha receptor 1 derived from mammals such as primates (e.g. humans, monkeys). In certain embodiments, the IFNAR1 is human IFNAR1. Exemplary sequence of human IFNAR1 includes human IFNAR1 protein (NCBI Ref Seq No. NP_000620.2). Exemplary sequence of IFNAR1 includes *Macaca* mulatta (Rhesus monkey) IFNAR1 protein (NCBI Ref Seq No. NP_001253442.1), *Macaca fascicularis* (crab-eating macaque) IFNAR1 protein (NCBI Ref Seq No.XP_005548866.2, or No. XP_015302385.1, or No. XP_005548864.1, or No. XP_005548865.1).

IFNAR1 is one of the two transmembrane proteins through which type I interferons (IFN-Is) signal. Activation of IFNAR1 by IFN-Is are known to lead to anti-viral activity, as well as anti-bacterial, anti-protozoal, immunomodulatory, anti-proliferative activities and cell-growth regulatory functions.

IFN-Is are a large family of structurally related cytokines that have pleiotropic effects on a wide variety of cell types. In certain embodiments, the IFN-Is are human IFN-Is. The IFN-I family consists of 5 closely related members including IFNα, IFNβ, IFNε, IFNκ and IFNω. IFNα has a total of 13 subtypes including IFNA1, IFNA2, IFNA4, IFNA5, IFNA6, IFNA7, IFNA8, IFNA10, IFNA13, IFNA14, IFNA16, IFNA17 and IFNA21, in which IFNA1 and IFNA13 have identical amino acid sequences. "IFNα" as used herein encompasses all subtypes of IFNα.

"IFNω" is another IFN-I which is encoded by at least 5 pseudogenes and 1 functional gene which exhibits 70% homology with the IFN-α genes.

"IFN-β" is encoded by a single copy gene which has approximately 50% homology with the IFNα genes. IFNβ has substantially higher integral affinity to the cell surface receptor compared with IFNα or IFNω. Accordingly, IFNβ, but not IFNα or IFNω, binds to IFNAR1 in an IFNAR2-independent manner, and the IFNAR1-IFNβ complex transduces signals in a more efficient way. It is believed that IFNβ exhibits much greater potency than IFNα or IFNω in inhibiting monocyte differentiation, inhibiting viral replication, inducing apoptosis of human tumoral cells and the like.

The term "anti-IFNAR1 antibody" refers to an antibody that is capable of specific binding to IFNAR1 (e.g. human or monkey IFNAR1). The term "anti-human IFNAR1 antibody" refers to an antibody that is capable of specific binding to human IFNAR1.

The term "specific binding" or "specifically binds" as used herein refers to a non-random binding reaction between two molecules, such as for example between an antibody and an antigen. Specific binding can be characterized in binding affinity, for example, represented by $K_D$ value, i.e., the ratio of dissociation rate to association rate ($k_{off}/k_{on}$) when the binding between the antigen and antigen-binding molecule reaches equilibrium. $K_D$ may be determined by using any conventional method known in the art, including but are not limited to surface plasmon resonance method, microscale thermophoresis method, HPLC-MS method and flow cytometry (such as FACS) method. A $K_D$ value of $\leq 10^{-6}$ M (e.g. $\leq 5\times10^{-7}$ M, $\leq 2\times10^{-7}$ M, $\leq 10^{-7}$M, $\leq 5\times10^{-8}$ M, $\leq 2\times10^{-8}$ M, $\leq 10^{-8}$ M, $\leq 5\times10^{-9}$M, $\leq 4\times10^{-9}$M, $\leq 3\times10^{-9}$ M, $\leq 3\times1^{-9}$ M, or $\leq 10^{-9}$ M) can indicate specific binding between an antibody or antigen binding fragments thereof and IFNAR1 (e.g. human IFNAR1).

The ability to "compete for the same epitope" as used herein refers to the ability of an antibody or antigen-binding fragment to inhibit the binding interaction between two molecules (e.g. human IFNAR1 and an anti-IFNAR1 antibody) to any detectable degree. In certain embodiments, an antibody or antigen-binding fragment that blocks binding between two molecules inhibits the binding interaction between the two molecules by at least 85%, or at least 90%. In certain embodiments, this inhibition may be greater than 95%, or greater than 99%.

The term "epitope" as used herein refers to the specific group of atoms or amino acids on an antigen to which an antibody binds. Two antibodies may bind the same or a closely related epitope within an antigen if they exhibit competitive binding for the antigen. An epitope can be linear or conformational (i.e. including amino acid residues spaced apart). For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

Those skilled in the art will recognize that it is possible to determine, without undue experimentation, if a given antibody binds to the same or a closely related epitope as the antibody of present disclosure (e.g. mouse monoclonal antibodies 7G4 and 10C5, and humanized antibodies Hu4-1, Hu4-2, Hu4-3, Hu4-4, Hu4-5, Hu4-6, Hu4-6-mut-1, Hu4-6-mut-2, Hu4-6-mut-3, Hu4-7, Hu4-8, Hu4-9, Hu4-10, Hu4-11, Hu4-12, Hu4-13, Hu4-14, Hu4-15, Hu4-16) by ascertaining whether the former prevents the latter from binding to a IFNAR1 antigen polypeptide. If the given antibody competes with the antibody of present disclosure, as shown by a decrease in binding by the antibody of present disclosure to the IFNAR1 antigen polypeptide, then the two antibodies bind to the same, or a closely related, epitope. Or if the binding of a given antibody to the IFNAR1 antigen polypeptide was inhibited by the antibody of present disclosure, then the two antibodies bind to the same, or a closely related, epitope.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homologous" as used herein refers to nucleic acid sequences (or its complementary strand) or amino acid sequences that have sequence identity of at least 60% (e.g. at least 65%, 70%, 75%, 80%, 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23 (21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) mediated by interaction of antibodies and C1q on the C1 complex; antibody-dependent cell-mediated cytotoxicity (ADCC) mediated by binding of Fc region of an antibody to Fc receptor on an effector cell; and phagocytosis. Effector functions can be evaluated using various assays such as Fc receptor binding assay, C1q binding assay, and cell lysis assay.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or antigen-binding fragment thereof" refers to the antibody or antigen-binding fragments thereof having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a genetic element may be operably inserted so as to bring about the expression of that genetic element, such as to produce the protein, RNA or DNA encoded by the genetic element, or to replicate the genetic element. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g. expression vectors) containing the nucleic acid sequence provided herein encoding the antibody or antigen-binding fragment thereof, at least one promoter (e.g. SV40, CMV, EF-1$\alpha$) operably linked to the nucleic acid sequence, and at least one selection marker.

The phrase "host cell" as used herein refers to a cell into which an exogenous polynucleotide and/or a vector can be or has been introduced.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

A "type I IFN related" disease or condition as used herein refers to any disease or condition caused by, exacerbated by, or otherwise linked to increased or decreased expression or activities of type I IFN. In some embodiments, the type I IFN related disease or condition is immune-related disorder, such as, for example, an autoimmune disease. In certain embodiments, the type I IFN related disease or condition is characterized in expressing or over-expressing of type I interferon (IFN-I) and/or type I IFN signature genes.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-IFNAR1 Antibody

The present disclosure provides anti-IFNAR1 antibodies and antigen-binding fragments thereof. The anti-IFNAR1 antibodies and antigen-binding fragments provided herein are capable of specific binding to IFNAR1.

In certain embodiments, the antibodies and the fragments thereof provided herein specifically bind to human IFNAR1 at an $K_D$ value of no more than $8\times10^{-8}$ M, no more than $5\times10^{-8}$ M, no more than $2\times10^{-8}$ M, no more than $8\times10^{-9}$ M, no more than $5\times10^{-9}$ M, no more than $2\times10^{-9}$ M, no more than $10^{-9}$ M, no more than $8\times10^{-10}$ M, no more than $7\times10^{-10}$ M, or no more than $6\times10^{-10}$ M by Biacore assay. Biacore assay is based on surface plasmon resonance technology, see, for example, Murphy, M. et al, Current protocols in protein science, Chapter 19, unit 19.14, 2006.

Binding of the antibodies to human IFNAR1 can also be represented by "half maximal effective concentration" ($EC_{50}$) value, which refers to the concentration of an antibody where 50% of its maximal binding is observed. The $EC_{50}$ value can be measured by binding assays known in the art, for example, sandwich assay such as enzyme-linked immunosorbent assay (ELISA), flow cytometry assay, and other binding assay. In certain embodiments, the antibodies and the fragments thereof provided herein specifically bind to human IFNAR1 at an $EC_{50}$ (i.e. 50% binding concentration) of no more than 0.1 μg/ml, no more than 0.09 μg/ml, no more than 0.08 μg/ml, no more than 0.07 μg/ml no more than 0.06 μg/ml, no more than 0.05 μg/ml, no more than 0.04 μg/ml, no more than 0.03 μg/ml, no more than 0.02 μg/ml no more than 0.01 μg/ml, no more than 0.009 μg/ml, no more than 0.008 μg/ml, no more than 0.007 μg/ml, no more than 0.006 μg/ml or no more than 0.005 μg/ml by ELISA.

The anti-IFNAR1 antibodies and antigen-binding fragments thereof provided herein bind to human IFNAR1 at an epitope covering both a first fragment within amino acid residues 127-227 of IFNAR1 and a second fragment within amino acid residues 231-329 of IFNAR1.

The unprocessed human IFNAR1 expression product is composed of 557 amino acids including an extracellular domain (ECD) of 409 residues, a transmembrane domain of 21 residues, and an intracellular domain of 100 residues. The ECD of IFNAR1 is composed of two domains, domain 1 and domain 2, which are separated by a three-proline motif. Each domain is composed of approximately 200 residues and can be further subdivided into two homologous subdomains of approximately 100 amino acids. Thus, the ECD of IFNAR1 can be divided into four subdomains: Subdomain 1 (spanning from amino acid residues 32 to 126 of wild type human IFNAR1, i.e. SEQ ID NO: 17), Subdomain 2 (i.e. from amino acid residues 127-227 of wild type human IFNAR1, i.e. SEQ ID NO: 18), Subdomain 3 (from amino acid residues 231-329 of wild type human IFNAR1, i.e. SEQ ID NO: 19), and Subdomain 4 (from amino acid residues 331-432 residues of wild type human IFNAR1, i.e. SEQ ID NO: 20).

The first fragment within amino acid residues 127-227 of IFNAR1 (Subdomain 2) can be of any suitable length as sufficient to constitute a portion of an epitope for antibody binding (for example, at least 3, 4, 5, 6, 7, 8, 9, 10, 11, 12, 13, 14, 15, 20, 25, 30, 25, 40, 50, 60, 70, 80, or 90 amino acid residues), and can be at any suitable position within the Subdomain 2 of IFNAR1 (for example, around the amino acid residues 127 or 227, or somewhere between the amino acid residues 127 and 227).

Similarly, the second fragment within amino acid residues 231-329 of IFNAR1 (Subdomain 3) can be of any suitable length as sufficient to constitute a portion of an epitope for antibody binding (for example, at least 3, 4, 5, 6, 7, 8, 9, 10, 11, 12, 13, 14, 15, 20, 25, 30, 25, or 40 amino acid residues), and can be at any suitable position within the Subdomain 3 of IFNAR1 (for example, around the amino acid residues 231 or 329, or somewhere between the amino acid residues 231 and 329).

In certain embodiments, the antibodies and antigen-binding fragments provided herein can specifically bind to an epitope spanning through the intersection between Subdomain 2 and Subdomain 3. In certain embodiments, the antibodies and antigen-binding fragments provided herein can specifically bind to an epitope covering the segment from amino acid residues 227-231, or the segment from amino acid residues 226-232. On the other hand, the antibodies and antigen-binding fragments provided herein do not need to bind to each and every residue over the entire length of Subdomain 2 or Subdomain 3. It is sufficient to have at least one binding site within Subdomain 2 and at least one additional binding site within Subdomain 3, and therefore exhibit binding to both Subdomain 2 and Subdomain 3. In certain embodiments, the antibodies and antigen-binding fragments provided herein can specifically bind to a human/mouse chimeric IFNAR1 (i.e. SEQ ID NO: 69) comprising human wild type IFNAR1 sequence except that the amino acid residues 149-214 are replaced by the mouse IFNAR1 counterpart.

In certain embodiments, the antibody or antigen-binding fragment thereof provided herein does not bind to a truncated IFNAR1 absent of either a) amino acid residues 127-227 (Subdomain 2) or b) amino acid residues 231-329 (Subdomain 3). A "truncated IFNAR1" as used herein refers to a modified IFNAR1 which is otherwise identical to the wild-type IFNAR1 except that one or more fragments are missing or replaced by a significantly different fragment, such as alanine or poly alanine. The antibody or antigen-binding fragment thereof provided herein cannot bind to a truncated IFNAR1 which lacks Subdomain 2, or lacks Subdomain 3, or lacks both. This indicates that the binding site within Subdomain 2, and the binding site within Subdomain 3 of IFNAR1 are both necessary and indispensable for the antibodies and antigen-binding fragments thereof provided herein to bind specifically to IFNAR1. Absence of either Subdomain 2 or Subdomain 3 or both is sufficient to impair or eliminate the IFNAR1 specific binding of the antibodies and antigen-binding fragments thereof provided herein. On the other hand, this may additionally or alternatively indicate that the intersection between Subdomain 2 and Subdomain 3 is potentially required for the antibodies and antigen-binding fragments thereof provided herein to bind specifically to IFNAR1.

In certain embodiments, the antibody or antigen-binding fragment thereof is capable of specifically binding to a truncated IFNAR1 absent of: a) amino acid residues 32-126 (Subdomain 1), b) amino acid residues 331-432 (Subdomain 4), or both a) and b). Subdomain 1, Subdomain 4, or both are not required (or even dispensable) for IFNAR1 specific binding of the antibodies and antigen-binding fragments thereof.

In certain embodiments, the antibody or antigen-binding fragment thereof binds to the truncated IFNAR1 absent of Subdomain 1, Subdomain 4 or both, at a binding capacity comparable to that of the full-length IFNAR1.

"Binding capacity" as used herein refers to ability of molecule (such as an antibody) to bind to another molecule (such as an antigen). The capacity can be measured by, for example, binding activity to the antigen of interest using any suitable binding assays known in the art. For example, the antibody of interest can be labeled to allow direct quantification of binding activity to the antigen. For another example, the binding activity of an antibody of interest (i.e. primary antibody) to its antigen can also be detected by using a labeled secondary antibody (e.g. an anti-species antibody), which detects the complex of the primary antibody bound to its antigen by binding to the primary antibody in the complex, and therefore indirectly quantifies the binding activity. The labeled antibody can be detected by for example, Enzyme-Linked ImmunoSorbent Assay (ELISA, e.g. where the label is an enzyme), flow cytometry (e.g. where the label is fluorescence), Western blot (e.g. where the label is fluorescence or radioligand), a colorimetric method, a chemiluminescence-based method etc.

The binding capacities to different antigens are considered comparable if the binding activities to the different antigens are no more than 20% different (e.g. no more than 15%, 10%, 8%, 5%), as detected under equivalent assay conditions. "Equivalent assay conditions" as used herein refers to the same assay type, tested at the same or equivalent concentrations of the antibody or the antigen, relative to the same or equivalent controls, detected at the same or equivalent conditions etc.

The antibodies and antigen-binding fragments provided herein do not inhibit IFNβ-mediated IFNAR1 activation. IFNβ, like other IFN-Is such as IFNα and IFNω, can bind to IFNAR1 and induce IFNAR1 activation. "IFNB-mediated IFNAR1 activation" as used herein means IFNAR1 activation mediated or in response to the presence of IFNβ. Many assays can be used to determine IFNAR1 activation. Non-limiting examples include, Daudi cell proliferation, activation of Interferon Stimulated Response Element (ISRE) linked reporter gene expression, IFN-Is effector gene (e.g. mx2 and isg15) expression, IP-10 expression by peripheral blood mononuclear cells (PBMCs), dendritic cells development, and anti-viral activity, determined in the presence of an interested IFN-I, or in the presence of a biological sample containing one or more IFN-Is (such as a plasma sample from an SLE patient). Accordingly, IFNβ-mediated IFNAR1 activation can be determined using any suitable assays for IFNAR1 activation, in the presence of IFNβ versus in the absence thereof.

An antibody or antigen-binding fragment that "do not inhibit IFNβ-mediated IFNAR1 activation" is one that exhibits less than 20% inhibition on the level of IFNβ-mediated IFNAR1 activation as measured in the absence of an antibody or in the presence of an equivalent concentration of a control antibody (such as an isotype control antibody that does not bind to IFNβ) under equivalent assay conditions. A control antibody can be any antibody that is known not to interfere with IFNβ-mediated IFNAR1 activation. This can include for example, antibodies that do not bind to IFNAR1 and IFNβ.

In certain embodiments, the antibody or antigen-binding fragment thereof provided herein inhibits no more than 20%, no more than 15%, no more than 10%, no more than 8%, no more than 5%, no more than 2%, or no more than 1% of the IFNB-mediated IFNAR1 activation in a suitable IFNAR1 activation assay as compared to baseline IFNβ-mediated IFNAR1 activation measured in the absence of an antibody or in the presence of an equivalent concentration of a control antibody (such as an isotype control antibody that does not bind to IFNAR1) under equivalent assay settings.

In certain embodiments, the IFNAR1 activation assay is an IFN-I reporter assay, for example, as described in PCT publication WO2018/010140. In brief, a reporter cell line is constructed by making a reporter gene (such as Green Fluorescent Protein, GFP) under the control of a promoter of IFN effector genes such as mx2 and isg 15. In the presence of IFN-I (e.g. IFNβ), the IFNAR1 will be activated and this will subsequently lead to activation of mx2 or isg 15 promoter, which then initiates expression of the reporter gene. The reporter gene signal can be analyzed by a convenient method, such as flow cytometry. The intensity of the reporter gene signal or the number of cells positive for reporter gene signal can indicate the level of IFNAR1 activation. An antibody or antigen-binding fragment thereof that inhibits IFNAR1 activation mediated by an IFN-I or binding of the IFN-I to IFNAR1 inhibits more IFNAR1 activation signal mediated by the IFN-I, compared to the baseline level of activation signal inhibition measured in the absence of an antibody or in the presence of an equivalent concentration of a control antibody (such as an isotype control antibody) under equivalent assay conditions.

In certain embodiments, the antibody or antigen-binding fragment thereof provided herein inhibits IFNα- and/or IFNω-mediated IFNAR1 activation. "IFNα-mediated IFNAR1 activation" and "IFNω-mediated IFNAR1 activation" as used herein respectively mean IFNAR1 activation mediated or in response to the presence of IFNα or IFNω. Similarly, the IFNα- and/or IFNω-mediated IFNAR1 activation can be determined by any assays suitable for determining IFNAR1 activation as described above, in the presence of IFNα and IFNω, respectively, versus in the absence thereof.

In certain embodiments, the antibody or antigen-binding fragment thereof inhibits at least about 30%, at least about 40%, at least about 50%, or at least about 70%, or at least about 80%, or at least about 90%, or at least about 95%, or at least about 99%, or about 100% of the IFNα- and/or IFN-mediated IFNAR1 activation in a suitable IFNAR1 activation assay as compared to baseline IFNα- and/or IFNω-mediated IFNAR1 activation, respectively, as measured in the absence of an antibody or in the presence of an equivalent concentration of a control antibody (such as an isotype control antibody that does not bind to IFNAR1) under equivalent assay conditions. Such a control antibody can be any antibody that is known not to interfere with IFNα- and/or IFNω-mediated IFNAR1 activation. This can include for example, antibodies that do not bind to IFNAR1, IFNα- and IFNω.

In certain embodiments, the antibodies or antigen-binding fragments thereof provided herein do not inhibit IFNβ-mediated anti-viral activity.

The term "anti-viral activity" mediated by an interferon as used herein refers to the ability of the interferon to reduce virus activity, for example, infectivity, replication, or viability of a virus. Inhibition of anti-viral activity may be determined using any suitable methods known in the art. An exemplary method involves, in general, incubating pre-seeded IFNAR1-expressing cells with an interferon of interest (e.g. IFNβ) in the presence of the test antibody or antigen-binding fragment thereof for one day for example, following by virus challenge for another day, and then determining the anti-viral activity by quantifying the amount of the remaining viable cells in the culture, quantifying the virus titer in the culture after lysing the cells, or quantifying the plaques formed on the infected cells. Another exemplary method involves incubating cells containing a reporter gene construct, such as SINV-Luc (J Virol. 2016 Oct. 28; 90 (22): 10247-10258.) and Flu-Luc (J Thorac Dis. 2018 July; 10 (Suppl 19): S2230-S2237.), such that if the cells are infected by the virus, the reporter gene expression will be induced.

In certain embodiments, the antibodies and antigen-binding fragments thereof exhibit similar or approximately the same level of IFNβ-mediated anti-viral activity as that measured in the absence of an antibody or in the presence of an equivalent concentration of a control antibody (such as an isotype control antibody that does not bind to IFNAR1) in the same type of viral activity assay under equivalent assay conditions.

In certain embodiments, the antibody or antigen-binding fragment thereof provided herein inhibits no more than 20%, no more than 15%, no more than 10%, no more than 8%, no more than 5%, no more than 2%, or no more than 1% of the IFNβ-mediated anti-viral activity in a suitable anti-viral assay as compared to baseline IFNβ-mediated anti-viral activity measured in the presence of an equivalent concentration of control antibody under equivalent assay conditions.

In certain embodiments, the antibodies or antigen-binding fragments thereof provided herein inhibit IFNα- and/or IFNω-mediated anti-viral activity.

In certain embodiments, the antibodies or antigen-binding fragments thereof inhibit at least about 30%, at least about 40%, at least about 50%, or at least about 70%, or at least about 80%, or at least about 90%, or at least about 95%, or at least about 99%, or about 100% of the IFNα- and/or IFNω-mediated anti-viral activity in a suitable anti-viral assay as compared to baseline IFNα- and/or IFNω-mediated anti-viral activity, respectively, as measured in the presence of an equivalent concentration of control antibody under equivalent assay conditions.

In certain embodiments, the inhibition effects of the antibody or antigen-binding fragment thereof provided herein on IFNα- or on IFNω-mediated IFNAR1 activation or on IFNα- or on IFNω-mediated anti-viral activity is at least four, five, six, seven, eight, nine, ten, eleven, twelve, thirteen, fourteen, fifteen, or twenty times higher than that on IFNβ-mediated IFNAR1 activation or on IFNβ-mediated antiviral activity, respectively. The inhibition effects of the antibody or antigen-binding fragment thereof provided herein on IFNα-, IFNω-, and IFNβ-mediated IFNAR1 activation or antiviral activity are measured under equivalent assay conditions, such as but not limited to, using the same type of assay, using equivalent assay parameters, using the same or equivalent concentrations of the test antibodies, and using the same or equivalent amount of the IFNAR1-expressing cells. In certain embodiments, the inhibition effects on IFNα-, IFNω-, or IFNβ-mediated IFNAR1 activation or antiviral activity are measured in the presence of 1 ng/mL IFNα, 50 μg/ml IFNω, or 50 μg/ml IFNβ, respectively.

Without wishing to be bound to any theory, it is believed that the antibodies and antigen-binding fragments thereof are particularly advantageous in providing preferential inhibition of both IFNα- and IFNω-mediated IFNAR1 activation, and minimizing the inhibition on IFNβ-mediated IFNAR1 activation.

Both IFNα and IFNω are reported to be induced in the pathology of type I IFN-related diseases such as systemic lupus erythematosus (SLE). IFNω expression is upregulated in SLE patients at RNA level (Yao Y et al, Hum Genomics Proteomics 2009). IFN-@ is part of the active type I IFN milieu that induces an IFN signature in SLE. It has been reported that, co-inhibition of both IFNω and IFNα resulted in more pronounced suppression of the IFN signature perpetuated in the blood of SLE patients than an IFNα or IFNω inhibitor alone (see details in the US patent No. U.S. Pat. No. 9,902,770B2). Similarly, by inhibiting both the IFNα- and IFNω-mediated IFNAR1 activation, the antibodies and antigen-binding fragments thereof provided herein are also expected to provide therapeutic benefits better than an IFNω antibody or an IFNα antibody alone.

Although IFNβ is equally potent in activating early transcriptional responses as IFNα or IFNω (Coelho L F et al. Proc Natl Acad Sci USA. 2005 Aug. 16; 102 (33): 11917-22.), IFNβ has minimal involvement in pathogenesis of some type I IFN-related diseases. This suggests that IFNβ inhibition can have very limited therapeutic effects on these IFN-related diseases.

On the other hand, IFNβ exhibits much greater potency than IFNα or IFNω in inhibiting monocyte differentiation, inhibiting viral replication, inducing apoptosis of human tumoral cells and the like. These IFNB-mediated effects are in fact beneficial in many circumstances to the well-being of the subject, and therefore would be better not to be inhibited. Therefore, the antibodies and antigen-binding fragments thereof as provided herein provide additional advantages by not inhibiting IFNβ-mediated IFNAR1 activation.

The distinct functions of IFNβ, at least partially, is due to the substantially higher 'integral' affinity to the cell surface receptor of IFNβ compared with IFNα or IFNω. The total buried surface area of the IFNAR1-IFNβ complex amounting to 3,300 $Å^2$ is more substantial than that of the IFNAR1-IFNα2 interface totaling 2,030 $Å^2$ (2,200 $Å^2$ for IFNω). Accordingly, this increased binding interface accounts for approximately 100-fold increase in binding affinity of IFNAR1 to IFNβ compared with IFNα or IFNω (de Weerd N A et al, Nat Immunol 14:901-7 (2013)). The distinct functions of IFNβ is also contributable to the fact that IFNβ, but not IFNα or IFNω, binds to IFNAR1 in an IFNAR2-independent manner, and that the IFNAR1-IFNβ complex transduces signals in a more efficient way. Accordingly, the unique functional characteristic of the antibodies provided herein also implies that they have unique binding sites and binding characteristic which are advantageous over the antibodies known in the art.

Specific Anti-IFNAR1 Antibodies

In certain embodiments, the present disclosure provides anti-IFNAR1 antibodies (e.g. anti-human IFNAR1 antibodies) and antigen-binding fragments thereof comprising one or more (e.g. 1, 2, 3, 4, 5, or 6) CDR comprising the sequences selected from the group consisting of: $SX_1WX_{19}N$ (SEQ ID NO:1), $KIDPSDSEX_2X_{20}X_{21}NQKFX_{22}D$ (SEQ ID NO:2), $GGX_{31}X_4X_5DYDX_6AX_7DY$ (SEQ ID NO:3), $KX_{23}SEVIYNRLA$ (SEQ ID NO:4), $GATX_{24}LEX_{25}$ (SEQ ID NO:5), and $QQYWX_8X_9PFT$ (SEQ ID NO:6), wherein $X_1$ is Y or F, $X_2$ is T or I, $X_3$ is R or G, $X_4$ is S or Y, $X_5$ is F or Y, $X_6$ is A or G, $X_7$ is L or M, $X_8$ is N or S, $X_9$ is K or S, $X_{19}$ is M or L, $X_{20}$ is H or R, $X_{21}$ is F or Y, $X_{22}$ is R or K, $X_{23}$ is S or A, $X_{24}$ is T or S, $X_{25}$ is S or T. In certain embodiments, the present disclosure further encompass antibodies and antigen binding fragments having no more than one, two or three amino acid residue substitution to any of SEQ ID NOs: 1-6, wherein $X_1$ is Y or F, $X_2$ is T or I, $X_3$ is R or G, $X_4$ is S or Y, $X_5$ is F or Y, $X_6$ is A or G, $X_7$ is L or M, $X_8$ is N or S, $X_9$ is K or S, $X_{19}$ is M or L, $X_{20}$ is H or R, $X_{21}$ is F or Y, $X_{22}$ is R or K, $X_{23}$ is S or A, $X_{24}$ is T or S, $X_{25}$ is S or T.

"7G4" as used herein refers to a monoclonal antibody having a heavy chain variable region having the sequence of SEQ ID NO: 7, and a light chain variable region having the sequence of SEQ ID NO: 8.

"10C5" as used herein refers to a monoclonal antibody having a heavy chain variable region having the sequence of SEQ ID NO: 9, and a light chain variable region having the sequence of SEQ ID NO: 10.

In certain embodiments, the present disclosure provides anti-IFNAR1 antibodies and antigen-binding fragments thereof comprising one or more (e.g. 1, 2, 3, 4, 5, or 6) CDR sequences of Antibody 7G4 or Antibody 10C5.

In certain embodiments, the present disclosure provides anti-IFNAR1 antibodies and antigen-binding fragments thereof comprising HCDR1 comprising the sequence of SEQ ID NO: 21, HCDR2 comprising the sequence of SEQ ID NO: 22, and HCDR3 comprising the sequence of SEQ ID NO: 23 or SEQ ID NO: 65, and/or LCDR1 comprising the sequence of SEQ ID NO: 70, LCDR2 comprising the sequence of SEQ ID NO: 71 or SEQ ID NO: 66, and LCDR3 comprising the sequence of SEQ ID NO: 24.

In certain embodiments, the present disclosure provides anti-IFNAR1 antibodies and antigen-binding fragments thereof comprising HCDR1 comprising the sequence of SEQ ID NO: 25, HCDR2 comprising the sequence of SEQ ID NO: 26, and HCDR3 comprising the sequence of SEQ ID NO: 27, and/or LCDR1 comprising the sequence of SEQ ID NO: 72, LCDR2 comprising the sequence of SEQ ID NO: 66, and LCDR3 comprising the sequence of SEQ ID NO: 28.

Table 1 below shows the CDR sequences of antibodies 7G4 and 10C5. Table 2 below shows the heavy chain and light chain variable region amino acid sequences of 7G4 and 10C5, and Table 3 below shows the nucleic acid sequences encoding the variable regions.

TABLE 1

CDR amino acid sequences of 7G4 and 10C5

| | | CDR1 | CDR2 | CDR3 |
|---|---|---|---|---|
| 7G4 | HCDR | SEQ ID NO: 21<br>SYWMN | SEQ ID NO: 22<br>KIDPSDSETHF<br>NQKFRD | SEQ ID NO: 23<br>GGRISFDYDA<br>ALDY<br>CDR3 mutant<br>SEQ ID NO: 65<br>GGRISFDYDG<br>ALDY |
| | LCDR | SEQ ID NO: 70<br>KSSEVIYNRLA | SEQ ID NO: 71<br>GATTLES<br>CDR2 mutant<br>SEQ ID NO: 66<br>GAT SLET | SEQ ID NO: 24<br>QQYWNKPFT |
| 10C5 | HCDR | SEQ ID NO: 25<br>SFWLN | SEQ ID NO: 26<br>KIDPSDSEIRY<br>NQKFKD | SEQ ID NO: 27<br>GGGIYYDYD<br>GAMDY |
| | LCDR | SEQ ID NO: 72<br>KASEVIYNRLA | SEQ ID NO: 66<br>GATSLET | SEQ ID NO: 28<br>QQYWSSPFT |

TABLE 2

Variable region amino acid sequences of 7G4 and 10C5

| | VH | VL |
|---|---|---|
| 7G4 | SEQ ID NO: 7<br>QVQLQQPGAELVKPGAPVKLS<br>CKASGYTFTSYWMNWVRQRP<br>GRGLEWIGKIDPSDSETHFNQK<br>FRDKATLTVDKSSTTAYIQLSS<br>LTSEDSAVYYCARGGRISFDYD<br>AALDYWGQGTSVTVSS | SEQ ID NO: 8<br>DILMTQSSSSFSVSLGDRVTITC<br>KSSEVIYNRLAWFQQKPGNAPRL<br>LISGATTLESGFPSRFSGSGSGK<br>DYTLSITSLQIEDVSTYYCQQYW<br>NKPFTFGSGTKLEVK |
| 10C5 | SEQ ID NO: 9<br>QVQLQQPGTELVKPGSPVKLSC<br>KASGYTFTSFWLNWVQQRPGR<br>GLEWIGKIDPSDSEIRYNQKFK<br>DKATLTVDKSSNTAYIQLSSLT<br>SEDSAVYYCARGGGIYYDYDG<br>AMDYWGQGTSVTVSS | SEQ ID NO: 10<br>DIQMTQSSSSFSVSLGDRLTITC<br>KASEVIYNRLAWFQQKPGNAPRL<br>LISGATSLETGVPSRFSGSGSRK<br>DYTLSISSLQTEDVATYYCQQYW<br>SSPFTFGSGTKLEIK |

TABLE 3

Nucleotide sequences encoding the variable reqions of 7G4 and 1005

| | VHnu | VLnu |
|---|---|---|
| 7G4 | SEQ ID NO: 11<br>CAGGTCCAACTGCAGCAGCCT<br>GGGGCTGAGCTTGTGAAGCCT<br>GGGGCTCCAGTGAAACTGTCC<br>TGCAAGGCTTCTGGCTACACC<br>TTCACCAGCTACTGGATGAAC<br>TGGGTGAGGCAGAGGCCTGGA<br>CGAGGCCTCGAGTGGATTGGA<br>AAGATTGATCCTTCCGATAGT<br>GAAACTCACTTCAATCAAAAG<br>TTCAGGGACAAGGCCACACTG<br>ACTGTAGACAAATCCTCCACC<br>ACAGCCTACATCCAACTCAGC<br>AGCCTGACATCTGAGGACTCT<br>GCGGTCTATTACTGTGCAAGA<br>GGGGGGAGGATCTCCTTTGAT<br>TACGACGCTGCTTTGGACTAC<br>TGGGGTCAAGGAACCTCAGTC<br>ACCGTATCCTCA | SEQ ID NO: 12<br>GACATCCTGATGACACAGTCTTC<br>ATCCTCCTTTTCTGTATCTTTAG<br>GAGACAGAGTCACCATTACTTGC<br>AAATCAAGTGAGGTCATATATAA<br>TCGGTTAGCCTGGTTTCAGCAGA<br>AACCAGGAAATGCTCCTAGGCTC<br>TTAATATCTGGTGCGACCACTTT<br>GGAATCTGGGTTTCCTTCAAGAT<br>TCAGTGGCAGTGGATCTGGAAAG<br>GATTACACTCTCAGCATTACCAG<br>TCTTCAGATTGAAGATGTTTCTA<br>CTTATTACTGTCAACAGTATTGG<br>AATAAGCCATTCACGTTCGGCTC<br>GGGGACAAAGTTGGAAGTAAAA |
| 10C5 | SEQ ID NO: 13<br>CAGGTCCAACTACAGCAGCCT<br>GGGACTGAGCTTGTGAAGCCT<br>GGGTCTCCAGTGAAACTGTCC<br>TGCAAGGCTTCTGGCTACACC<br>TTCACCAGCTTCTGGTTGAAC<br>TGGGTGCAACAGAGGCCTGGA<br>CGAGGCCTCGAATGGATTGGA<br>AAGATTGATCCTTCCGATAGT<br>GAAATTCGCTACAATCAAAAG<br>TTCAAGGACAAGGCCACACTG<br>ACTGTAGACAAATCGTCCAAC<br>ACAGCCTACATCCAACTCAGC<br>AGCCTGACATCTGAGGACTCT<br>GCGGTCTATTACTGTGCAAGA<br>GGGGGGGGGATCTACTATGAT<br>TACGACGGCGCTATGGACTAC<br>TGGGGTCAAGGAACCTCAGTC<br>ACCGTATCCTCA | SEQ ID NO: 14<br>GACATCCAGATGACACAATCTTC<br>ATCCTCCTTTTCTGTATCTCTAG<br>GAGACAGACTCACCATTACTTGC<br>AAGGCAAGTGAGGTCATATATAA<br>TCGATTAGCCTGGTTTCAGCAGA<br>AACCAGGAAATGCTCCTAGGCTC<br>TTAATATCTGGTGCAACCAGTTT<br>GGAAACTGGGGTGCCTTCAAGAT<br>TCAGTGGCAGTGGATCTAGAAAG<br>GATTACACTCTCAGCATTTCCAG<br>TCTTCAGACTGAAGATGTTGCTA<br>CTTATTACTGTCAACAGTATTGG<br>AGTTCTCCATTCACGTTCGGCTC<br>GGGGACAAAGTTGGAAATAAAA |

The present disclosure also provides the hybridoma cells expressing 7G4 and 10C5 respectively, which have been deposited with China General Microbiological Culture Collection Center (CGMCC).

The detailed deposit information of hybridoma producing 7G4 is as follows: Microorganism Deposit No.: CGMCC No. 16286; Taxonomic Name: hybridoma cell line; Deposit Address: Building 1, No. 1 Beichen West Road, Chaoyang District, Beijing; Deposit Unit: China General Microbiological Culture Collection Center; and Deposit Date: Aug. 27, 2018.

The detailed deposit information of hybridoma producing 10C5 is as follows: Microorganism Deposit No.: CGMCC No. 16287; Taxonomic Name: hybridoma cell line; Deposit Address: Building 1, No. 1 Beichen West Road, Chaoyang District, Beijing; Deposit Unit: China General Microbiological Culture Collection Center; and Deposit Date: Aug. 27, 2018.

The present disclosure also provides antibodies expressed from the hybridoma cell having a deposit number of CGMCC deposit No. 16286, or from the hybridoma cell having a deposit No. 16287, and the antigen binding fragments thereof.

Given that each of 7G4 and 10C5 can bind to IFNAR1 and that antigen-binding specificity is provided primarily by the CDR1, CDR2 and CDR3 regions, the HCDR1, HCDR2 and HCDR3 sequences and LCDR1, LCDR2 and LCDR3 sequences of 7G4 and 10C5 can be "mixed and matched" (i.e., CDRs from different antibodies can be mixed and matched, but each antibody must contain a HCDR1, HCDR2 and HCDR3 and a LCDR1, LCDR2 and LCDR3) to create anti-IFNAR1 binding molecules of the present disclosure. IFNAR1 binding of such "mixed and matched" antibodies can be tested using the binding assays described above and in the Examples. Preferably, when VH CDR sequences are mixed and matched, the HCDR1, HCDR2 and/or HCDR3 sequence from a particular VH sequence is replaced with a structurally similar CDR sequence(s). Likewise, when VL CDR sequences are mixed and matched, the LCDR1, LCDR2 and/or LCDR3 sequence from a particular VL sequence preferably is replaced with a structurally similar CDR sequence(s). For example, the VH HCDR1s of 7G4 and 10C5 share some structural similarity and therefore are amenable to mixing and matching. It will be readily apparent to the ordinarily skilled artisan that novel VH and VL sequences can be created by substituting one or more VH and/or VL CDR region sequences with structurally similar sequences from the CDR sequences disclosed herein for monoclonal antibodies 7G4 and 10C5.

CDRs are known to be responsible for antigen binding. However, it has been found that not all of the 6 CDRs are indispensable or unchangeable. In other words, it is possible to replace or change or modify one or more CDRs in anti-IFNAR1 antibodies 7G4 or 10C5, yet substantially retain the specific binding affinity to IFNAR1.

In certain embodiments, the anti-IFNAR1 antibodies and antigen-binding fragments provided herein comprise a heavy chain CDR3 sequence of antibodies 7G4 or 10C5. In certain embodiments, the anti-IFNAR1 antibodies and antigen-binding fragments provided herein comprise a heavy chain CDR3 sequence selected from the group consisting of SEQ ID NOs: 23, 65 and 27.

In certain embodiments, the antibodies and antigen-binding fragments thereof provided herein comprise suitable framework region (FR) sequences, as long as the antibodies and antigen-binding fragments thereof can specifically bind to IFNAR1. The CDR sequences provided in Table 1 above are obtained from mouse antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain and light chain variable domains can be selected to achieve this purpose using methods known in the art. In an illustrative example, "best-fit" approach can be used, where a non-human (e.g. rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et al. (1992) Proc. Natl. Acad. Sci. USA, 89:4285; Presta et al. (1993) J. Immunol., 151:2623).

In certain embodiments, the humanized antibodies or antigen-binding fragments thereof provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived from different human immunoglobulin genes, for example, FR sequences derived from one human antibody and constant region from another human antibody. In some embodiments, the humanized antibody or antigen-binding fragment comprise human heavy chain HFR1-4, and/or light chain LFR1-4.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure. In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the present disclosure also provides humanized anti-IFNAR1 antibodies and antigen-binding fragments thereof comprising a heavy chain HFR1 comprising the sequence of SEQ ID NO: 33, a heavy chain HFR2 comprising the sequence selected from SEQ ID NOs: 41, 42 and 43, a heavy chain HFR3 comprising the sequence selected from SEQ ID NOs: 44, and 45, and a heavy chain HFR4 comprising the sequence of SEQ ID NO: 36.

In certain embodiments, the present disclosure also provides humanized anti-IFNAR1 antibodies and antigen-binding fragments thereof comprising a light chain LFR1 comprising the sequence of SEQ ID NO: 37, a light chain LFR2 comprising the sequence selected from SEQ ID NOs: 46, 47 and 48, a light chain LFR3 comprising the sequence selected from SEQ ID NOs: 49, and 50, and a light chain LFR4 comprising the sequence of SEQ ID NO: 40.

In certain embodiments, the present disclosure also provides humanized anti-IFNAR1 antibodies and antigen-binding fragments thereof comprising HFR1, HFR2, HFR3, and/or HFR4 sequences contained in a heavy chain variable region selected from a group consisting of: 7G4-g0-VH (SEQ ID NO: 51), 7G4-g1-VH (SEQ ID NO: 52), 7G4-g2-VH (SEQ ID NO: 53), and 7G4-g3-VH (SEQ ID NO: 54).

In certain embodiments, the present disclosure also provides humanized anti-IFNAR1 antibodies and antigen-binding fragments thereof comprising LFR1, LFR2, LFR3, and/or LFR4 sequences contained in a light chain variable region selected from a group consisting of: 7G4-g0-VL (SEQ ID NO: 55), 7G4-g1-VL (SEQ ID NO: 56), 7G4-g1-VL-mut-1 (SEQ ID NO: 68), 7G4-g2-VL (SEQ ID NO: 57), and 7G4-g3-VL (SEQ ID NO: 58).

In certain embodiments, the humanized anti-IFNAR1 antibodies and antigen-binding fragments thereof provided herein comprise a heavy chain variable domain sequence selected from the group consisting of SEQ ID NO: 51, SEQ ID NO: 52, SEQ ID NO: 53, and SEQ ID NO: 54; and/or a light chain variable domain sequence selected from the group consisting of SEQ ID NO: 55, SEQ ID NO: 56, SEQ ID NO: 57, and SEQ ID NO: 58.

The present disclosure also provides exemplary humanized antibodies of 7G4, including:

1) "Hu4-1" comprising the heavy chain variable region of 7G4-g0-VH (SEQ ID NO: 51) and the light chain variable region of 7G4-g0-VL (SEQ ID NO: 55);
2) "Hu4-2" comprising the heavy chain variable region of 7G4-g1-VH (SEQ ID NO: 52), and the light chain variable region of 7G4-g0-VL (SEQ ID NO: 55);
3) "Hu4-3" comprising the heavy chain variable region of 7G4-g2-VH (SEQ ID NO: 53), and the light chain variable region of 7G4-g0-VL (SEQ ID NO: 55);
4) "Hu4-4" comprising the heavy chain variable region of 7G4-g3-VH (SEQ ID NO: 54), and the light chain variable region of 7G4-g0-VL (SEQ ID NO: 55);
5) "Hu4-5" comprising the heavy chain variable region of 7G4-g0-VH (SEQ ID NO: 51), and the light chain variable region of 7G4-g1-VL (SEQ ID NO: 56);
6) "Hu4-6" comprising the heavy chain variable region of 7G4-g1-VH (SEQ ID NO: 52), and the light chain variable region of 7G4-g1-VL (SEQ ID NO: 56);
7) "Hu4-6-mut-1" comprising the heavy chain variable region of 7G4-g1-VH-mut-1 (SEQ ID NO: 67), and the light chain variable region of 7G4-g1-VL (SEQ ID NO: 56);
8) "Hu4-6-mut-2" comprising the heavy chain variable region of 7G4-g1-VH (SEQ ID NO: 52), and the light chain variable region of 7G4-g1-VL-mut-1 (SEQ ID NO: 68);
9) "Hu4-6-mut-3" comprising the heavy chain variable region of 7G4-g1-VH-mut-1 (SEQ ID NO: 67), and the light chain variable region of 7G4-g1-VL-mut-1 (SEQ ID NO: 68);
10) "Hu4-7" comprising the heavy chain variable region of 7G4-g2-VH (SEQ ID NO: 53), and the light chain variable region of 7G4-g1-VL (SEQ ID NO: 56);
11) "Hu4-8" comprising the heavy chain variable region of 7G4-g3-VH (SEQ ID NO: 54), and the light chain variable region of 7G4-g1-VL (SEQ ID NO: 56);
12) "Hu4-9" comprising the heavy chain variable region of 7G4-g0-VH (SEQ ID NO: 51), and a light chain variable region of the light chain variable region of 7G4-g2-VL (SEQ ID NO: 57);
13) "Hu4-10" comprising the heavy chain variable region of 7G4-g1-VH (SEQ ID NO: 52), and a light chain variable region of the light chain variable region of 7G4-g2-VL (SEQ ID NO: 57);
14) "Hu4-11" comprising the heavy chain variable region of 7G4-g2-VH (SEQ ID NO: 53), and the light chain variable region of 7G4-g2-VL (SEQ ID NO: 57);
15) "Hu4-12" comprising the heavy chain variable region of 7G4-g3-VH (SEQ ID NO: 54), and the light chain variable region of 7G4-g2-VL (SEQ ID NO: 57);
16) "Hu4-13" comprising the heavy chain variable region of 7G4-g0-VH (SEQ ID NO: 51), and a light chain variable region of the light chain variable region of 7G4-g3-VL (SEQ ID NO: 58);
17) "Hu4-14" comprising the heavy chain variable region of 7G4-g1-VH (SEQ ID NO: 52), and the light chain variable region of 7G4-g3-VL (SEQ ID NO: 58);
18) "Hu4-15" comprising the heavy chain variable region of 7G4-g2-VH (SEQ ID NO: 53), and the light chain variable region of 7G4-g3-VL (SEQ ID NO: 58);
19) "Hu4-16" comprising the heavy chain variable region of 7G4-g3-VH (SEQ ID NO: 54), and the light chain variable region of 7G4-g3-VL (SEQ ID NO: 58).

These exemplary humanized anti-IFNAR1 antibodies retained the specific binding capacity or affinity to IFNAR1, and are at least comparable to, or even better than, the parent mouse antibody 7G4 in that aspect. For example, data is provided in Example 9.

Antibodies Derived from Rearrangements of Gene Segments

In certain embodiments, the antibody or antigen-binding fragment thereof provided herein comprises a heavy chain variable region from particular mouse germline heavy chain Ig genes comprising a V gene that is the product of or derived from a mouse IGHV1-69 gene, a D gene that is the product of or derived from a mouse IGHD2-4 gene, and a J gene that is the product of or derived from a mouse IGHJ4 gene, and/or a light chain variable region from particular mouse germline light chain Ig genes comprising a V gene that is the product of or derived from a mouse IGKV13-84 gene, and a J gene that is the product of or derived from a mouse IGKJ4 gene.

An antibody or antigen-binding fragment thereof that is "a product of" or "derived from" a particular mouse germline immunoglobulin gene sequences may contain one or more amino acid residue differences as compared to the germline immunoglobulin sequence, due to, for example, naturally-occurring somatic mutations or intentional introduction of site-directed mutation. However, a selected antibody or antigen-binding fragment thereof provided herein typically is at least 75% (e.g. at least 80%, at least 85%) identical in amino acids sequence to an amino acid sequence encoded by a mouse germline immunoglobulin gene and may contain amino acid residues that identify the antibody or antigen-binding fragment thereof as being mouse or human when compared to the germline immunoglobulin amino acid sequences of other species (e.g. rat germline sequences).

The exemplary mouse antibodies 7G4 and 10C5 are both derived from the mouse germline Ig genes including IGHV1-69 gene, IGHD2-4 gene, and IGHJ4 gene for the heavy chain variable region; and from IGKV13-84 gene and IGKJ4 gene for the light chain variable region. Without wishing to be bound by any theory, it is believed that this combination of mouse genes, upon rearrangement, are biased in favor of producing combinations of VH and VL which can assemble into anti-IFNAR1 antibodies having the similar binding capacity, binding characteristics and/or biological activity to 7G4 and 10C5 as disclosed herein.

A skilled person in the art can obtain an anti-IFNAR1 antibody derived from the mouse germline Ig genes including IGHV1-69 gene, IGHD2-4 gene, IGHJ4 gene, IGKV13-84 gene and IGKJ4 gene, using methods known in the art, such as for example, by using phage display libraries, by artificial mutation of the gene sequences, or using transgenic animals. In one embodiment, the mouse genes can be cloned and recombined into phage display libraries, followed by panning or screening of the phage clones capable of binding to the antigen of interest (e.g. IFNAR1) (for example, as described in Winter et al., Ann. Rev Immunol., 12:433-455 (1994)). In another embodiment, the gene sequences of IGHV1-69, IGHD2-4, IGHJ4, IGKV13-84 and IGKJ4 genes can be engineered to introduce one or more mutations, such that the encoded heavy or light chain variable region sequences are at least 75% (e.g. at least 80%, at least 85%) identical in amino acids sequence to SEQ ID NO: 15 (heavy chain) or to SEQ ID NO: 16 (light chain). In another embodiment, a transgenic animal which lacks the endogenous antibody producing genes, can be engineered to carry the specific combination of the mouse IGHV1-69 gene, IGHD2-4 gene, IGHJ4 gene, IGKV13-84 gene and IGKJ4 gene, where upon immunization against the antigen of interest (e.g. IFNAR1), the transgenic animal is prone to produce anti-IFNAR1 antibodies from these engineered mouse genes which are likely to give rise to anti-IFNAR1 antibodies.

In some embodiments, the anti-IFNAR1 antibodies and antigen-binding fragments provided herein comprise all or a portion of the heavy chain variable domain and/or all or a portion of the light chain variable domain. In one embodiment, the anti-IFNAR1 antibodies and antigen-binding fragments provided herein is a single domain antibody which consists of all or a portion of the heavy chain variable domain provided herein. More information of such a single domain antibody is available in the art (see, e.g. U.S. Pat. No. 6,248,516).

In certain embodiments, the anti-IFNAR1 antibodies and the fragments thereof provided herein further comprise an immunoglobulin (Ig) constant region, which optionally further comprises a heavy chain and/or a light chain constant region. In certain embodiments, the heavy chain constant region comprises CH1, hinge, and/or CH2-CH3 regions (or optionally CH2-CH3-CH4 regions). In certain embodiments, the anti-IFNAR1 antibodies and the fragments thereof provided herein comprises heavy chain constant regions of human IgG1, IgG2, IgG3, or IgG4. In certain embodiments, the light chain constant region comprises CK or CA. The constant region of the anti-IFNAR1 antibodies and the fragments thereof provided herein may be identical to the wild-type constant region sequence or be different in one or more mutations.

In certain embodiments, the heavy chain constant region comprises an Fc region. Fc region is known to mediate effector functions such as ADCC and CDC of the antibody. Fc regions of different Ig isotypes have different abilities to induce effector functions. For example, Fc regions of IgG1 and IgG3 have been recognized to induce both ADCC and CDC more effectively than those of IgG2 and IgG4. In certain embodiments, the anti-IFNAR1 antibodies and antigen-binding fragments thereof provided herein comprises an Fc region of IgG1 or IgG3 isotype, which could induce ADCC or CDC; or alternatively, a constant region of IgG4 or IgG2 isotype, which has reduced or depleted effector function. In certain embodiments, the anti-IFNAR1 antibodies or antigen-binding fragments thereof comprises a wild type human IgG1 Fc region comprising the sequence of SEQ ID NO: 61 or other wild type human IgG1 alleles.

In certain embodiments, the antibodies and the fragments thereof provided herein have a specific binding affinity to human IFNAR1 which is sufficient to provide for diagnostic and/or therapeutic use.

The antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

In certain embodiments, the present application provides an anti-IFNAR1 antibody or antigen-binding fragment thereof, which competes for binding to IFNAR1 with the antibody or antigen-binding fragment thereof provided herein, and wherein the antibody or antigen-binding fragment thereof does not inhibit IFNβ-mediated IFNAR1 activation. In certain embodiments, the antibody or antigen-binding fragment thereof inhibits IFNα- and/or IFNω-mediated IFNAR1 activation. Such an antibody or antigen-binding fragment thereof can sufficiently inhibit IFNAR1 activation, while retaining desirable bioactivity of IFNβ such as inhibition of viral replication. In certain embodiments, the antibody or antigen-binding fragment thereof of provided herein, have inhibition effects on IFNα- or on IFNω-mediated IFNAR1 activation or the anti-viral activity is at least four, five, six, seven, eight, nine, ten, eleven, twelve, thirteen, fourteen, fifteen, or twenty times higher than that on IFNβ-mediated IFNAR1 activation.

Antibody Variants

The antibodies and antigen-binding fragments thereof provided herein also encompass various variants thereof.

In certain embodiments, the antibody variants comprise one or more modifications or substitutions in one or more CDR sequences as provided in Table 1 above, one or more variable region sequences (but not in any of the CDR sequences) provided in Table 2 above, and/or the constant region (e.g. Fc region). Such variants retain binding specificity to IFNAR1 of their parent antibodies, but have one or more desirable properties conferred by the modification(s) or substitution(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g. charged residues such as Arg, Asp, His, Lys, and Glu) can be identified and replaced by a neutral or negatively charged amino acid (e.g. alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences as provided in Table 1 above, one or more FR sequences provided herein, or the heavy or light chain variable region sequences provided in Table 2 above. FR sequences can be readily identified by a skilled person in the art based on the CDR sequences in Table 1 above and variable region sequences in Table 2 above, as it is well-known in the art that a CDR region is flanked by two FR regions in the variable region. The affinity variants retain specific binding affinity to IFNAR1 of the parent antibody, or even have improved IFNAR1 specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and variable region sequences provided in Table 1 above and Table 2 above, one or more amino acid residues may be substituted yet the resulting antibody or antigen-binding fragment still retain the binding affinity or binding capacity to IFNAR1, or even have an improved binding affinity or capacity. Various methods known in the art can be used to achieve this purpose. For example, a library of antibody variants (such as Fab or scFv variants) can be generated and expressed with phage display technology, and then screened for the binding affinity to human IFNAR1. For another example, computer software can be used to virtually simulate the binding of the antibodies to human IFNAR1, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody or antigen-binding fragment provided herein comprises one or more amino acid residue substitutions in one or more CDR sequences, and/or one or more FR sequences. In certain embodiments, an affinity variant comprises no more than 20, 15, 10, 9, 8, 7, 6, 5, 4, 3, 2, or 1 substitutions in the CDR sequences and/or FR sequences in total.

In certain embodiments, the anti-IFNAR1 antibodies and antigen-binding fragments thereof comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1 above, and in the meantime retain the binding affinity to IFNAR1 at a level similar to or even higher than its parent antibody.

In certain embodiments, the anti-IFNAR1 antibodies and antigen-binding fragments thereof comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2 above, and in the meantime retain the binding affinity to IFNAR1 at a level similar to or even higher than its parent antibody. In some embodiments, a total of 1 to 10 amino acids have been substituted, inserted, or deleted in a variable region sequence listed in Table 2 above. In some embodiments, the substitutions, insertions, or deletions occur in regions outside the CDRs (e.g. in the FRs).

Glycosylation Variant

The anti-IFNAR1 antibodies and antigen-binding fragments provided herein also encompass a glycosylation variant, which can be obtained to either increase or decrease the extent of glycosylation of the antibody or antigen binding fragment.

The antibody or antigen binding fragment thereof may comprise one or more modifications that introduces or removes a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

In certain embodiments, the anti-IFNAR1 antibodies and antigen-binding fragments provided herein comprise a mutation at N297 (e.g. N297A, N297Q, or N297G) to remove the glycosylation site.

Cysteine-Engineered Variant

The anti-IFNAR1 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments thereof to introduce free cysteine residues are known in the art, see, for example, WO2006/034488.

Fc Variant

The anti-IFNAR1 antibodies and antigen-binding fragments provided herein also encompass an Fc variant, which comprises one or more amino acid residue modifications or substitutions at its Fc region and/or hinge region, for example, to provide for altered effector functions such as ADCC and CDC. Methods of altering ADCC activity by antibody engineering have been described in the art, see for example, Shields R L. et al., J Biol Chem. 2001. 276 (9): 6591-604; Idusogie E E. et al., J Immunol. 2000.164 (8): 4178-84; Steurer W. et al., J Immunol. 1995, 155 (3): 1165-74; Idusogie E E. et al., J Immunol. 2001, 166 (4): 2571-5; Lazar G A. et al., PNAS, 2006, 103 (11): 4005-4010; Ryan M C. et al., Mol. Cancer Ther., 2007, 6:3009-3018; Richards J O, et al., Mol Cancer Ther. 2008, 7 (8): 2517-27; Shields R. L. et al, J. Biol. Chem, 2002, 277: 26733-26740; Shinkawa T. et al, J. Biol. Chem, 2003, 278:3466-3473.

CDC activity of the antibodies provided herein can also be altered, for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fe region variants. One or more amino acids selected from amino acid residues 329, 331 and 322 of the Fc region can be replaced with a different amino acid residue to alter C1q binding and/or reduced or abolished complement dependent cytotoxicity (CDC) (see, U.S. Pat. No. 6,194,551 by Idusogie et al). One or more amino acid substitution(s) can also be introduced to alter the ability of the antibody to fix complement (see PCT Publication WO 94/29351 by Bodmer et al.).

In certain embodiments, the anti-IFNAR1 antibodies and antigen-binding fragments provided herein has reduced effector functions, and comprise one or more amino acid substitution(s) in IgG1 at a position selected from the group consisting of: 234, 235, 237, and 238, 268, 297, 309, 330, and 331. In certain embodiments, the anti-IFNAR1 antibodies and antigen-binding fragments provided herein is of IgG1 isotype and comprises one or more amino acid substitution(s) selected from the group consisting of: N297A, N297Q, N297G, L235E, L234A, L235A, L234F, L235E, P331S, and any combination thereof. In certain embodiments, the anti-IFNAR1 antibodies and antigen-binding fragments provided herein is of IgG2 isotype, and comprises one or more amino acid substitution(s) selected from the group consisting of: H268Q, V309L, A330S, P331S, V234A, G237A, P238S, H268A, and any combination thereof (e.g. H268Q/V309L/A330S/P331S, V234A/G237A/P238S/H268A/V309L/A330S/P331S). In certain embodiments, the anti-IFNAR1 antibodies and antigen-binding fragments provided herein is of IgG4 isotype, and comprises one or more amino acid substitution(s) selected from the group consisting of: N297A, N297Q, N297G, L235E, L234A, L235A, and any combination thereof. In certain embodiments, the anti-IFNAR1 antibodies and antigen-binding fragments provided herein is of IgG2/IgG4 cross isotype. Examples of IgG2/IgG4 cross isotype is described in Rother R P et al, Nat Biotechnol 25:1256-1264 (2007).

In certain embodiments, the anti-IFNAR1 antibodies and antigen-binding fragments provided herein is of IgG1 isotype and comprises one or more amino acid substitution(s) at one or more points of 234, 235 and 331. In certain embodiments, the anti-IFNAR1 antibodies and antigen-binding fragments provided herein is of IgG1 isotype and comprises the triple mutations L234F/L235E/P331S in the Fc region. In certain embodiments, the anti-IFNAR1 antibodies and antigen-binding fragments provided herein comprise a variant Fc region comprising the sequence of SEQ ID NO: 62.

In certain embodiments, the anti-IFNAR1 antibodies and antigen-binding fragments provided herein has increased ADCC and/or increased affinity to Fcγ receptor, and comprises one or more amino acid substitution(s) at one or more of the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (see WO 00/42072 by Presta). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In certain embodiments, the anti-IFNAR1 antibodies or antigen-binding fragments thereof comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al, Structure, 6 (1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70:3269-3277 (2010); and Hinton, P. et al, J. Immunology, 176:346-356 (2006).

In certain embodiments, anti-IFNAR1 antibodies or antigen-binding fragments thereof comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g. as described in U.S. Pat. No. 5,731,168.

Antigen-Binding Fragments

Provided herein are also anti-IFNAR1 antigen-binding fragments. Various types of antigen-binding fragments are known in the art and can be developed based on the anti-IFNAR1 antibodies provided herein, including for example, the exemplary antibodies whose CDR and variable sequences are shown in Tables 1 and 2, and their different variants (such as affinity variants, glycosylation variants, Fc variants, cysteine-engineered variants and so on).

In certain embodiments, an anti-IFNAR1 antigen-binding fragment provided herein is a camelized single domain antibody, a diabody, a single chain Fv fragment (scFv), an scFv dimer, a BsFv, a dsFv, a $(dsFv)_2$, a dsFv-dsFv', an Fv fragment, a Fab, a Fab', a $F(ab')_2$, a bispecific antibody, a ds diabody, a nanobody, a domain antibody, a single domain antibody, or a bivalent domain antibody.

Various techniques can be used for the production of such antigen-binding fragments. Illustrative methods include, enzymatic digestion of intact antibodies (see, e.g. Morimoto et al., Journal of Biochemical and Biophysical Methods 24:107-117 (1992); and Brennan et al., Science, 229:81 (1985)), recombinant expression by host cells such as *E. Coli* (e.g. for Fab, Fv and ScFv antibody fragments), screening from a phage display library as discussed above (e.g. for ScFv), and chemical coupling of two Fab'-SH fragments to form $F(ab')_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxyl terminus to provide for a fusion protein (see, for example, Antibody Engineering, ed. Borrebaeck).

In certain embodiments, the anti-IFNAR1 antibodies and antigen-binding fragments thereof is bispecific. In certain embodiments, the antibody or antigen-binding fragment thereof is further linked to a second functional moiety having a different binding specificity from said IFNAR1 antibody, or antigen binding fragment thereof.

Conjugates

In some embodiments, the anti-IFNAR1 antibodies and antigen-binding fragments thereof further comprise a conjugate moiety. The conjugate moiety can be linked to the antibodies and antigen-binding fragments thereof. A conjugate moiety is a moiety that can be attached to the antibody or antigen-binding fragment thereof. It is contemplated that a variety of conjugate moieties may be linked to the antibodies or antigen-binding fragments thereof provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments thereof by covalent binding, affinity binding, intercalation, coordinate binding, complexation, association, blending, or addition, among other methods.

In certain embodiments, the antibodies and antigen-binding fragments disclosed herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies may be linked to a conjugate moiety indirectly, or through another conjugate moiety. For example, the antibody or antigen-binding fragments thereof may be conjugated to biotin, then indirectly conjugated to a second conjugate that is conjugated to avidin. The conjugate can be a clearance-modifying agent, a toxin (e.g. a chemotherapeutic agent), a detectable label (e.g. a radioactive isotope, a lanthanide, a luminescent label, a fluorescent label, or an enzyme-substrate label), or purification moiety.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, MMAE, MMAF, DM1, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, and anthramycin (AMC)), anti-mitotic agents (e.g. vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moiety, digoxigenin, biotin/avidin, a DNA molecule or gold for detection.

In certain embodiments, the conjugate moiety can be a clearance-modifying agent which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibodies and antigen-binding fragments thereof provided herein is used as a base for a conjugate.

Polynucleotides and Recombinant Methods

The present disclosure provides isolated polynucleotides that encode the anti-IFNAR1 antibodies and antigen-binding fragments thereof. The term "nucleic acid" or "polynucleotide" as used herein refers to deoxyribonucleic acids (DNA) or ribonucleic acids (RNA) and polymers thereof in either single- or double-stranded form. In certain embodiments, the isolated polynucleotides comprise one or more nucleotide sequences as shown in SEQ ID NO: 11, 12, 13, and 14, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions, and encodes the variable region of the exemplary antibodies provided herein. Unless otherwise indicated, a particular polynucleotide sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

DNA encoding the monoclonal antibody is readily isolated and sequenced using conventional procedures (e.g. by using oligonucleotide probes that are capable of binding specifically to genes encoding the heavy and light chains of the antibody). The encoding DNA may also be obtained by synthetic methods.

The isolated polynucleotide that encodes the anti-IFNAR1 antibodies and antigen-binding fragments thereof (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides expression vectors comprising the isolated polynucleotide provided herein. In certain embodiments, the polynucleotide provided herein encodes the antibodies or antigen-binding fragments thereof, at least one promoter (e.g. SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g. herpes simplex virus), poxvirus, baculovirus, papillomavirus, papovavirus (e.g. SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT.RTM., pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment thereof can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g. *E. coli, Enterobacter, Erwinia, Klebsiella, Proteus, Salmonella*, e.g. *Salmonella typhimurium, Serratia*, e.g. *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-IFNAR1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g. *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g. *Neurospora, Penicillium, Tolypocladium*, and *Aspergillus* hosts such as *A. nidulans* and *A. niger.*

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CVI line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4*, Mather, Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is a mammalian cultured cell line, such as CHO, BHK, NS0, 293 and their derivatives.

Host cells are transformed with the above-described expression or cloning vectors for anti-IFNAR1 antibody production and cultured in conventional nutrient media modified as appropriate for inducing promoters, selecting transformants, or amplifying the genes encoding the desired sequences. In another embodiment, the antibody may be produced by homologous recombination known in the art. In certain embodiments, the host cell is capable of producing the antibody or antigen-binding fragment thereof provided herein.

The host cells used to produce the antibodies or antigen-binding fragments thereof provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-IFNAR1 antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available.

Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

Pharmaceutical Composition

The present disclosure further provides pharmaceutical compositions comprising the anti-IFNAR1 antibodies or antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments thereof as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-IFNAR1 antibody or antigen-binding fragment thereof or composition thereof. Overfilling vials with a small amount above that needed for a dose or set of doses (e.g. about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides methods of treating a type I IFN-related disease or condition in a subject, comprising administering a therapeutically effective amount of the antibody or antigen-binding fragment thereof provided herein, or the pharmaceutical composition provided herein to the subject. In certain embodiments, the type I IFN-related disease or condition is IFNα and/or IFN-related disease or condition.

In some embodiment, the type I IFN-related disease or condition is characterized in expressing or over-expressing of type I interferon (IFN) and/or type I IFN signature genes.

The term "signature genes", or "gene signature" or "gene expression signature" as used herein refers to a single or combined group of genes in a cell with a uniquely characteristic pattern of gene expression that occurs as a result of an altered or unaltered biological process or pathogenic medical condition, such as the autoimmune disease. The phenotypes that may theoretically be defined by a gene expression signature range from those that predict the survival or prognosis of an individual with a disease, those that are used to differentiate between different subtypes of a disease, to those that predict activation of a particular pathway. Gene signatures can be ideally used to select a group of patients for whom a particular treatment will be effective.

In certain embodiments, the type I interferon signature genes in a specific disease can be obtained using known methods in the art, such as microarray (see for example, Li et al., Clin Exp Immunol. 2010 March; 159 (3): 281-291; and Harman et al.,, Blood 2011 118:298-308).

Overexpression of IFN-Is or type I IFN signature genes have been documented in several autoimmune diseases, including systemic lupus erythematosus (SLE), myositis, Sjögren's syndrome, rheumatoid arthritis, systemic sclerosis, scleroderma, multiple sclerosis (MS), idiopathic inflammatory myopathies (IIM) and rheumatoid arthritis (RA) (Psarras A, et al, Rheumatology (Oxford) 56:1662-1675 (2017)., Lee-Kirsch M A et al, Annu Rev Med 68:297-315 (2017)). Blocking antibodies to either IFN-I-(Khamashta Met et al. Ann Rheum Dis.; 75 (11): 1909-1916 (2016)) or IFNAR1 (Furie Ret et al, Arthritis Rheumatol 69:376-386 (2017).) demonstrated effective in the treatment patients with active moderate to severe SLE.

In certain embodiments, the type I IFN-related disease or condition include, but are not limited to, HIV infection or Acquired Immunodeficiency Syndrome (AIDS, which is a viral disease with an autoimmune component), inflammatory bowel disease (IBD), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenia purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, psoriasis, autoimmune thyroiditis, autoimmune primary hypothyroidism, Graves' disease, Guillain-Barre syndrome, Hashimoto's thyroiditis, destructive thyroiditis with hypothyroidism, idiopathic pulmonary fibrosis, idiopathic thrombocytopenia purpura (ITP), idiopathic inflammatory myopathies (IIM), IgA nephropathy, IgM polyneuropathies, insulin-dependent diabetes mellitus (IDDM), juvenile chronic arthritis (Still's disease), Meniere's disease, mixed connective tissue disease, multiple sclerosis (MS), myasthenia gravis, Reynaud's syndrome, pustulosis palmoplantaris (PPP), erosive lichen planus, pemphigus bullosa, epidermolysis bullosa, contact dermatitis and atopic dermatitis, polyradiculitis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriatic arthritis, Raynaud's phenomena, Reiter's syndrome, rheumatic fever, rheumatoid arthritis (RA), juvenile rheumatoid arthritis, sarcoidosis, scleroderma (progressive systemic sclerosis (PSS), also known as systemic sclerosis (SS)), stiff-man syndrome, systemic lupus erythematosus (SLE), myositis, Sjögren's syndrome, Takayasu arteritis, temporal arteritis/giant cell arteritis, ulcerative colitis, Celiac's Disease, Chronic obstructive pulmonary disease (COPD), uveitis, vitiligo and Wegener's granulomatosis.

In certain embodiments, the IFNβ-mediated IFNAR1 activation is not inhibited in the methods of treatment provided herein. "Not inhibited" as used herein, means less than 20% inhibition on the level of IFNB-mediated IFNAR1 activation. In certain embodiments, the method of treatment further comprises administering a therapeutically effective amount of IFNβ. IFNβ administration is believed to further restore at least part of the IFNβ-mediated IFNAR1 activation.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g. physician or veterinarian) as indicated by these and other circumstances or requirements.

In certain embodiments, the antibody or antigen-binding fragment as provided herein may be administered at a therapeutically effective dosage of about 0.01 mg/kg to about 100 mg/kg. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g. a therapeutic response). For example, a single dose may be administered, or several divided doses may be administered over time.

The antibodies and antigen-binding fragments disclosed herein may be administered by any route known in the art, such as for example parenteral (e.g. subcutaneous, intraperitoneal, intravenous, including intravenous infusion, intramuscular, or intradermal injection) or non-parenteral (e.g. oral, intranasal, intraocular, sublingual, rectal, or topical) routes.

In some embodiments, the antibodies or antigen-binding fragments thereof disclosed herein may be administered alone or in combination with one or more additional therapeutic means or agents. For example, the antibodies or antigen-binding fragments thereof disclosed herein may be administered in combination with another therapeutic agent, for example, IFN-β, anti-IFNα antibody, anti-IFN-β antibody, anti-TNF antibody, anti-TNF receptor antibody, or soluble TNF receptor.

In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments thereof disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of inhibiting bioactivity of a cell expressing or overexpressing IFNα and/or IFNω, comprising contacting the cell with the antibody or antigen-binding fragment thereof provided herein.

In some embodiments, the present disclosure provides methods of detecting presence or level of IFNAR1 in a sample, comprising contacting the sample with the antibody or antigen-binding fragment thereof of provided herein.

In some embodiments, the present disclosure provides detecting or therapeutic kits comprising the antibody or antigen-binding fragment thereof provided herein and instructions for use, optionally conjugated with a detectable moiety. The kits may be useful in detection of IFNAR1 or therapeutic use for type I IFN-related disease or condition.

In some embodiments, the present disclosure also provides use of the antibody or antigen-binding fragment thereof provided herein in the manufacture of a medicament for treating a type I IFN-related disease or condition in a subject, in the manufacture of a diagnostic reagent for diagnosing a type I IFN-related disease or condition.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Materials

Lipofectamine 2000 was purchased from Invitrogen Inc. Isotype Control was purchased from Biolegend Inc. The HEK293T cell line was a product purchased from ATCC. Human IFNα2b was a product purchased from Cedarlane Inc. Twelve different IFNα subtypes were purchased from PBL Assay Science. Human IFNω was a product purchased from R&D Inc. Human IFNβ was purchased from PeproTech.

PBS solution was prepared as follows: 0.27 g of $KH_2PO_4$, 1.42 g of $Na_2HPO_4$, 8 g of NaCl, and 0.2 g of KCl were dissolved in an appropriate amount of water, the pH was adjusted to 7.2-7.4. The final volume was made up to 1 L with water.

The FACS buffer was a PBS solution containing 2% (v/v) Fetal Bovine Serum and 2 mM EDTA.

The IFNAR1 monoclonal antibody 10C2 and 10C9 was prepared following disclosures in PCT publication WO2018/010140.

The method of making the IFNAR1 monoclonal antibody was referred to the Current Protocol in Immunology, 1995 by John Wiley & Sons, Inc.

Example 1: Generation of IFNAR1 Monoclonal Antibodies 7G4 and 10C5

Antibodies 7G4 and 10C5 were generated using conventional hybridoma approach. In general, mice were immunized with human IFNAR1 antigen, and spleen cells were taken and fused with immortal cell line to generate hybridoma cell lines. Antibodies secreted from the hybridoma cells were screened for binding affinities with human IFNAR1, and the hybridoma cell lines expressing 7G4 and 10C5 antibodies were identified.

Hybridoma cell lines 7G4 and 10C5 were lysed using Trizol (Invitrogen) to extract the RNA of the hybridoma cell lines, following the manufacturer's instructions. The obtained RNA solution was reversed transcribed to cDNA using Oligo dT (Invitrogen). Using the obtained cDNA as a template, PCR amplification was carried out using a heavy chain primer pair (including heavy chain primer F and heavy chain primer R) and a light chain primer pair (including light chain primer F and light chain primer R), see below Table 5.

TABLE 5

| Primer name | Sequence |
|---|---|
| heavy chain primer F | 5'- SAR GTN MAG CTG SAG SAG TC -3' (SEQ ID NO: 29) |
| heavy chain primer R | 5'-CTTGACCAGGCATCCTAGAGTCA-3' (SEQ ID NO: 30) |
| light chain primer F | 5'-GAYATTGTGMTSACMCARWCTMCA-3' (SEQ ID NO: 31) |
| light chain primer R | 5'-GGATACAGTTGGTGCAGCATC-3' (SEQ ID NO: 32) |

Note: the above two forward primers are degenerate primers. S is c or g; R is a or g; N is a, c, g or t; M is a or c; Y is c or t; W is a or t.

The fragments encoding the heavy chain and the fragments encoding the light chain are sequentially obtained and sequenced.

The nucleotide sequences and amino acid sequences of the heavy chain variable region of antibody 7G4 are shown in FIG. 6, where sequences of CDR1 (the amino acid residues 31-35), CDR2 (the amino acid residues 50-66), and CDR3 (the amino acid residues 99-112) are marked accordingly.

The nucleotide sequence and amino acid sequence of the light chain variable region of antibody 7G4 are shown in FIG. 7, where sequences of CDR1 (the amino acid residues 24-34), CDR2 (the amino acid residues 50-56 residues), and CDR3 (the amino acid residues 89-97) are marked accordingly.

The nucleotide sequence and amino acid sequence of the heavy chain variable region of antibody 10C5 are shown in FIG. 8, where sequences of CDR1 (the amino acid residues 31-35), CDR2 (the amino acid residues 50-66), and CDR3 (the amino acid residues 99-112) are marked accordingly.

The nucleotide sequence and amino acid sequence of the light chain variable region of antibody 10C5 are shown in FIG. 9, where sequences of CDR1 (the amino acid residues 24-34), CDR2 (the amino acid residues 50-56), and CDR3 (the amino acid residues 89-97) are marked accordingly.

4. Analysis of Antibody Sequences

The nucleic acid fragments of the antibodies 7G4 and 10C5 were analyzed using the igblast tool. The V domain is delineated using Kabat numbering system. The results were as follows.

The V gene, D gene and J gene encoding the heavy chain of both antibodies 7G4 and 10C5 correspond to mouse IGHV1-69 gene, IGHD2-4 gene and IGHJ4 gene, respectively. The alignment results among the amino acid sequence of the heavy chain variable region of antibody 7G4 (SEQ ID NO: 7), and antibody 10C5 (SEQ ID NO: 9), of mouse V region (SEQ ID NO: 15) are shown in FIG. 10. The V gene and J gene encoding the light chain of both antibodies 7G4 and 10C5 correspond to mouse IGKV13-84 gene and IGKJ4 gene, respectively. The alignment results among the amino acid sequence of the light chain variable region of antibody 7G4 (SEQ ID NO: 8), and of antibody 10C5 (SEQ ID NO: 10), of mouse V region (SEQ ID NO: 16) are shown in FIG. 11.

Example 2: 7G4 and 10C5 Bind to the Human IFN-I Receptor IFNAR1

Binding of 7G4 and 10C5 antibodies was tested using Flow cytometry (FACS), following the procedures briefly described below.

Expression vector for full-length human IFNAR1 was constructed. The human IFNAR1 full-length CDS sequence (NM_000629) was inserted into vector pIRES2-EGFP (purchased from Addgene) via restriction sites NheI and EcoRI, according to general procedures described in "Molecular Cloning", Molecular Cloning: A Laboratory Manual, Cold Spring Harbor Laboratory Press, U.S.; 4th edition, 2012. The construct plasmid PIRES2-EGFP-IFNAR1 was thus obtained.

The plasmid pIRES2-EGFP-IFNAR1 was transfected into HEK293T cells using Lipofectamine 2000. After 24 hours, the cells were diluted with 2 mM EDTA in PBS to make single cell suspension, which was subsequently added to a 96-well U-bottom plate at a density of 10,000 cells/200 μL/well. After centrifugation at 2200 rpm for 3 min, the supernatant was discarded and the cell pellet was collected and re-suspended.

The test antibody (7G4 or 10C5 or an isotype antibody) was diluted with FACS Buffer to a concentration of 10 μg/ml, and incubated with the re-suspended cell pellet at 4° C. for 30 min. After the incubation, the cells were centrifuged and re-suspended with 200 μL of FACS buffer, before next centrifugation and re-suspension.

PE-labeled goat anti-mouse IgG antibody (Biolegend) diluted in FACS buffer at 1:400 was added to each well. The cells were re-suspended and incubated at 4° C. for 30 min in the dark. After the incubation, the plate was centrifuged, the supernatant was discarded, and the cells were washed once as described above and re-suspended by adding 200 μL FACS buffer. Finally, the re-suspended cells were analyzed using a flow cytometer Guava (Millipore) for cellular GFP and PE signals.

The results are shown in FIGS. 1A and 1B. It was shown that both 7G4 and 10C5 antibodies specifically bound to the cells overexpressing human IFNAR1, as the GFP-positive cells in the plot were shifted to the right.

Example 3: Binding of 7G4 and 10C5 to Different Truncations of Human IFNAR1

Human IFNAR1 variants having different lengths and truncations were constructed and expressed on 293T cells. The variants include: IFNAR1-aal-557 (i.e. full length), IFNAR1-Δaa32-126 (i.e. absent of the subdomain spanning the amino acid residues 32 to 126), IFNAR1-Δaa127-227 (i.e. absent of the subdomain spanning the amino acid residues 127 to 227), IFNAR1-Δaa231-329 (i.e. absent of the subdomain spanning the amino acid residues 231 to 329), IFNAR1-Δaa331-432 (i.e. absent of the subdomain spanning the amino acid residues 331 to 432), IFNAR1-Δaa32-126, Δaa331-432 (i.e. absent of both the subdomain spanning the amino acid residues 32 to 126 and the subdomain spanning the amino acid residues 331 to 432), IFNAR1-Δaa231-432 (i.e. absent of the subdomain spanning the amino acid residues 231 to 432), and IFNAR1-Δaa32-227 (i.e. absent of the subdomain spanning the amino acid residues 32 to 227).

Binding of 7G4 and 10C5 antibodies to 293T cells overexpressing the 8 human IFNAR1 variants respectively was detected by flow cytometry following the procedures of Example 1.

As shown in FIG. 2A and FIG. 2B, both antibodies 7G4 and 10C5 showed similar binding characteristics to the 8 tested human IFNAR1 variants. Specifically, they both bind to full length IFNAR1 (i.e. IFNAR1-aal-557), IFNAR1-Δaa32-126, IFNAR1-Δaa331-432, and IFNAR1-Δaa32-126, Δaa 331-432, and the binding activities to these 4 variants appeared similar. The results also indicated that both antibodies did not bind to the fragment spanning the amino acid residues 32-126, or the amino acid residues 331-432 of human IFNAR1, because absence of anyone or both fragment did not seem to affect the binding of the both antibodies to the human IFNAR1 truncated variants. Both antibodies bind well to IFNAR1-Δaa32-126, Δaa 331-432, indicating that the 127-330aa fragment of human IFNAR1 was sufficient for the binding of 7G4 and 10C5 to human IFNAR1.

However, the binding of both antibodies 7G4 and 10C5 to human IFNAR1 was abolished when any or both of the fragments spanning the amino acid residues 127-227 and the amino acid residues 231-239 is missing. This showed that both antibodies bind to both a first binding fragment within the amino acid residues 127-227 of human IFNAR1 and a second binding fragment within the amino acid residues 231-239.

This proves that the binding epitope of 7G4 and 10C5 are likely to be within the 127-329aa fragment of human IFNAR1.

Example 4: 7G4 and 10C5 Bind to Human IFNAR1 at a Different Epitope from That of 10C2 and 10C9

To further investigate the binding epitope of 7G4 and 10C5, and to compare with that of 10C2 and 10C9, human/mouse chimeric IFNAR1 variant (i.e. IFNAR1-m149-214) was constructed and expressed on 293T. IFNAR1-m149-214 has the amino acid sequence of SEQ ID NO: 69, i.e. the fragment spanning the amino acid residues 149-214 (SEQ ID NO:63) in the wild type human IFNAR1 was replaced with the mouse IFNAR1 homographic sequence (SEQ ID NO:64). Binding of 10C2, 10C9, 7G4 and 10C5 antibodies to 293T overexpressing the IFNAR1-WT and IFNAR1-m149-214 respectively was detected by flow cytometry following the procedures of Example 1. The antibodies were diluted into indicated concentration in FIG. 14A-14D.

As shown in FIG. 14A and FIG. 14B, 10C2 and 10C9 showed no or significantly diminished binding to IFNAR1-m149-214, although both 10C2 and 10C9 showed concentration-dependent binding to wild type IFNAR1. In contrast, both 7G4 and 10C5 showed comparable binding to wild type IFNAR1 and IFNAR1-m149-214 (FIG. 14C and FIG. 14D).

This clearly showed that 7G4 and 10C5 differed from 10C2 and 10C9 in the binding site on human IFNAR1. Specifically, the fragment spanning the amino acid residues 149-214 of human IFNAR1 was shown to be necessary for 10C2 and 10C9 to bind to human IFNAR1. But the results were different for 7G4 and 10C5, indicating that the binding of 7G4 and 10C5 to this fragment differs from that of 10C2 and 10C9.

Example 5: Effects of Antibodies 7G4 and 10C5 on Blocking the Biological Activity of Human IFN-I in Reporter Cell Lines IFN-I reporter cell line was constructed as described in PCT publication WO2018/010140. The reporter cells were added to a 96-well plate (30,000 cells/200 μL/well) and cultured for 24 h. The supernatant in the cell culture was removed and the cells were treated with respective test antibody (7G4 or 10C5) diluted in DMEM supplemented with 10% (v/v) FBS at an antibody concentration of 10 μg/mL. The cells were then incubated at 37° C. for 1 h, before treating with 1 ng/mL IFNα2b, or 50 μg/ml human IFNβ in 100 μL DMEM. Different human IFNα factors were also tested separately, i.e., IFNα2a, IFNα8, IFNα10, IFNα1, IFNα21, IFNα5, IFNα14, IFNα17, IFNα7, IFNα6, IFNα4, and IFNα16, except that each of them were tested at serial-dilutions at 0.03, 0.1, 0.3, 1, 3, 10, 30, 100, 300, 1000, 3000 Units/mL. IFNω was also tested separately, except that the concentration was 50 μg/ml. The treated cells were further cultured at 37° C., 5% $CO_2$ for 24 hours, before the cells were analyzed by flow cytometry to determine the blockade effect of the antibodies to the IFN-induced GFP-expression in the reporter cells.

The blockade effect can be calculated as: (GFP positive rate of control antibody-GFP positive rate of blocking antibody)/(GFP positive rate of control antibody-GFP positive rate of blank control)*100%

The experimental results are shown in Table 6 and FIG. 3.

TABLE 6

| IFN Type | 7G4 | 10C5 | 10C2 | 10C9 |
|---|---|---|---|---|
| IFNα2b | ++ | ++ | ++ | ++ |
| IFNα2a | ++ | ++ | ++ | ++ |
| IFNα8 | ++ | ++ | ++ | ++ |
| IFNα10 | ++ | ++ | ++ | ++ |
| IFNα1 | ++ | ++ | ++ | ++ |
| IFNα21 | ++ | ++ | ++ | ++ |
| IFNα5 | ++ | ++ | ++ | ++ |
| IFNα14 | ++ | ++ | ++ | ++ |
| IFNα17 | ++ | ++ | ++ | ++ |
| IFNα7 | ++ | ++ | ++ | ++ |
| IFNα6 | ++ | ++ | ++ | ++ |
| IFNα4 | ++ | ++ | ++ | ++ |
| IFNα16 | ++ | ++ | ++ | ++ |
| IFNω | ++ | ++ | ++ | ++ |
| IFNβ | +/− | +/− | + | + |

"++" represents a blocking effect greater than 80%,
"+" represents a blocking effect between 40% and 80%,
"+/−" represents a blocking effect less than 10%.

As shown in Table 6, both antibodies 7G4 and 10C5 blocked GFP-expression induced by all the 13 different IFNα factors and by IFNω, all at a blocking rate of greater than 80%. This was comparable to the results observed with control antibodies 10C2 and 10C9, which were known as anti-human IFNAR1 antibodies. However, in contrast to 10C2 and 10C9, both antibodies 7G4 and 10C5 showed less than 10% of blockade of GFP-expression induced by IFNβ, and this was much lower than that observed with 10C2 and 10C9, which were between 40%-80% blocking rate on GFP-expression induced by IFNβ.

Similar results are also shown in FIG. 3. The percentage of GFP positive cells reflected the activation signal of IFN-Is including IFNα, IFNω and IFNβ. Without adding any interferon (Mock control), the background percentage was about 5%. Addition of 1 ng/ml human IFNα2b, 50 μg/ml IFNω, and 50 μg/ml IFNβ all induced more than 5-fold increase in the percentage of GFP positive cells (i.e. to more than 30%, 40% or more than 50%), indicating activation of the human IFNAR1. The 12 other IFNα subtypes shown in FIG. 3B were added at a threshold concentration that provided for more than 5-fold activation relative to Mock control.

Both 7G4 and 10C5 significantly blocked the biological activity of human IFNα2b and IFNω, suppressing the signal to below 10% or even comparable to Mock control (FIG. 3A, 3C). Similar blocking effects were also observed on 12 different human IFNα subtypes (FIG. 3B).

Contrary to the blockade on IFNα and IFNω, both 7G4 and 10C5 showed minimum or non-detectable blocking effects on human IFNβ (FIG. 3D), and the signal in the presence of 7G4 and 10C5 were comparable to that of isotype control (e.g. more than 40%). This distinguished both antibodies 7G4 and 10C5 from the existing antibody 10C2, which still blocked human IFNβ mediated activation and showed a signal of around 20%, i.e. only half of the signal observed for 7G4 and 10C5. There was no significant difference observed between 7G4 and 10C5 in the effect of blocking human IFNB.

In conclusion, IFNAR1 monoclonal antibodies 7G4 and 10C5 can block all IFNα subtypes and IFNω, but did not block IFNβ.

Example 6: Effects of Antibodies 7G4 and 10C5 in Blocking Inhibition of Viral Replication by IFNα2b and IFNβ

In brief, the antibodies were tested in viral replication assay in the presence of IFNα2b or IFNβ or null (as Mock control). On Day1, test cells were prepared in 12 well plates with poly-L-lysine treatment. On Day2, the respective anti-IFNAR1 test antibody (i.e. Isotype, 10C2, 7G4, or 10C5) was added into the cells at 10 μg/ml and incubated for 1 h, before addition of IFNα or IFNβ and subsequently followed by incubation (e.g. for 1 h or 8 h). Next, the wells were washed and cells were infected with proper test virus at a suitable Multiplicity of Infection (MOI). 24 or 48 hours later, the luciferase activity were tested (Promega). The assay settings for different test viruses were listed in below Table 7.

TABLE 7

| Test virus and MOI | Test cells | IFNα | IFNβ | Viral replication assay |
|---|---|---|---|---|
| SINV-Luc; MOI: 0.01 | 293T cells | 200 pg/ml | 50 pg/ml | luciferase activity |
| Flu-Luc; MOI: 0.01 | A549 cells | 12.5 pg/ml | 12.5 pg/ml | luciferase activity |
| HSV; MOI: 0.1 | HeLa cells | 200 pg/ml | 50 pg/ml | plaque assay |

Figure 4:
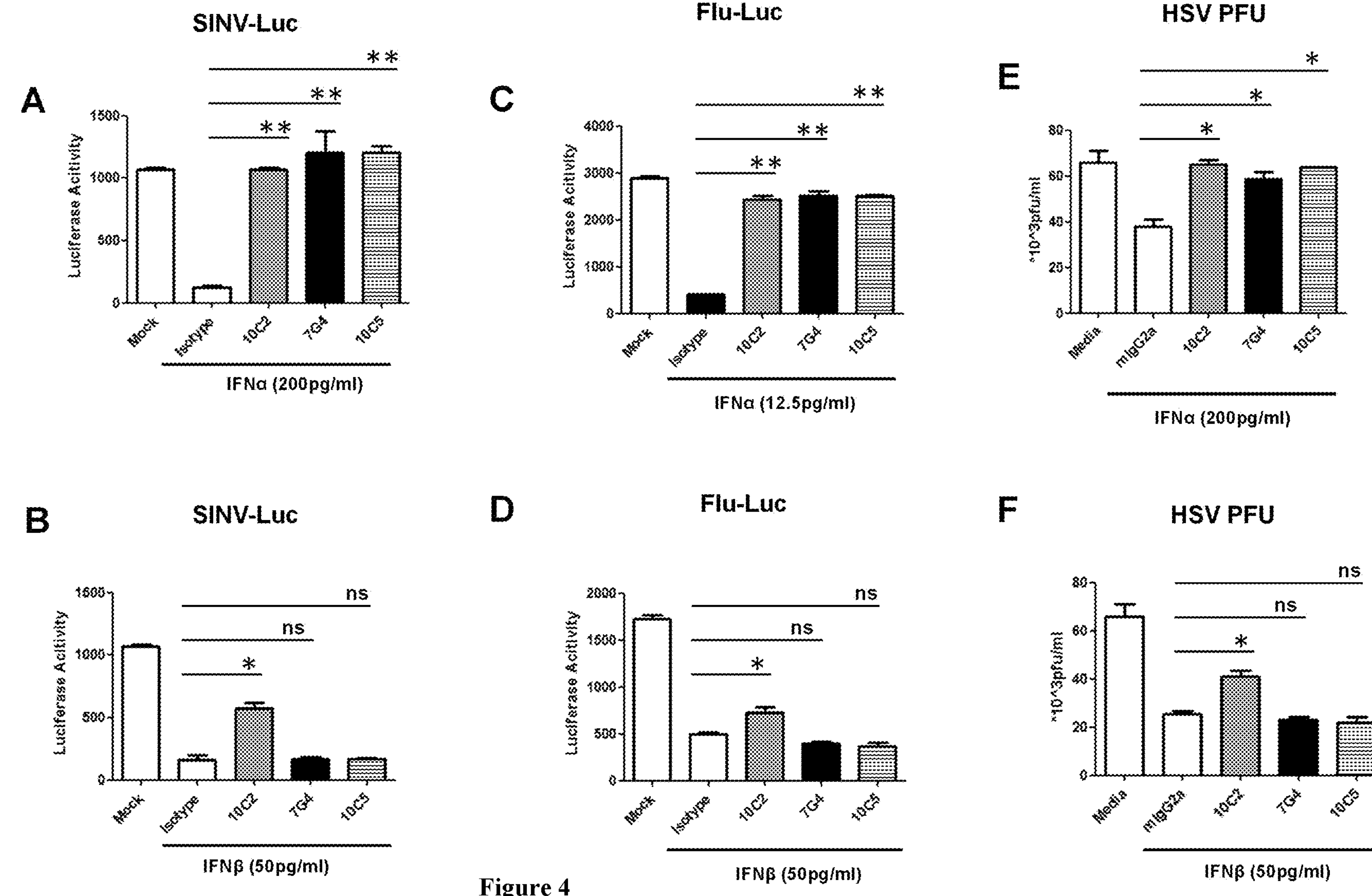
FIG. 4 shows that antibodies 7G4 and 10C5 blocked IFNα-mediated viral replication inhibition but did not affect the IFNβ-mediated viral replication inhibition.

As shown in FIGS. 4A, 4C, and 4E, when IFNα was present, the viral replication level was significantly inhibited (see, results for the Isotype), and presence of both antibodies 7G4 and 10C5 restored the viral replication to a level comparable to that of Mock control (i.e. absent of IFNα). Such results were also shown with 10C2, and were attributable to the inhibition of IFNα-mediated IFNAR1 activation.

IFNβ also significantly inhibited viral replication level, as shown in FIGS. 4B, 4D, and 4F, in the results for the Isotype. However, contrary to the results with IFNα, presence of both antibodies 7G4 and 10C5 did not change the viral replication level, and it remained as low as what was observed with an Isotype control. In contrast, antibody 10C2 showed restoration of viral replication to a level significantly above that of the Isotype control. This further demonstrated that both antibodies 7G4 and 10C5 did not block the IFNβ-mediated viral replication inhibition, and this distinguished both antibodies from existing antibody such as 10C2.

Example 7: Effects of Antibodies 7G4 and 10C5 in Blocking IFN-I in the Serum from SLE Patients The assay were performed following the same procedures according to Example 5, except that the 1 ng/ml human IFNα2b was replaced with the serum from SLE patients. Other steps remained unchanged. That is, IFN-I reporter cell line was treated with the respective antibody followed by incubation with the serum from SLE patients, and rate of GFP positive cells were determined.

Figure 5:
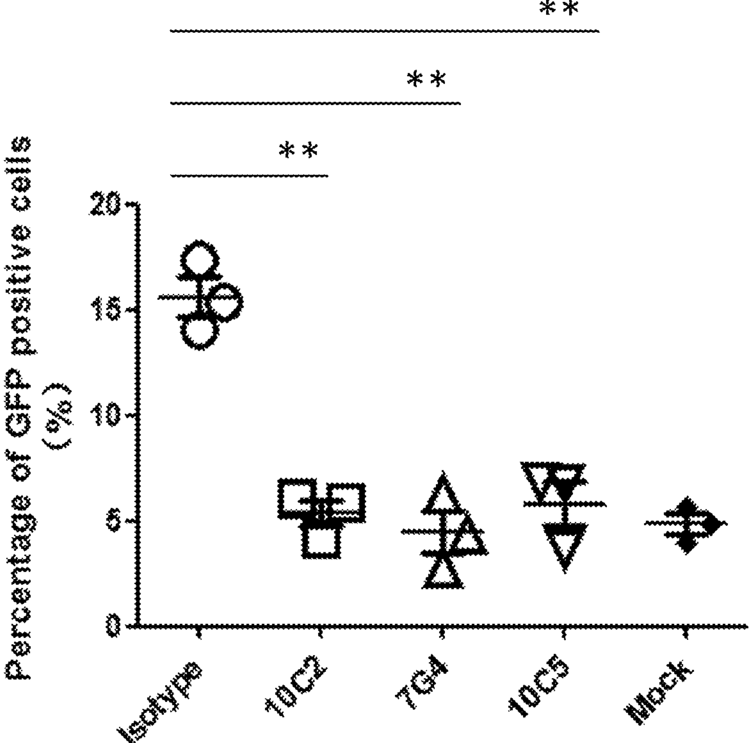
FIG. 5 shows that IFNAR1 monoclonal antibodies 7G4 and 10C5 blocked human IFNAR1 activation mediated by IFN-I in the serum of SLE patients. "*" represents $p<0.05$, "**" represents $p<0.01$, and "ns" represents no significant difference.

The results are shown in FIG. 5. The isotype antibody showed a percentage of GFP positive cells of around 15%, indicating that the IFNAR1 was activated by the IFN-I in the serum from the SLE patients. In comparison, all the three tested antibodies, 10C2, 7G4, and 10C5 inhibited the percentage by almost 3-fold, to a level comparable to that of the Mock control, i.e. in the absence of the SLE patient serum. This indicated that antibodies 7G4 and 10C5 were comparably effective in inhibiting IFNAR1 activation mediated by IFN-I in the SLE patient serum.

Example 8: Antibody Humanization

1. Sequence Analysis of Parental Antibody

The VH/VL CDR residues were annotated with Kabat numbering system (see FIGS. 6-9). Sequence analysis revealed no major risky hot spots including unpaired cysteine residues, N-glycosylation site, and deamination site within the CDRs.

2. Selection of Human Germline Acceptor Family Subsets

Based on the sequence homology between mouse antibody and human germline framework regions, the best human germline framework acceptors, IGHV1-46*01 and IGKV1D-39*01, were selected for CDR grafting. The encoded amino acid sequences of IGHV1-46*01 and IGKV1D-39*01 are provided in SEQ ID NOs: 59 and 60. The human J-region was selected based on best sequence homology.

3. Back-Mutation Design

According to 3D structure of the homology model, residues within 5 Å distance of CDRs were selected as potential back mutation sites because the exposed residues might be involved in antigen binding directly and the buried residues might be important for maintaining the CDR conformation. The VH/VL interface were analyzed and back mutations were introduced where issues such as steric clash were identified. The importance of individual back-mutations was determined by in silico analysis and a panel of engineered antibodies containing different combinations of single back-mutations were designed.

4. Generation of Engineered Antibodies

The recombinant DNA constructs were gene synthesized and subcloned into selected human Ig backbone for antibody expression. 4 different humanized VH and 4 different humanized VL were obtained respectively. A total of 16 engineered LC/HC constructs were co-expressed in high throughput format, which resulted in a panel of antibodies transiently expressed from HEK293 cell line. These antibodies were then purified using protein A columns and formulated in 1×PBS pH7.4. About 1 mg each protein was produced for binding, functional and biophysical characterizations.

The 16 clones of humanized 7G4 are listed in Table 8.

TABLE 8

| | 7G4-g0-VH | SEQ ID NO (VH/VL) | 7G4-g1-VH | SEQ ID NO (VH/VL) | 7G4-g2-VH | SEQ ID NO (VH/VL) | 7G4-g3-VH | SEQ ID NO (VH/VL) |
|---|---|---|---|---|---|---|---|---|
| 7G4-g0-VL | Hu4-1 | 51/55 | Hu4-2 | 52/55 | Hu4-3 | 53/55 | Hu4-4 | 54/55 |
| 7G4-g1-VL | Hu4-5 | 51/56 | Hu4-6 | 52/56 | Hu4-7 | 53/56 | Hu4-8 | 54/56 |
| 7G4-g2-VL | Hu4-9 | 51/57 | Hu4-10 | 52/57 | Hu4-11 | 53/57 | Hu4-12 | 54/57 |
| 7G4-g3-VL | Hu4-13 | 51/58 | Hu4-14 | 52/58 | Hu4-15 | 53/58 | Hu4-16 | 54/58 |

Example 9: Characterization of Humanized 7G4 Antibodies

1. The Humanized Antibodies were Tested for the Binding Affinity Using ELISA 96-well plates were coated with 100 ul 5 ug/ml human IFNAR1 ECD in 1×PBS and incubate at 4° C. overnight. The plates were then washed with PBST (1×PBS+0.05% Tween20) for 3 times and blocked with the blocking buffer (1×PBS+0.05% Tween20+1% BSA) at RT for 2 hr. After washing the plates with PBST for 3 times, the purified humanized 7G4 antibodies (Hu7G4) were added at 100 ul/well and incubated at RT for 1 hr. The plates were washed with PBST for 3 times, followed by addition of antibody (Anti-Human IgG (Fc specific)-Peroxidase antibody produced in goat, ZSGB-BIO) at 100 ul/well and then incubated at RT for 1 hr. The plates were washed with PBST 5 times and then 100 ul/well TMB was added and after 15 minutes, the plates were quenched with 50 ul/well 2N $H_2SO_4$. The plates were read with Molecular device spectra max at 450 nm.

Figure 12:
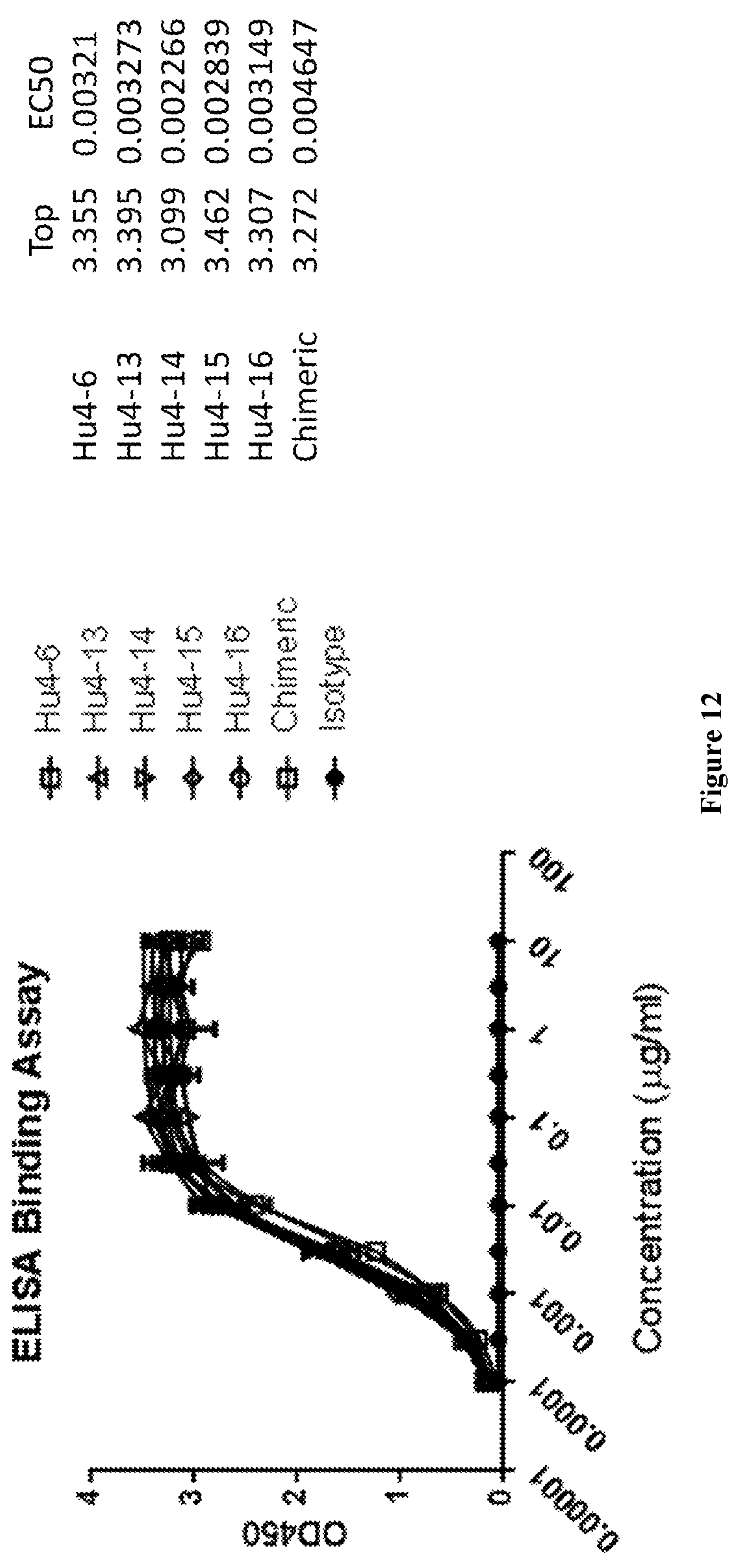
FIG. 12 shows the results of ELISA binding assay results of humanized 7G4 variants (i.e. Hu4-6, Hu4-13 to Hu4-16).
Figure 14:
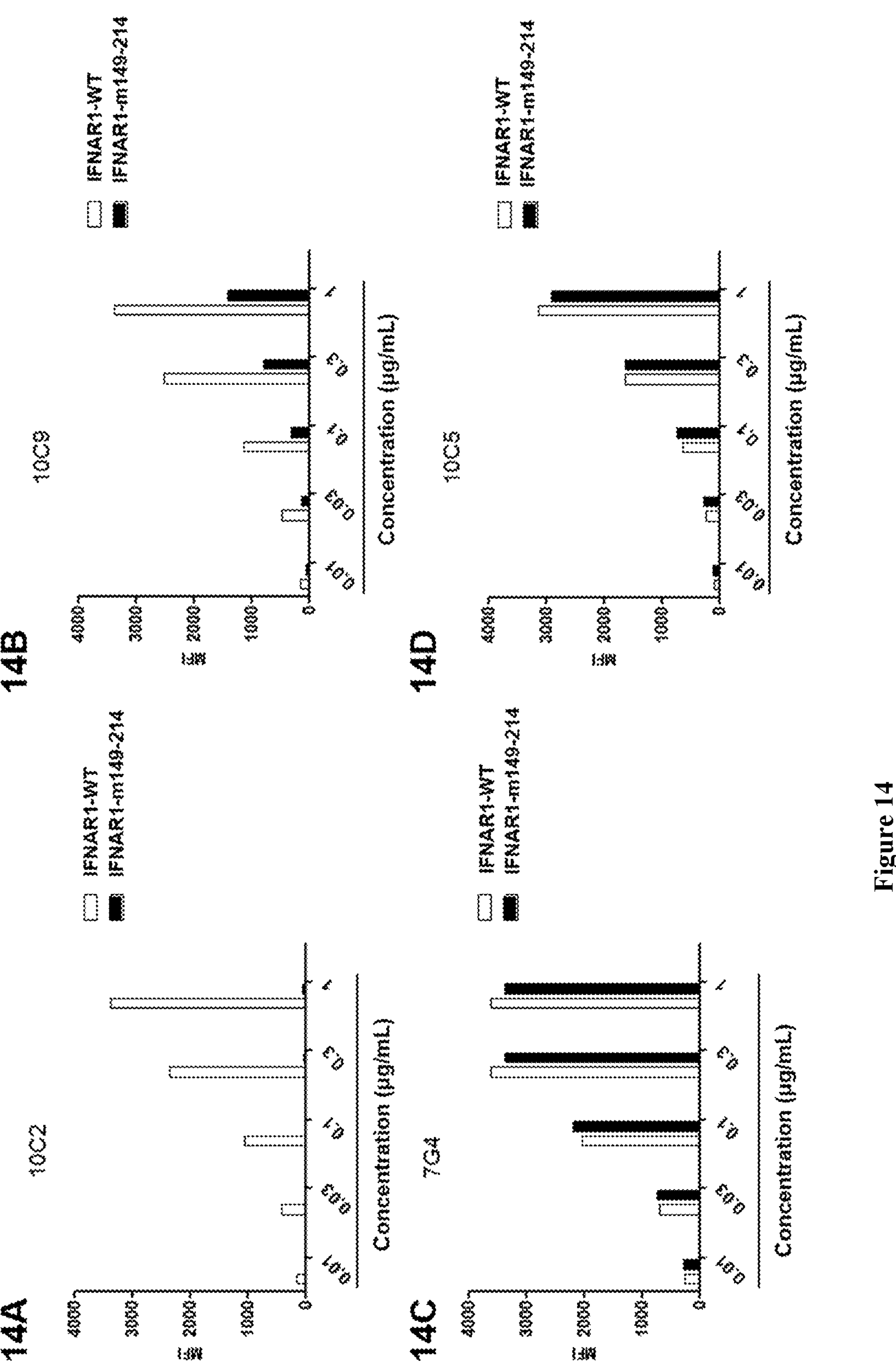
FIGS. 14A-14D show that antibodies 7G4 and 10C5 bind to human IFNAR1 at a site different from that bound by existing antibodies 10C2 and 10C9, as measured by flow cytometry. IFNAR1-WT: wild type human IFNAR1; IFNAR1-m149-214: human IFNAR1 in which amino acid residues 149-214 were replaced by mouse IFNAR1 homographic sequence. Amino acid residues 149-214 of human IFNAR1 are required for binding of antibodies 10C2 and 10C9 (FIGS. 14A and 14B), but are shown to play a different role in the binding of antibodies 7G4 and 10C5, and thus distinguish antibodies 7G4 and 10C5 from antibodies 10C2 and 10C9.

The results were shown in FIG. 12. All the rested variants showed comparable binding activity to IFNAR1, with an $EC_{50}$ of around 0.002-0.004 μg/ml.

2. Binding of Hu7G4 Variants to Human IFNAR1 were Tested Using Biacore.

Materials and Reagent:

| Material and Reagents | Company | Catalogue Number |
|---|---|---|
| 1. Series S Sensor Chip CM5 | GE Healthcare | BR-1000-30 |
| 2. Human Antibody Capture Kit | GE Healthcare | BR-1008-39 |
| 3. HBS buffer BIA Certified | GE Healthcare | BR-1001-88 |
| 4. Regeneration buffer Glycine 1.5 | GE Healthcare | BR-1003-54 |
| 5. BIAmaintenance Kit | GE Healthcare | BR-1006-66 |

Preparation of a CM5 chip surface: Using HBS-EP+ (10 mM HEPES, 150 mM NaCl, 3 mM EDTA, 0.05% surfactant P20) as running buffer, both channel 1&2 of a CM5 sensor chip (GE Healthcare, BR-1000-30) were activated with a fresh mixture of 50 mM NHS and 200 mM EDC (1:1). Anti-human IgG Fc, 20 μg/ml in 10 mM NaOAc buffer (pH 5.0), was then passed over the activated surface of the two flow cells in each channel at 10 ul/min (target around 10000 RU). The remaining active coupling sites were blocked with 10-min injection of 1 M ethanolamine. Low flow rate was maintained over 2 hours for the equilibrium of the immobilized protein.

2. Measurement of binding kinetics: Each antibody was captured in flow cell FC2 in channel 1&2 around 250 RU respectively, using FC1 as the reference cell, followed by injection of antigen samples at varying concentrations. The signals with captured antibody subtracted from that without captured antibody were calculated with Biacore 8K evaluation software. The running buffer was HBS-EP+ (10 mM HEPES, 150 mM NaCl, 3 mM EDTA, 0.05% surfactant P20).

The results for the antibody-antigen interaction were shown in Table 9 below.

TABLE 9

| Antigen | Antibody | ka (1/Ms) | kd (1/s) | $K_D$ (M) |
|---|---|---|---|---|
| Human IFNAR1 SD1-SD4 | Hu4-6 | 4.44e+05 | 2.81e−04 | 6.33e−10 |
| | Hu4-13 | 4.49e+05 | 3.01e−04 | 6.71e−10 |
| | Hu4-14 | 4.65e+05 | 2.14e−04 | 4.61e−10 |
| | Hu4-15 | 4.72e+05 | 2.09e−04 | 4.42e−10 |
| | Hu4-16 | 4.51e+05 | 2.10e−04 | 4.66e−10 |
| | 7G4 Chimeric | 4.56e+05 | 3.49e−04 | 7.65e−10 |

3. Blocking Activity of the Hu7G4 Variants

The effects of Hu7G4 variants on blocking the biological activity of human IFN-I in reporter cell lines were tested using methods similar to that in Example 5. The tested Hu7G4 variants (Hu4-5 to Hu4-16) maintain the blocking activity to IFNα (FIG. 13A) but do not inhibit IFNβ (see FIG. 13B).

Example 10: Humanized 7G4 Antibody Tolerated Amino Acid Residue Substitutions in CDR Sequences with Unchanged Binding Capacity to Human IFNAR1

1. Production of Humanized Monoclonal Antibodies Against Human IFNAR1

Humanized antibody Hu4-6 was selected as the basis for mutation. Three mutants were made: Mut-1 (A108G, in HCDR3), Mut-2 (T53S and S56T, in LCDR2), and Mut-3 (A108G in HCDR3, T53S and S56T in LCDR2). The sequences of the three mutants were shown in Table 10.

TABLE 10

| Hu4-6 mAb variants | Variable region combination |
|---|---|
| Hu4-6-Mut-1 | VL g1 (SEQ ID NO:56) + VH g1 with substitution A108G (SEQ ID NO:67, one substitution in CDR3) |
| Hu4-6-Mut-2 | VL g1 with substitutions T53S and S56T (SEQ ID NO:68, two substitutions in CDR2) + VH g1 (SEQ ID NO:52) |
| Hu4-6-Mut-3 | VL g1 with substitutions T53S and S56T (SEQ ID NO:68) + VH g1 with substitution A108G (SEQ ID NO:67) |

The full-length coding region of heavy chain and light chain were cloned into selected human Ig backbone for antibody expression. HEK 293T cells in a 100 mm-dish were co-transfected with plasmid containing the heavy chain gene and plasmid containing the light chain gene as a ratio 1:1 by Lipofectamine 2000 (Thermo Fisher Scientific). The culture supernatants were harvested at 24 h, 48 h and 72 h after transfection. The monoclonal antibody (mAb) was purified from culture supernatants using Protein A affinity resin (REPLIGEN).

2. The Binding Capacity of the Mutant Antibodies to Human IFNAR1

Figure 15:
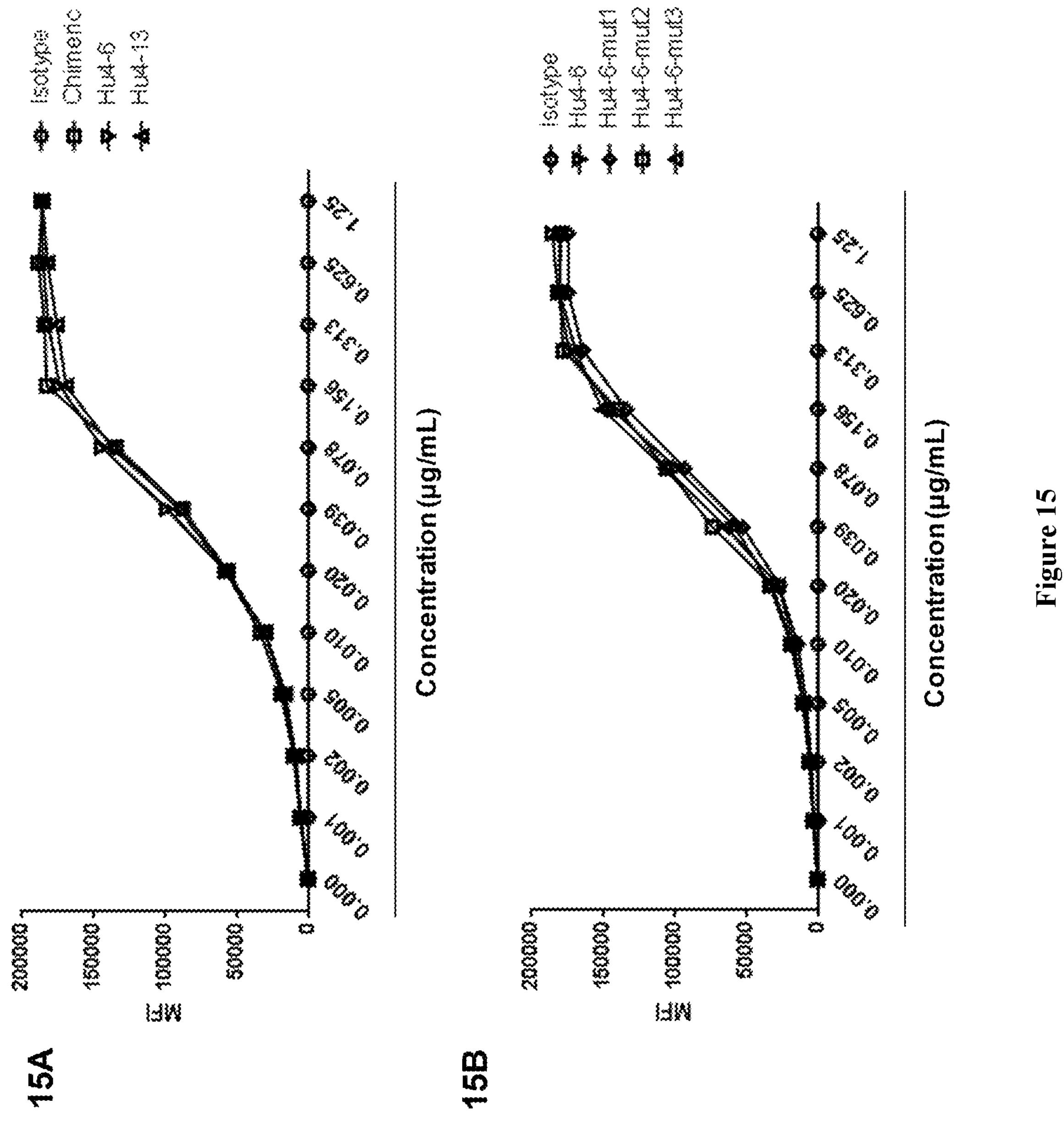
FIG. 15A-15B show that humanized 7G4 antibody having one, two or three mutations still exhibited similar binding property to human IFNAR1.

To test the binding of anti-human IFNAR1 antibodies to human IFNAR1, the anti-human IFNAR1 antibodies and isotype control mAb were diluted in FACS buffer at the indicated concentration in FIG. 15A-15B. The flow cytometry following the procedure of Example 1.

The median fluorescence intensity (MFI) of PE for each sample was used to determine the binding capacity of the antibodies to human IFNAR1.

As shown in FIG. 15B, all substitution of one or more amino acid residues in the CDR regions did not impact the binding efficiency of the antibody disclosed herein to human IFNAR1.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An antibody or antigen-binding fragment thereof comprising heavy chain HCDR1, HCDR2 and HCDR3, and light chain LCDR1, LCDR2 and LCDR3, wherein the HCDR1 comprises the sequence of $SX_1WX_{19}N$ (SEQ ID NO:1), the HCDR2 comprises the sequence of $KIDPSDSEX_2X_{20}X_{21}NQKFX_{22}D$ (SEQ ID NO:2), the HCDR3 comprises the sequence of $GGX_3IX_4X_5DYDX_6AX$-DY (SEQ ID NO:3), the LCDR1 comprises the sequence of $KX_{23}SEVIYNRLA$ (SEQ ID NO:4), the LCDR2 comprises the sequence of GATX$_{24}$LEX$_{25}$ (SEQ ID NO:5), and the LCDR3 comprises the sequence of QQYWX$_8$X$_9$PFT (SEQ ID NO:6), wherein $X_1$ is Y or F, $X_2$ is T or I, $X_3$ is R or G, $X_4$ is S or Y, $X_5$ is F or Y, $X_6$ is A or G, $X_7$ is L or M, $X_8$ is N or S, $X_9$ is K or S, $X_{19}$ is M or L, $X_{20}$ is H or R, $X_{21}$ is F or Y, $X_{22}$ is R or K, $X_{23}$ is S or A, $X_{24}$ is T or S, $X_{25}$ is S or T, and wherein the antibody or antigen-binding fragment thereof is capable of specifically binding to human interferon alpha receptor 1 (human IFNAR1), and wherein the antibody or antigen-binding fragment thereof binds to a first fragment of amino acid residues 127-227 of human IFNAR1 and a second fragment of amino acid residues 231-329 of human IFNAR1; and is capable of specifically binding to a truncated human IFNAR1 absent of: a) amino acid residues 32-126, and b) amino acid residues 331-432;

and wherein the antibody or antigen-binding fragment thereof inhibits IFNα- and IFNω-mediated human IFNAR1 activation; and does not inhibit IFNβ-mediated human IFNAR1 activation, wherein the IFNα encompasses all subtypes of IFNα;

and wherein sequence of the human IFNAR1 is human IFNAR1 protein (NCBI Ref Seq No. NP_000620.2).

2. The antibody or antigen-binding fragment thereof of claim 1, wherein:

the HCDR1 comprises a sequence selected from SEQ ID NOs: 21 and 25, the HCDR2 comprises a sequence selected from SEQ ID NOs: 22 and 26, the HCDR3 comprises a sequence selected from SEQ ID NOs: 23, 27 and 65, the LCDR1 comprises a sequence selected from SEQ ID NOs: 70 and 72, the LCDR2 comprises a sequence selected from SEQ ID NOs: 71 and 66, and the LCDR3 comprises a sequence selected from SEQ ID NOs: 24 and 28.

3. The antibody or antigen-binding fragment thereof of claim 1, which comprises:

a) the HCDR1 comprising the sequence of SEQ ID NO:21, the HCDR2 comprising the sequence of SEQ ID NO:22, the HCDR3 comprising the sequence of SEQ ID NO: 23, the LCDR1 comprising the sequence of SEQ ID NO:70, the LCDR2 comprising the sequence of SEQ ID NO:71, and the LCDR3 comprising the sequence of SEQ ID NO:24;

b) the HCDR1 comprising the sequence of SEQ ID NO:25, the HCDR2 comprising the sequence of SEQ ID NO:26, the HCDR3 comprising the sequence of SEQ ID NO: 27, the LCDR1 comprising the sequence of SEQ ID NO:72, the LCDR2 comprising the sequence of SEQ ID NO:66, and the LCDR3 comprising the sequence of SEQ ID NO:28;

c) the HCDR1 comprising the sequence of SEQ ID NO:21, the HCDR2 comprising the sequence of SEQ ID NO:22, the HCDR3 comprising the sequence of SEQ ID NO: 65, the LCDR1 comprising the sequence of SEQ ID NO:70, the LCDR2 comprising the sequence of SEQ ID NO:71, and the LCDR3 comprising the sequence of SEQ ID NO:24;

d) the HCDR1 comprising the sequence of SEQ ID NO:21, the HCDR2 comprising the sequence of SEQ ID NO:22, the HCDR3 comprising the sequence of SEQ ID NO: 23, the LCDR1 comprising the sequence of SEQ ID NO:70, the LCDR2 comprising the sequence of SEQ ID NO:66, and the LCDR3 comprising the sequence of SEQ ID NO:24; or e) the HCDR1 comprising the sequence of SEQ ID NO:21, the HCDR2 comprising the sequence of SEQ ID NO:22, the HCDR3 comprising the sequence of SEQ ID NO: 65, the LCDR1 comprising the sequence of SEQ ID NO:70, the LCDR2 comprising the sequence of SEQ ID NO:66, and the LCDR3 comprising the sequence of SEQ ID NO:24.

4. The antibody or antigen-binding fragment thereof of claim 1, further comprising one or more of heavy chain HFR1, HFR2, HFR3 and HFR4, and/or one or more of light chain LFR1, LFR2, LFR3 and LFR4, wherein:

a) the HFR1 comprises QVQLVQSGAEVKKPGASVKVSCKASGYTFT (SEQ ID NO: 33) or a homologous sequence of at least 80% sequence identity thereto, b) the HFR2 comprises WVRQX$_{10}$PGQGLEWX$_{11}$G (SEQ ID NO: 34) or a homologous sequence of at least 80% sequence identity thereto, c) the HFR3 sequence comprises RVTX$_{12}$TX$_{13}$DX$_{14}$STSTVYMELSSLRSEDTAVYYCAR (SEQ ID NO: 35) or a homologous sequence of at least 80% sequence identity thereto, d) the HFR4 comprises WGQGTLVTVSS (SEQ ID NO: 36) or a homologous sequence of at least 80% sequence identity thereto, e) the LFR1 comprises DIQMTQSPSSLSASVGDRVTITC (SEQ ID NO: 37) or a homologous sequence of at least 80% sequence identity thereto, f) the LFR2 comprises WYQQKPGX$_{15}$APKLLIX$_{16}$ (SEQ ID NO: 38) or a homologous sequence of at least 80% sequence identity thereto, g) the LFR3 comprises GVPSRFSGSGSGX$_{17}$DX$_{18}$TLTISSLQPEDFATYYC (SEQ ID NO: 39) or a homologous sequence of at least 80% sequence identity thereto, and h) the LFR4 comprises FGQGTKLEIK (SEQ ID NO: 40) or a homologous sequence of at least 80% sequence identity thereto, wherein $X_{10}$ is A or R, $X_{11}$ is M or I, $X_{12}$ is M or L, $X_{13}$ is R or V, $X_{14}$ is T or K, $X_{15}$ is K or N, $X_{16}$ is Y or S, $X_{17}$ is T or K, $X_{18}$ is F or Y.

5. The antibody or antigen-binding fragment thereof of claim 4, wherein:

the HFR1 comprises a sequence of SEQ ID NO: 33, the HFR2 comprises the sequence selected from SEQ ID NOs: 41, 42 and 43, the HFR3 comprises the sequence selected from SEQ ID NOs: 44, and 45, the HFR4 comprises a sequence of SEQ ID NO: 36, the LFR1 comprises the sequence of SEQ ID NO: 37, the LFR2 comprises the sequence selected from SEQ ID NOs: 46, 47 and 48, the LFR3 comprises a sequence selected from SEQ ID NOs: 49 and 50, and the LFR4 comprises a sequence of SEQ ID NO: 40.

6. The antibody or antigen-binding fragment thereof of claim 1, comprising a heavy chain variable region ($V_H$) comprising the sequence of SEQ ID NOs: 7, 9, 67, or 51-54 or a homologous sequence thereto having at least 80% sequence identity to SEQ ID NOs: 7, 9, 67, or 51-54.

7. The antibody or antigen-binding fragment thereof of claim 1, comprising a light chain variable region ($V_L$) comprising the sequence of SEQ ID NOs: 8, 10, 68, or 55-58 or a homologous sequence thereto having at least 80% sequence identity to SEQ ID NOs: 8, 10, 68, or 55-58.

8. The antibody or antigen-binding fragment thereof of claim 1, further comprising an immunoglobulin constant region, optionally wherein the constant region is a human immunoglobulin constant region, or a human IgG constant region.

9. The antibody or antigen-binding fragment thereof of claim 1, which is a humanized monoclonal antibody.

10. The antibody or antigen-binding fragment thereof of claim 1, which does not inhibit IFNβ-mediated anti-viral activity.

11. The antibody or antigen-binding fragment thereof of claim 10, whose inhibition effect on IFNα- or on IFNω-mediated human IFNAR1 activation is at least four, five, six or seven times higher than that on IFNβ-mediated human IFNAR1 activation.

12. The antibody or antigen-binding fragment thereof of claim 1, which is linked to one or more conjugate moieties.

13. The anti-human IFNAR1 antibody or antigen-binding fragment thereof of claim 1, which specifically binds to a human/mouse chimeric IFNAR1 comprising SEQ ID NO: 69 at a binding capacity comparable to the binding capacity of the antibody or antigen-binding fragment thereof to a full-length human IFNAR1.

14. The antibody or antigen-binding fragment thereof of claim 1, which does not bind to a truncated human IFNAR1 absent of either a) amino acid residues 127-227 or b) amino acid residues 231-329.

15. The antibody or antigen-binding fragment thereof of claim 1, which binds to the truncated human IFNAR1 at a binding capacity comparable to the binding capacity of the antibody or antigen-binding fragment thereof to a full-length human IFNAR1.

16. The antibody or antigen-binding fragment thereof of claim 1, which comprises a heavy chain variable region that is a product of or derived from one or more mouse germline immunoglobulin genes selected from: IGHV1-69 gene, IGHD2-4 gene, and IGHJ4 gene, and/or a light chain variable region that is a product of or derived from one or more mouse germline immunoglobulin genes selected from IGKV13-84 gene and IGKJ4 gene.

17. The antibody or antigen-binding fragment thereof of claim 16, which is humanized.

18. The antibody or antigen-binding fragment thereof of claim 1, wherein the antibody is produced by a hybridoma cell having a deposit number of CGMCC deposit No. 16286 or CGMCC deposit No. 16287.

19. The antibody or antigen-binding fragment thereof of claim 1, which is bispecific.

20. A pharmaceutical composition comprising the antibody or antigen-binding fragment thereof of claim 1, and a pharmaceutically acceptable carrier.

21. A detecting or therapeutic kit comprising the antibody or antigen-binding fragment thereof of claim 1 and instructions for use.

22. A therapeutic kit comprising the antibody or antigen-binding fragment thereof of claim 1 and IFNβ.

23. An isolated polynucleotide encoding the antibody or antigen-binding fragment thereof of claim 1.

24. An expression vector comprising the isolated polynucleotide of claim 23.

25. A host cell comprising the expression vector of claim 24.

26. A method of producing an antibody or antigen-binding fragment thereof, comprising culturing the host cell of claim 25 under the condition at which the vector is expressed.

27. The method of claim 26, further comprising purifying the antibody or antigen-binding fragment thereof produced by the host cell.

28. A hybridoma cell having a deposit number of CGMCC deposit No. 16286 or CGMCC deposit No. 16287.

* * * * *

SEQUENCE LISTING

```
<160> NUMBER OF SEQ ID NOS: 72

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Tyr or Phe
<220> FEATURE:
<221> NAME/KEY: misc_feature
<222> LOCATION: (4)..(4)
<223> OTHER INFORMATION: Xaa can be Met or Leu

<400> SEQUENCE: 1

Ser Xaa Trp Xaa Asn
1               5


<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(11)
<223> OTHER INFORMATION: Xaa in location 9 can be Thr or Ile, Xaa in
      location 10 can be His or Arg, Xaa in location 11 can be Phe or
      Tyr
<220> FEATURE:
<221> NAME/KEY: misc_feature
<222> LOCATION: (16)..(16)
<223> OTHER INFORMATION: Xaa can be Arg or Lys

<400> SEQUENCE: 2

Lys Ile Asp Pro Ser Asp Ser Glu Xaa Xaa Xaa Asn Gln Lys Phe Xaa
1               5                   10                  15

Asp


<210> SEQ ID NO 3
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Arg or Gly
<220> FEATURE:
<221> NAME/KEY: misc_feature
<222> LOCATION: (5)..(6)
```

<223> OTHER INFORMATION: Xaa in location 5 can be Ser or Tyr, Xaa in location 6 can be Phe or Tyr
<220> FEATURE:
<221> NAME/KEY: misc_feature
<222> LOCATION: (10)..(10)
<223> OTHER INFORMATION: Xaa can be Ala or Gly
<220> FEATURE:
<221> NAME/KEY: misc_feature
<222> LOCATION: (12)..(12)
<223> OTHER INFORMATION: Xaa can be Leu or Met

<400> SEQUENCE: 3

Gly Gly Xaa Ile Xaa Xaa Asp Tyr Asp Xaa Ala Xaa Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Ser or Ala

<400> SEQUENCE: 4

Lys Xaa Ser Glu Val Ile Tyr Asn Arg Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be Thr or Ser
<220> FEATURE:
<221> NAME/KEY: misc_feature
<222> LOCATION: (7)..(7)
<223> OTHER INFORMATION: Xaa can be Ser or Thr

<400> SEQUENCE: 5

Gly Ala Thr Xaa Leu Glu Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa in location 5 can be Asn or Ser, Xaa in location 6 can be Lys or Ser

<400> SEQUENCE: 6

Gln Gln Tyr Trp Xaa Xaa Pro Phe Thr
1               5

<210> SEQ ID NO 7
<211> LENGTH: 123
<212> TYPE: PRT
<213> ORGANISM: Mus musculus

<400> SEQUENCE: 7

```
Gln Val Gln Leu Gln Gln Pro Gly Ala Glu Leu Val Lys Pro Gly Ala
1               5                   10                  15

Pro Val Lys Leu Ser Cys Lys Ala Ser Gly Tyr Thr Phe Thr Ser Tyr
            20                  25                  30

Trp Met Asn Trp Val Arg Gln Arg Pro Gly Arg Gly Leu Glu Trp Ile
        35                  40                  45

Gly Lys Ile Asp Pro Ser Asp Ser Glu Thr His Phe Asn Gln Lys Phe
    50                  55                  60

Arg Asp Lys Ala Thr Leu Thr Val Asp Lys Ser Ser Thr Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Ser Val Thr Val Ser Ser
        115                 120


<210> SEQ ID NO 8
<211> LENGTH: 107
<212> TYPE: PRT
<213> ORGANISM: Mus musculus

<400> SEQUENCE: 8

Asp Ile Leu Met Thr Gln Ser Ser Ser Ser Phe Ser Val Ser Leu Gly
1               5                   10                  15

Asp Arg Val Thr Ile Thr Cys Lys Ser Ser Glu Val Ile Tyr Asn Arg
            20                  25                  30

Leu Ala Trp Phe Gln Gln Lys Pro Gly Asn Ala Pro Arg Leu Leu Ile
        35                  40                  45

Ser Gly Ala Thr Thr Leu Glu Ser Gly Phe Pro Ser Arg Phe Ser Gly
    50                  55                  60

Ser Gly Ser Gly Lys Asp Tyr Thr Leu Ser Ile Thr Ser Leu Gln Ile
65                  70                  75                  80

Glu Asp Val Ser Thr Tyr Tyr Cys Gln Gln Tyr Trp Asn Lys Pro Phe
                85                  90                  95

Thr Phe Gly Ser Gly Thr Lys Leu Glu Val Lys
            100                 105


<210> SEQ ID NO 9
<211> LENGTH: 123
<212> TYPE: PRT
<213> ORGANISM: Mus musculus

<400> SEQUENCE: 9

Gln Val Gln Leu Gln Gln Pro Gly Thr Glu Leu Val Lys Pro Gly Ser
1               5                   10                  15

Pro Val Lys Leu Ser Cys Lys Ala Ser Gly Tyr Thr Phe Thr Ser Phe
            20                  25                  30

Trp Leu Asn Trp Val Gln Gln Arg Pro Gly Arg Gly Leu Glu Trp Ile
        35                  40                  45

Gly Lys Ile Asp Pro Ser Asp Ser Glu Ile Arg Tyr Asn Gln Lys Phe
    50                  55                  60

Lys Asp Lys Ala Thr Leu Thr Val Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95
```

```
Ala Arg Gly Gly Gly Ile Tyr Tyr Asp Tyr Asp Gly Ala Met Asp Tyr
            100                 105                 110

Trp Gly Gln Gly Thr Ser Val Thr Val Ser Ser
        115                 120


<210> SEQ ID NO 10
<211> LENGTH: 107
<212> TYPE: PRT
<213> ORGANISM: Mus musculus

<400> SEQUENCE: 10

Asp Ile Gln Met Thr Gln Ser Ser Ser Ser Phe Ser Val Ser Leu Gly
1               5                   10                  15

Asp Arg Leu Thr Ile Thr Cys Lys Ala Ser Glu Val Ile Tyr Asn Arg
            20                  25                  30

Leu Ala Trp Phe Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Arg Lys Asp Tyr Thr Leu Ser Ile Ser Ser Leu Gln Thr
65                  70                  75                  80

Glu Asp Val Ala Thr Tyr Tyr Cys Gln Gln Tyr Trp Ser Ser Pro Phe
                85                  90                  95

Thr Phe Gly Ser Gly Thr Lys Leu Glu Ile Lys
            100                 105


<210> SEQ ID NO 11
<211> LENGTH: 369
<212> TYPE: DNA
<213> ORGANISM: Mus musculus

<400> SEQUENCE: 11

caggtccaac tgcagcagcc tggggctgag cttgtgaagc ctggggctcc agtgaaactg     60

tcctgcaagg cttctggcta caccttcacc agctactgga tgaactgggt gaggcagagg    120

cctggacgag gcctcgagtg gattggaaag attgatcctt ccgatagtga aactcacttc    180

aatcaaaagt tcagggacaa ggccacactg actgtagaca aatcctccac cacagcctac    240

atccaactca gcagcctgac atctgaggac tctgcggtct attactgtgc aagagggggg    300

aggatctcct ttgattacga cgctgctttg gactactggg gtcaaggaac ctcagtcacc    360

gtatcctca                                                            369


<210> SEQ ID NO 12
<211> LENGTH: 321
<212> TYPE: DNA
<213> ORGANISM: Mus musculus

<400> SEQUENCE: 12

gacatcctga tgacacagtc ttcatcctcc ttttctgtat ctttaggaga cagagtcacc     60

attacttgca aatcaagtga ggtcatatat aatcggttag cctggtttca gcagaaacca    120

ggaaatgctc ctaggctctt aatatctggt gcgaccactt tggaatctgg gtttccttca    180

agattcagtg gcagtggatc tggaaaggat tacactctca gcattaccag tcttcagatt    240

gaagatgttt ctacttatta ctgtcaacag tattggaata agccattcac gttcggctcg    300

gggacaaagt tggaagtaaa a                                              321
```

<210> SEQ ID NO 13
<211> LENGTH: 369
<212> TYPE: DNA
<213> ORGANISM: Mus musculus

<400> SEQUENCE: 13

```
caggtccaac tacagcagcc tgggactgag cttgtgaagc ctgggtctcc agtgaaactg     60

tcctgcaagg cttctggcta caccttcacc agcttctggt tgaactgggt gcaacagagg    120

cctggacgag gcctcgaatg gattggaaag attgatcctt ccgatagtga aattcgctac    180

aatcaaaagt tcaaggacaa ggccacactg actgtagaca aatcgtccaa cacagcctac    240

atccaactca gcagcctgac atctgaggac tctgcggtct attactgtgc aagagggggg    300

gggatctact atgattacga cggcgctatg gactactggg gtcaaggaac ctcagtcacc    360

gtatcctca                                                            369
```

<210> SEQ ID NO 14
<211> LENGTH: 321
<212> TYPE: DNA
<213> ORGANISM: Mus musculus

<400> SEQUENCE: 14

```
gacatccaga tgacacaatc ttcatcctcc ttttctgtat ctctaggaga cagactcacc     60

attacttgca aggcaagtga ggtcatatat aatcgattag cctggtttca gcagaaacca    120

ggaaatgctc ctaggctctt aatatctggt gcaaccagtt tggaaactgg ggtgccttca    180

agattcagtg gcagtggatc tagaaaggat tacactctca gcatttccag tcttcagact    240

gaagatgttg ctacttatta ctgtcaacag tattggagtt ctccattcac gttcggctcg    300

gggacaaagt tggaaataaa a                                              321
```

<210> SEQ ID NO 15
<211> LENGTH: 120
<212> TYPE: PRT
<213> ORGANISM: Mus musculus

<400> SEQUENCE: 15

```
Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ser Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Met Ile Thr Tyr Tyr Ala Met Asp Tyr Trp Gly Gln
            100                 105                 110

Gly Thr Ser Val Thr Val Ser Ser
        115                 120
```

<210> SEQ ID NO 16
<211> LENGTH: 107
<212> TYPE: PRT
<213> ORGANISM: Mus musculus

<400> SEQUENCE: 16

```
Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105
```

<210> SEQ ID NO 17
<211> LENGTH: 95
<212> TYPE: PRT
<213> ORGANISM: Homo sapiens

<400> SEQUENCE: 17

```
Ser Pro Gln Lys Val Glu Val Asp Ile Ile Asp Asp Asn Phe Ile Leu
1               5                   10                  15

Arg Trp Asn Arg Ser Asp Glu Ser Val Gly Asn Val Thr Phe Ser Phe
            20                  25                  30

Asp Tyr Gln Lys Thr Gly Met Asp Asn Trp Ile Lys Leu Ser Gly Cys
        35                  40                  45

Gln Asn Ile Thr Ser Thr Lys Cys Asn Phe Ser Ser Leu Lys Leu Asn
    50                  55                  60

Val Tyr Glu Glu Ile Lys Leu Arg Ile Arg Ala Glu Lys Glu Asn Thr
65                  70                  75                  80

Ser Ser Trp Tyr Glu Val Asp Ser Phe Thr Pro Phe Arg Lys Ala
                85                  90                  95
```

<210> SEQ ID NO 18
<211> LENGTH: 101
<212> TYPE: PRT
<213> ORGANISM: Homo sapiens

<400> SEQUENCE: 18

```
Gln Ile Gly Pro Pro Glu Val His Leu Glu Ala Glu Asp Lys Ala Ile
1               5                   10                  15

Val Ile His Ile Ser Pro Gly Thr Lys Asp Ser Val Met Trp Ala Leu
            20                  25                  30

Asp Gly Leu Ser Phe Thr Tyr Ser Leu Val Ile Trp Lys Asn Ser Ser
        35                  40                  45

Gly Val Glu Glu Arg Ile Glu Asn Ile Tyr Ser Arg His Lys Ile Tyr
    50                  55                  60

Lys Leu Ser Pro Glu Thr Thr Tyr Cys Leu Lys Val Lys Ala Ala Leu
65                  70                  75                  80

Leu Thr Ser Trp Lys Ile Gly Val Tyr Ser Pro Val His Cys Ile Lys
                85                  90                  95

Thr Thr Val Glu Asn
            100
```

```
<210> SEQ ID NO 19
<211> LENGTH: 99
<212> TYPE: PRT
<213> ORGANISM: Homo sapiens

<400> SEQUENCE: 19

Pro Pro Glu Asn Ile Glu Val Ser Val Gln Asn Gln Asn Tyr Val Leu
1               5                   10                  15

Lys Trp Asp Tyr Thr Tyr Ala Asn Met Thr Phe Gln Val Gln Trp Leu
            20                  25                  30

His Ala Phe Leu Lys Arg Asn Pro Gly Asn His Leu Tyr Lys Trp Lys
        35                  40                  45

Gln Ile Pro Asp Cys Glu Asn Val Lys Thr Thr Gln Cys Val Phe Pro
    50                  55                  60

Gln Asn Val Phe Gln Lys Gly Ile Tyr Leu Leu Arg Val Gln Ala Ser
65                  70                  75                  80

Asp Gly Asn Asn Thr Ser Phe Trp Ser Glu Glu Ile Lys Phe Asp Thr
                85                  90                  95

Glu Ile Gln


<210> SEQ ID NO 20
<211> LENGTH: 102
<212> TYPE: PRT
<213> ORGANISM: Homo sapiens

<400> SEQUENCE: 20

Phe Leu Leu Pro Pro Val Phe Asn Ile Arg Ser Leu Ser Asp Ser Phe
1               5                   10                  15

His Ile Tyr Ile Gly Ala Pro Lys Gln Ser Gly Asn Thr Pro Val Ile
            20                  25                  30

Gln Asp Tyr Pro Leu Ile Tyr Glu Ile Ile Phe Trp Glu Asn Thr Ser
        35                  40                  45

Asn Ala Glu Arg Lys Ile Ile Glu Lys Lys Thr Asp Val Thr Val Pro
    50                  55                  60

Asn Leu Lys Pro Leu Thr Val Tyr Cys Val Lys Ala Arg Ala His Thr
65                  70                  75                  80

Met Asp Glu Lys Leu Asn Lys Ser Ser Val Phe Ser Asp Ala Val Cys
                85                  90                  95

Glu Lys Thr Lys Pro Gly
            100


<210> SEQ ID NO 21
<211> LENGTH: 5
<212> TYPE: PRT
<213> ORGANISM: Mus musculus

<400> SEQUENCE: 21

Ser Tyr Trp Met Asn
1               5


<210> SEQ ID NO 22
<211> LENGTH: 17
<212> TYPE: PRT
<213> ORGANISM: Mus musculus

<400> SEQUENCE: 22

Lys Ile Asp Pro Ser Asp Ser Glu Thr His Phe Asn Gln Lys Phe Arg
1               5                   10                  15

Asp
```

<210> SEQ ID NO 23
<211> LENGTH: 14
<212> TYPE: PRT
<213> ORGANISM: Mus musculus

<400> SEQUENCE: 23

Gly Gly Arg Ile Ser Phe Asp Tyr Asp Ala Ala Leu Asp Tyr
1               5                   10

<210> SEQ ID NO 24
<211> LENGTH: 9
<212> TYPE: PRT
<213> ORGANISM: Mus musculus

<400> SEQUENCE: 24

Gln Gln Tyr Trp Asn Lys Pro Phe Thr
1               5

<210> SEQ ID NO 25
<211> LENGTH: 5
<212> TYPE: PRT
<213> ORGANISM: Mus musculus

<400> SEQUENCE: 25

Ser Phe Trp Leu Asn
1               5

<210> SEQ ID NO 26
<211> LENGTH: 17
<212> TYPE: PRT
<213> ORGANISM: Mus musculus

<400> SEQUENCE: 26

Lys Ile Asp Pro Ser Asp Ser Glu Ile Arg Tyr Asn Gln Lys Phe Lys
1               5                   10                  15

Asp

<210> SEQ ID NO 27
<211> LENGTH: 14
<212> TYPE: PRT
<213> ORGANISM: Mus musculus

<400> SEQUENCE: 27

Gly Gly Gly Ile Tyr Tyr Asp Tyr Asp Gly Ala Met Asp Tyr
1               5                   10

<210> SEQ ID NO 28
<211> LENGTH: 9
<212> TYPE: PRT
<213> ORGANISM: Mus musculus

<400> SEQUENCE: 28

Gln Gln Tyr Trp Ser Ser Pro Phe Thr
1               5

<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: s is c or g
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(7)
<223> OTHER INFORMATION: n in location 6 is a, c, g or t; m in location 7 is a or c
<220> FEATURE:
<221> NAME/KEY: misc_feature
<222> LOCATION: (13)..(13)
<223> OTHER INFORMATION: s is c or g
<220> FEATURE:
<221> NAME/KEY: misc_feature
<222> LOCATION: (16)..(16)
<223> OTHER INFORMATION: s is c or g

<400> SEQUENCE: 29
sargtnmagc tgsagsagtc 20

<210> SEQ ID NO 30
<211> LENGTH: 23
<212> TYPE: DNA
<213> ORGANISM: Artificial Sequence
<220> FEATURE:
<223> OTHER INFORMATION: Synthetic

<400> SEQUENCE: 30
cttgaccagg catcctagag tca 23

<210> SEQ ID NO 31
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: y is c or t
<220> FEATURE:
<221> NAME/KEY: misc_feature
<222> LOCATION: (10)..(10)
<223> OTHER INFORMATION: m is a or c
<220> FEATURE:
<221> NAME/KEY: misc_feature
<222> LOCATION: (12)..(12)
<223> OTHER INFORMATION: s is c or g
<220> FEATURE:
<221> NAME/KEY: misc_feature
<222> LOCATION: (15)..(15)
<223> OTHER INFORMATION: m is a or c
<220> FEATURE:
<221> NAME/KEY: misc_feature
<222> LOCATION: (18)..(19)
<223> OTHER INFORMATION: r in location 18 is a or g; w in location 19 is a or t
<220> FEATURE:
<221> NAME/KEY: misc_feature
<222> LOCATION: (22)..(22)
<223> OTHER INFORMATION: m is a or c

<400> SEQUENCE: 31
gayattgtgm tsacmcarwc tmca 24

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32

```
ggatacagtt ggtgcagcat c                                              21
```

<210> SEQ ID NO 33
<211> LENGTH: 30
<212> TYPE: PRT
<213> ORGANISM: Homo sapiens

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 34
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be Ala or Arg
<220> FEATURE:
<221> NAME/KEY: misc_feature
<222> LOCATION: (13)..(13)
<223> OTHER INFORMATION: Xaa can be Met or Ile

<400> SEQUENCE: 34

```
Trp Val Arg Gln Xaa Pro Gly Gln Gly Leu Glu Trp Xaa Gly
1               5                   10
```

<210> SEQ ID NO 35
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be Met or Leu
<220> FEATURE:
<221> NAME/KEY: misc_feature
<222> LOCATION: (6)..(6)
<223> OTHER INFORMATION: Xaa can be Arg or Val
<220> FEATURE:
<221> NAME/KEY: misc_feature
<222> LOCATION: (8)..(8)
<223> OTHER INFORMATION: Xaa can be Thr or Lys

<400> SEQUENCE: 35

```
Arg Val Thr Xaa Thr Xaa Asp Xaa Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 36
<211> LENGTH: 11
<212> TYPE: PRT
<213> ORGANISM: Homo sapiens

<400> SEQUENCE: 36

```
Trp Gly Gln Gly Thr Leu Val Thr Val Ser Ser
1               5                   10
```

<210> SEQ ID NO 37
<211> LENGTH: 23
<212> TYPE: PRT
<213> ORGANISM: Homo sapiens

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 38
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be Lys or Asn
<220> FEATURE:
<221> NAME/KEY: misc_feature
<222> LOCATION: (15)..(15)
<223> OTHER INFORMATION: Xaa can be Tyr or Ser

<400> SEQUENCE: 38

```
Trp Tyr Gln Gln Lys Pro Gly Xaa Ala Pro Lys Leu Leu Ile Xaa
1               5                   10                  15
```

<210> SEQ ID NO 39
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: Xaa can be Thr or Lys
<220> FEATURE:
<221> NAME/KEY: misc_feature
<222> LOCATION: (15)..(15)
<223> OTHER INFORMATION: Xaa can be Phe or Tyr

<400> SEQUENCE: 39

```
Gly Val Pro Ser Arg Phe Ser Gly Ser Gly Ser Gly Xaa Asp Xaa Thr
1               5                   10                  15

Leu Thr Ile Ser Ser Leu Gln Pro Glu Asp Phe Ala Thr Tyr Tyr Cys
            20                  25                  30
```

<210> SEQ ID NO 40
<211> LENGTH: 10
<212> TYPE: PRT
<213> ORGANISM: Homo sapiens

<400> SEQUENCE: 40

```
Phe Gly Gln Gly Thr Lys Leu Glu Ile Lys
1               5                   10
```

<210> SEQ ID NO 41
<211> LENGTH: 14
<212> TYPE: PRT
<213> ORGANISM: Homo sapiens

<400> SEQUENCE: 41

```
Trp Val Arg Gln Ala Pro Gly Gln Gly Leu Glu Trp Met Gly
```

```
1               5                   10


<210> SEQ ID NO 42
<211> LENGTH: 14
<212> TYPE: PRT
<213> ORGANISM: Homo sapiens

<400> SEQUENCE: 42

Trp Val Arg Gln Ala Pro Gly Gln Gly Leu Glu Trp Ile Gly
1               5                   10


<210> SEQ ID NO 43
<211> LENGTH: 14
<212> TYPE: PRT
<213> ORGANISM: Homo sapiens

<400> SEQUENCE: 43

Trp Val Arg Gln Arg Pro Gly Gln Gly Leu Glu Trp Ile Gly
1               5                   10


<210> SEQ ID NO 44
<211> LENGTH: 32
<212> TYPE: PRT
<213> ORGANISM: Homo sapiens

<400> SEQUENCE: 44

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30


<210> SEQ ID NO 45
<211> LENGTH: 32
<212> TYPE: PRT
<213> ORGANISM: Homo sapiens

<400> SEQUENCE: 45

Arg Val Thr Leu Thr Val Asp Lys Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30


<210> SEQ ID NO 46
<211> LENGTH: 15
<212> TYPE: PRT
<213> ORGANISM: Homo sapiens

<400> SEQUENCE: 46

Trp Tyr Gln Gln Lys Pro Gly Lys Ala Pro Lys Leu Leu Ile Tyr
1               5                   10                  15


<210> SEQ ID NO 47
<211> LENGTH: 15
<212> TYPE: PRT
<213> ORGANISM: Homo sapiens

<400> SEQUENCE: 47

Trp Tyr Gln Gln Lys Pro Gly Lys Ala Pro Lys Leu Leu Ile Ser
1               5                   10                  15


<210> SEQ ID NO 48
<211> LENGTH: 15
<212> TYPE: PRT
<213> ORGANISM: Homo sapiens
```

<400> SEQUENCE: 48

```
Trp Tyr Gln Gln Lys Pro Gly Asn Ala Pro Lys Leu Leu Ile Ser
1               5                   10                  15
```

<210> SEQ ID NO 49
<211> LENGTH: 32
<212> TYPE: PRT
<213> ORGANISM: Homo sapiens

<400> SEQUENCE: 49

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 50
<211> LENGTH: 32
<212> TYPE: PRT
<213> ORGANISM: Homo sapiens

<400> SEQUENCE: 50

```
Gly Val Pro Ser Arg Phe Ser Gly Ser Gly Ser Gly Lys Asp Tyr Thr
1               5                   10                  15

Leu Thr Ile Ser Ser Leu Gln Pro Glu Asp Phe Ala Thr Tyr Tyr Cys
            20                  25                  30
```

<210> SEQ ID NO 51
<211> LENGTH: 123
<212> TYPE: PRT
<213> ORGANISM: Artificial Sequence
<220> FEATURE:
<223> OTHER INFORMATION: Synthetic

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Lys Ile Asp Pro Ser Asp Ser Glu Thr His Phe Asn Gln Lys Phe
    50                  55                  60

Arg Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Leu Val Thr Val Ser Ser
        115                 120
```

<210> SEQ ID NO 52
<211> LENGTH: 123
<212> TYPE: PRT
<213> ORGANISM: Artificial Sequence
<220> FEATURE:
<223> OTHER INFORMATION: Synthetic

<400> SEQUENCE: 52

```
Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Lys Ile Asp Pro Ser Asp Ser Glu Thr His Phe Asn Gln Lys Phe
    50                  55                  60

Arg Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Leu Val Thr Val Ser Ser
        115                 120


<210> SEQ ID NO 53
<211> LENGTH: 123
<212> TYPE: PRT
<213> ORGANISM: Artificial Sequence
<220> FEATURE:
<223> OTHER INFORMATION: Synthetic

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Ile
        35                  40                  45

Gly Lys Ile Asp Pro Ser Asp Ser Glu Thr His Phe Asn Gln Lys Phe
    50                  55                  60

Arg Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Leu Val Thr Val Ser Ser
        115                 120


<210> SEQ ID NO 54
<211> LENGTH: 123
<212> TYPE: PRT
<213> ORGANISM: Artificial Sequence
<220> FEATURE:
<223> OTHER INFORMATION: Synthetic

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Arg Pro Gly Gln Gly Leu Glu Trp Ile
        35                  40                  45

Gly Lys Ile Asp Pro Ser Asp Ser Glu Thr His Phe Asn Gln Lys Phe
    50                  55                  60
```

```
Arg Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Leu Val Thr Val Ser Ser
        115                 120


<210> SEQ ID NO 55
<211> LENGTH: 107
<212> TYPE: PRT
<213> ORGANISM: Artificial Sequence
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ser Ser Glu Val Ile Tyr Asn Arg
            20                  25                  30

Leu Ala Trp Tyr Gln Gln Lys Pro Gly Lys Ala Pro Lys Leu Leu Ile
        35                  40                  45

Tyr Gly Ala Thr Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Asn Lys Pro Phe
                85                  90                  95

Thr Phe Gly Gln Gly Thr Lys Leu Glu Ile Lys
            100                 105


<210> SEQ ID NO 56
<211> LENGTH: 107
<212> TYPE: PRT
<213> ORGANISM: Artificial Sequence
<220> FEATURE:
<223> OTHER INFORMATION: Synthetic

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ser Ser Glu Val Ile Tyr Asn Arg
            20                  25                  30

Leu Ala Trp Tyr Gln Gln Lys Pro Gly Lys Ala Pro Lys Leu Leu Ile
        35                  40                  45

Tyr Gly Ala Thr Thr Leu Glu Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Asn Lys Pro Phe
                85                  90                  95

Thr Phe Gly Gln Gly Thr Lys Leu Glu Ile Lys
            100                 105


<210> SEQ ID NO 57
<211> LENGTH: 107
<212> TYPE: PRT
<213> ORGANISM: Artificial Sequence
```

<220> FEATURE:
<223> OTHER INFORMATION: Synthetic

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Glu Val Ile Tyr Asn Arg
            20                  25                  30

Leu Ala Trp Tyr Gln Gln Lys Pro Gly Lys Ala Pro Lys Leu Leu Ile
        35                  40                  45

Ser Gly Ala Thr Thr Leu Glu Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Asn Lys Pro Phe
                85                  90                  95

Thr Phe Gly Gln Gly Thr Lys Leu Glu Ile Lys
            100                 105
```

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Glu Val Ile Tyr Asn Arg
            20                  25                  30

Leu Ala Trp Tyr Gln Gln Lys Pro Gly Asn Ala Pro Lys Leu Leu Ile
        35                  40                  45

Ser Gly Ala Thr Thr Leu Glu Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Asn Lys Pro Phe
                85                  90                  95

Thr Phe Gly Gln Gly Thr Lys Leu Glu Ile Lys
            100                 105
```

<210> SEQ ID NO 59
<211> LENGTH: 123
<212> TYPE: PRT
<213> ORGANISM: Homo sapiens

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Ala Ala Leu Asp Tyr
            100                 105                 110

Trp Gly Gln Gly Thr Leu Val Thr Val Ser Ser
        115                 120


<210> SEQ ID NO 60
<211> LENGTH: 107
<212> TYPE: PRT
<213> ORGANISM: Homo sapiens

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105


<210> SEQ ID NO 61
<211> LENGTH: 330
<212> TYPE: PRT
<213> ORGANISM: Homo sapiens

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 62
<211> LENGTH: 330
<212> TYPE: PRT
<213> ORGANISM: Artificial Sequence
<220> FEATURE:
<223> OTHER INFORMATION: Synthetic

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 63
<211> LENGTH: 66
<212> TYPE: PRT
<213> ORGANISM: Homo sapiens

<400> SEQUENCE: 63

Gly Thr Lys Asp Ser Val Met Trp Ala Leu Asp Gly Leu Ser Phe Thr
1               5                   10                  15

Tyr Ser Leu Val Ile Trp Lys Asn Ser Ser Gly Val Glu Glu Arg Ile
            20                  25                  30

Glu Asn Ile Tyr Ser Arg His Lys Ile Tyr Lys Leu Ser Pro Glu Thr
        35                  40                  45

Thr Tyr Cys Leu Lys Val Lys Ala Ala Leu Leu Thr Ser Trp Lys Ile
    50                  55                  60

Gly Val
65


<210> SEQ ID NO 64
<211> LENGTH: 66
<212> TYPE: PRT
<213> ORGANISM: Mus musculus

<400> SEQUENCE: 64

Pro Gly Gln Asp Gly Asn Met Trp Ala Leu Glu Lys Pro Ser Phe Ser
1               5                   10                  15

Tyr Thr Ile Arg Ile Trp Gln Lys Ser Ser Ser Asp Lys Lys Thr Ile
            20                  25                  30

Asn Ser Thr Tyr Tyr Val Glu Lys Ile Pro Glu Leu Leu Pro Glu Thr
        35                  40                  45

Thr Tyr Cys Leu Glu Val Lys Ala Ile His Pro Ser Leu Lys Lys His
    50                  55                  60

Ser Asn
65


<210> SEQ ID NO 65
<211> LENGTH: 14
<212> TYPE: PRT
<213> ORGANISM: Artificial Sequence
<220> FEATURE:
<223> OTHER INFORMATION: Synthetic
```

<400> SEQUENCE: 65

```
Gly Gly Arg Ile Ser Phe Asp Tyr Asp Gly Ala Leu Asp Tyr
1               5                   10
```

<210> SEQ ID NO 66
<211> LENGTH: 7
<212> TYPE: PRT
<213> ORGANISM: Mus musculus

<400> SEQUENCE: 66

```
Gly Ala Thr Ser Leu Glu Thr
1               5
```

<210> SEQ ID NO 67
<211> LENGTH: 123
<212> TYPE: PRT
<213> ORGANISM: Artificial Sequence
<220> FEATURE:
<223> OTHER INFORMATION: Synthetic

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Lys Ile Asp Pro Ser Asp Ser Glu Thr His Phe Asn Gln Lys Phe
    50                  55                  60

Arg Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Ile Ser Phe Asp Tyr Asp Gly Ala Leu Asp Tyr
            100                 105                 110

Trp Gly Gln Gly Thr Leu Val Thr Val Ser Ser
        115                 120
```

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Glu Val Ile Tyr Asn Arg
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Asn Lys Pro Phe
                85                  90                  95

Thr Phe Gly Gln Gly Thr Lys Leu Glu Ile Lys
```

100 105

<210> SEQ ID NO 69
<211> LENGTH: 557
<212> TYPE: PRT
<213> ORGANISM: Artificial Sequence
<220> FEATURE:
<223> OTHER INFORMATION: Synthetic

<400> SEQUENCE: 69

Met Met Val Val Leu Leu Gly Ala Thr Thr Leu Val Leu Val Ala Val
1 5 10 15

Ala Pro Trp Val Leu Ser Ala Ala Ala Gly Gly Lys Asn Leu Lys Ser
20 25 30

Pro Gln Lys Val Glu Val Asp Ile Ile Asp Asp Asn Phe Ile Leu Arg
35 40 45

Trp Asn Arg Ser Asp Glu Ser Val Gly Asn Val Thr Phe Ser Phe Asp
50 55 60

Tyr Gln Lys Thr Gly Met Asp Asn Trp Ile Lys Leu Ser Gly Cys Gln
65 70 75 80

Asn Ile Thr Ser Thr Lys Cys Asn Phe Ser Ser Leu Lys Leu Asn Val
85 90 95

Tyr Glu Glu Ile Lys Leu Arg Ile Arg Ala Glu Lys Glu Asn Thr Ser
100 105 110

Ser Trp Tyr Glu Val Asp Ser Phe Thr Pro Phe Arg Lys Ala Gln Ile
115 120 125

Gly Pro Pro Glu Val His Leu Glu Ala Glu Asp Lys Ala Ile Val Ile
130 135 140

His Ile Ser Pro Pro Gly Gln Asp Gly Asn Met Trp Ala Leu Glu Lys
145 150 155 160

Pro Ser Phe Ser Tyr Thr Ile Arg Ile Trp Gln Lys Ser Ser Ser Asp
165 170 175

Lys Lys Thr Ile Asn Ser Thr Tyr Tyr Val Glu Lys Ile Pro Glu Leu
180 185 190

Leu Pro Glu Thr Thr Tyr Cys Leu Glu Val Lys Ala Ile His Pro Ser
195 200 205

Leu Lys Lys His Ser Asn Tyr Ser Pro Val His Cys Ile Lys Thr Thr
210 215 220

Val Glu Asn Glu Leu Pro Pro Pro Glu Asn Ile Glu Val Ser Val Gln
225 230 235 240

Asn Gln Asn Tyr Val Leu Lys Trp Asp Tyr Thr Tyr Ala Asn Met Thr
245 250 255

Phe Gln Val Gln Trp Leu His Ala Phe Leu Lys Arg Asn Pro Gly Asn
260 265 270

His Leu Tyr Lys Trp Lys Gln Ile Pro Asp Cys Glu Asn Val Lys Thr
275 280 285

Thr Gln Cys Val Phe Pro Gln Asn Val Phe Gln Lys Gly Ile Tyr Leu
290 295 300

Leu Arg Val Gln Ala Ser Asp Gly Asn Asn Thr Ser Phe Trp Ser Glu
305 310 315 320

Glu Ile Lys Phe Asp Thr Glu Ile Gln Ala Phe Leu Leu Pro Pro Val
325 330 335

Phe Asn Ile Arg Ser Leu Ser Asp Ser Phe His Ile Tyr Ile Gly Ala
340 345 350

Pro Lys Gln Ser Gly Asn Thr Pro Val Ile Gln Asp Tyr Pro Leu Ile

-continued 355 360 365

Tyr Glu Ile Ile Phe Trp Glu Asn Thr Ser Asn Ala Glu Arg Lys Ile
370 375 380

Ile Glu Lys Lys Thr Asp Val Thr Val Pro Asn Leu Lys Pro Leu Thr
385 390 395 400

Val Tyr Cys Val Lys Ala Arg Ala His Thr Met Asp Glu Lys Leu Asn
405 410 415

Lys Ser Ser Val Phe Ser Asp Ala Val Cys Glu Lys Thr Lys Pro Gly
420 425 430

Asn Thr Ser Lys Ile Trp Leu Ile Val Gly Ile Cys Ile Ala Leu Phe
435 440 445

Ala Leu Pro Phe Val Ile Tyr Ala Ala Lys Val Phe Leu Arg Cys Ile
450 455 460

Asn Tyr Val Phe Phe Pro Ser Leu Lys Pro Ser Ser Ser Ile Asp Glu
465 470 475 480

Tyr Phe Ser Glu Gln Pro Leu Lys Asn Leu Leu Leu Ser Thr Ser Glu
485 490 495

Glu Gln Ile Glu Lys Cys Phe Ile Ile Glu Asn Ile Ser Thr Ile Ala
500 505 510

Thr Val Glu Glu Thr Asn Gln Thr Asp Glu Asp His Lys Lys Tyr Ser
515 520 525

Ser Gln Thr Ser Gln Asp Ser Gly Asn Tyr Ser Asn Glu Asp Glu Ser
530 535 540

Glu Ser Lys Thr Ser Glu Glu Leu Gln Gln Asp Phe Val
545 550 555

<210> SEQ ID NO 70
<211> LENGTH: 11
<212> TYPE: PRT
<213> ORGANISM: Mus musculus

<400> SEQUENCE: 70

Lys Ser Ser Glu Val Ile Tyr Asn Arg Leu Ala
1 5 10

<210> SEQ ID NO 71
<211> LENGTH: 7
<212> TYPE: PRT
<213> ORGANISM: Mus musculus

<400> SEQUENCE: 71

Gly Ala Thr Thr Leu Glu Ser
1 5

<210> SEQ ID NO 72
<211> LENGTH: 11
<212> TYPE: PRT
<213> ORGANISM: Mus musculus

<400> SEQUENCE: 72

Lys Ala Ser Glu Val Ile Tyr Asn Arg Leu Ala
1 5 10